(12) United States Patent
Davis et al.

(10) Patent No.: US 11,891,640 B1
(45) Date of Patent: Feb. 6, 2024

(54) CROP PROTECTION IN ALGAE BY EXOGENOUS TERPENE EXPRESSION

(71) Applicant: National Technology & Engineering Solutions of Sandia, LLC, Albuquerque, NM (US)

(72) Inventors: Ryan Wesley Davis, San Jose, CA (US); Tyler Phillips Eckles, Livermore, CA (US); Nataly Lyn Beck, Livermore, CA (US); Oliver Kilian, Castro Valley, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 214 days.

(21) Appl. No.: 17/153,106

(22) Filed: Jan. 20, 2021

(51) Int. Cl.
  *C12N 9/88* (2006.01)
  *C12N 9/10* (2006.01)
  *C12N 1/12* (2006.01)

(52) U.S. Cl.
  CPC ............... *C12N 9/88* (2013.01); *C12N 1/12* (2013.01); *C12N 9/1085* (2013.01)

(58) Field of Classification Search
  CPC .......... C12N 9/88; C12N 1/12; C12N 9/1085
  See application file for complete search history.

(56) References Cited

U.S. PATENT DOCUMENTS

| | | |
|---|---|---|
| 8,119,859 B2 | 2/2012 | Vick et al. |
| 8,314,228 B2 | 11/2012 | Kilian et al. |
| 8,318,482 B2 | 11/2012 | Vick et al. |
| 8,404,473 B2 | 3/2013 | Kilian et al. |
| 8,440,805 B2 | 5/2013 | Kilian et al. |
| 8,481,974 B1 | 7/2013 | Davis et al. |
| 8,685,723 B2 | 4/2014 | Vick et al. |
| 8,722,359 B2 | 5/2014 | Kilian et al. |
| 8,753,879 B2 | 6/2014 | Kilian et al. |
| 8,759,615 B2 | 6/2014 | Vick et al. |
| 8,785,610 B2 | 7/2014 | Kilian et al. |
| 8,809,046 B2 | 8/2014 | Kilian et al. |
| 8,865,468 B2 | 10/2014 | Kilian et al. |
| 9,029,137 B2 | 5/2015 | Kilian et al. |
| 9,376,687 B2 | 6/2016 | Kilian et al. |
| 9,783,812 B2 | 10/2017 | Kilian et al. |
| 10,077,454 B1 | 9/2018 | Davis et al. |
| 10,400,254 B1* | 9/2019 | Wu ..................... C12P 5/007 |
| 10,683,519 B1 | 6/2020 | Davis et al. |
| 2020/0017885 A1 | 1/2020 | Wu et al. |
| 2020/0370071 A1 | 11/2020 | Davis et al. |
| 2021/0292797 A1* | 9/2021 | Lee ..................... C12P 17/08 |

FOREIGN PATENT DOCUMENTS

| | | | | |
|---|---|---|---|---|
| WO | WO-2020176998 A1 * | 9/2020 | ............. | C07K 14/21 |

OTHER PUBLICATIONS

Schneider, R.C.S. et al., "Potential production of biofuel from microalgae biomass produced in wastewater", Chapter 1 in Biodiesel-Feedstocks, Production and Applications, Prof. Zhen Fang (ed.), InTech, (Dec. 3, 2012), 22 pp.

Wu, W. et al., "Rapid discovery and functional characterization of terpene synthases from four endophytic Xylariaceae", PLoS One, (Feb. 17, 2016), 11(2):e0146983 (19 pp.).

Wu, W, "Quest of synthetic biology in the production of terpene as natural bioactive products and next generation fuel compounds", SAND Report No. SAND2015-9471C, (Oct. 1, 2015) (24 pp.).

Zhuang, X. et al., "Monoterpene production by the carotenogenic yeast Rhodosporidium toruloides", Microbial Cell Factories, (Dec. 1, 2019), 18: 54 (15 pp.).

* cited by examiner

*Primary Examiner* — Robert J Yamasaki
*Assistant Examiner* — Trevor Kane
(74) *Attorney, Agent, or Firm* — Samantha Updegraff; Fish & Richardson

(57) ABSTRACT

The present disclosure relates to terpene synthases capable of producing terpenoids. In one instance, a transformed organism can include terpene synthases or vectors encoding such synthases. One method of employing such synthases and organisms includes protecting an algal culture, in which the produced terpenoid can act as a biocide.

7 Claims, 17 Drawing Sheets

Specification includes a Sequence Listing.

\>HypCI4A-322581 (SEQ ID NO:1)
MSLAPSSGDYPSSHWTPLIHPLSEKVTREVDGYYLQHWPFPDERSRKKFVAAGFSRVTCFYFPKALNDRI
HFACRLLTVLFLIDDLLEYMSLEDGKAYNEKLIPISRGDVLPDRSVPVEYITYDLWESMRAHDRIMADDI
LEPVFTFMRAQTDSVRLEAMDLGRYLEYRERDVGKALLGALMRFSMGLVVPPEDLAIVRPIDFNCSRHLS
VINDIWSFEKELLASKNAHEEGGVLCSAVSVLADQVGISIDGSKRILYYLCREWEHRHETLVKEMLQVRD
TPALRSYVKGLEYQMSGNEMWSRTTMRYLAPKD

\>HypC027-392541 (SEQ ID NO:2)
MAPMAEECVSASPNQGHAKPVATPMRRAVHIPSSEWTAQIHPLHEKVIAEVDGYFLQHWPFPSEKTRKKF
VAAGFSRVTCLYFPKALDDRIHFACRLLTLLFLVDDILEHMSLEDGRAYNERLMPLFRGSVLPDRSVPVE
WISYDLWESMRAHDRDMADEIIEPVFTFMWAQTDPARLTEMGLGQYLEYRERDVGKALLAALMRFSMALI
VSPSDLEMVRPVDRNCSKHLSVINDIWSYEKEVLAAQTLHEEGGMLCTAVAVLSKEAEISTDASKRVLYH
LCREWEDEHRILVADILAQNDTPVLRAYLQGLEFQMSGNELWSRTTLRYVQPRP

\>DalEC12-12539 (SEQ ID NO:3)
MEYAQSTFTLLCHPRFEVVERETNEYFIANWPFPDVNSRDKFLKAGFSRCTCVYFPKAKDDRIHFACRLL
TLLFLIDDVLEDMSFEEGTAYNGRLMSIIRGDEVPDRSIPVQYISHDLWQSMRAHDQRLADGILEPLFIF
MQAQTDKRRAHSMSLGQYIEYRDKDIGQALLCALMRFCLDIKLTQHELDLVRPADVNCGIHIAIMNDIWS
FEKEALTAARGHDEGGVLCNSVAILSTETSLSTASSKRVLYCMCREWETKHRRFVDELGGGRDTTLWTYL
QGLEYQMSGNEAWSKLTPRYQIQESEKL

\>HypEC38-328361 (SEQ ID NO:4)
MAPMVEEYVPTSPTQDYAKPVATPIQRAVHIPASEWTAQIHPLHEKVIVEVDGYFLQHWPFPNEKARKKF
VAAGFSRVTCLYFPKALDDRIHFACRLLTLLFLVDDILEHMSLEDGRAYNERLMPLFRGSVLPDRSVPVE
WISYDLWESMRAHDRDMADEIIEPVFTFMRAQTDPARLTDMGLGQYLEYRERDVGKALLAALMRFSMALT
VSPSDLEMVRPVDRNCSKHLSVINDIWSYEKEVLAAQTLHEEGGMLCTAVAVLSKEAEISTDASKRVLYH
LCREWEDEHRILVADILAQNDTPVLRAYLQGLEFQMSGNELWSRTTLRYVQPRP

\>HypEC38-80361 (SEQ ID NO:5)
MEYAQSTFSLLRHPRFEEVERETNEYFLANWPFPDLNSRDKFLKAGFTRCTCMYFPKAKDDRIQFACRLL
TLLFLIDDVLENMSFEEGTAYNGKLMPIIRGDEVPNCSVPVQKISYDLWQSMRANDRELADGILEPLFIF
MRAQTDKRRAHSMSLGQYLEYRDKDIGQALLCALMRFCLDIKLTQHELDIVRPANVNCGNHIAVINDIWS
FEKEALTATHAHDEGGVLCNSVAILSAETALSTASSKRVLYCLCREWETKHQQFVDGLGDGHDAETLRAY
LQGLEYQMSGNEAWSKITPRYQIHESDRL

\>HypCI4A-59230 (SEQ ID NO:6)
MSVAVETITAPTVTLSTSKPLVKETWKIPASGWTPMIHPRAEEVSREVDNYFLEHWNFPDDNARSTFLKA
GFSRVTCLYFPLAKDDRIHFACRLLTVLFLIDDILEEMSFADGEALNNRLIELSKGPEYATPDRSIPAEY
VIYDLWESMRKHDLDLANEVLEPTFVFMRSQTDRVRLSIKELGEYLRYREKDVGKALLSALMRYSMELRP
TAEELAALRPLEENCSKHISIVNDIYSFEKEVIAAKTGHKEGSFLCSAVKVVATETALGISATKRVLWSM
VREWELVHDAMCDALLLAASGAGTNSQTVRDYMRGLQYQMSGNELWSCTTPRYIEAIDQAAR

\>Ari1 (SEQ ID NO:7)
MKKPNGTNGASSSLEPPPSTFQPLCHPLVEEVSKEVDGYFLQHWNFPNEKARKKFVAAGFSRVTCLYFPKALDD
RIHFACRLLTVLFLIDDLLEYMSFEEGSAYNEKLIPISRGDVLPDRSIPVEYIIYDLWESMRAHDREMADEILE
PVFLFMRAQTDRTRARPMGLGGYLEYRERDVGKELLAALMRFSMGLKLSPSELQRVREIDANCSKHLSVVNDIY
SYEKELYTSKTAHSEGGILCTSVQILAQEADVTAEAAKRVLFVMCREWELRHQLLVARLSAEGLETPGLAAYVE
GLEYQMSGNELWSQTTLRYSVVVD

\>Prx2 (SEQ ID NO:8)
MATSTETISSLAQPFVHLENPINSPLVKETIRPRNDTTITPPPTQWSYLCHPRVKEVQDEVDGYFLENWKFPSF
KAVRTFLDAKFSEVTCLYFPLALDDRIHFACRLLTVLFLIDDVLEHMSFADGEAYNNRLIPISRGDVLPDRTKP
EEFILYDLWESMRAHDAELANEVLEPTFVFMRAQTDRARLSIHELGHYLEYREKDVGKALLSALMRFSMGLRLS
ADELQDMKALEANCAKQLSVVNDIYSYDKEEEASRTGHKEGAFLCSAVKVLAEESKLGIPATKRVLWSMTREWE
TVHDEIVAEKIASPDGCSEAAKAYMKGLEYQMSGNEQWSKTTRRYN

FIG. 4A

```
CONSENSUS                                                 XXXXXXXXHPXXXXVXXEXXXYXXXX  25
HypCI4A-322581   MSL------APS--S----------------------GDYPS H TPLI P LSEK TRE V G   QH  37
HypC027-392541   MAPM-AEECVSA--SPNQCHAKPVATPMRR---------AVHIPS E TAQI R LHEK V AEV G   QH  58
DalEC12-12539    MEYA----------------------------------Q  T TLLC R RFEV E RPT E Y   AN  30
HypEC38-328361   MAPM-VEEYVPT--SPTQDYAKPVATPIQR---------AVHIPA E TAQI R LHEK V IVEV G   QH  58
HypEC38-80361    MEYA----------------------------------Q  T SLLR R RFEE V ERPT E Y   AN  30
HypCI4A-59230    MSVA--VETITA---PTVTLST--SKPLVKETWKI----PA  G TPMI H PRAEE V SREV N Y   EH  55
Ari1             MKKPNGTNGASS--S-----------------------LEPPP T QPLC H PLVEE V SKEV G   QH  43
Prx2             MATS---TETISSLAQPFVHLENPINSPLVKETIRPRNDTTITPPP Q SYLC H RVKE V QDEV G   EN  68

CONSENSUS        WXFPXXXXXXXFXXAFXXXTCXYFPXAXXDRIXFACRLLTXLFLXDDXLEXMSXXXGXAXNXXLXXXXX  95
HypCI4A-322581   WPF EDERSRKK F AAG F RVTC F YFP KAL DRIH FACRLLT L FL DD L EYMS LE C KAYNE L IEPS S  107
HypC027-392541   WPF ESEKTRKK F AAG F RVTC L YFP KAL DRIH FACRLLT L FL DD L EHMS LE C PAYNE L IMP F   128
DalEC12-12539    WPF EDVNSRDK F KAG F RCTC V YFP KAK DRIH FACRLLT L FL DD V LEDMS FE C TAYNG L IMS I   100
HypEC38-328361   WPF EDLNSRDK F KAG F RVTC M YFP KAK DRIQ FACRLLT L FL DD L EHMS LE C GTAYNE L LMP I   128
HypEC38-80361    WPF EDLNSRDK F KAG F RCTC M YFP KAK DRIQ FACRLLT L FL DD L ENMS LE C GTAYNG L LMP I   100
HypCI4A-59230    WNF EDDNARST F KAG F RVTC L YFP LAK DRIH FACRLLT L FL DD L EEMS FA C GEALNN L IES S   125
Ari1             WNF ENEKARKK F AAG F RVTC L YFP KAL DRIH FACRLLT L FL DD L EYMS FE C GSAYNE L IEPS S   113
Prx2             WKF ESFKAVRT F DAK F EVTC L YFP IAL DRIH FACRLLT L FL DD L EHMS FA C GEAYNN L IEP S   138

CONSENSUS        GXXXXXPXXXXPXXXXXXDLWXSMRXXDXXXAXXXEPXFXFMXXQTDXXRXXXXXLGXYXXYRXXDXGX 165
HypCI4A-322581   GD---VL R REVEMVY TYDLW SMPAH DRIMA D EEVT F MRAQT D SVR EAML LGRV EYR T DGK 175
HypC027-392541   GS---VL R REPVPVW SYDLW SMPAH DRDMA E EPVT F MWAQT D PAR TEMG LGQV EYR T DGK 196
DalEC12-12539    GDE--VL R REIEVY SHDLW SMPAH DQRLA G EPVT F MQAQT D KRR HSMS LGQV EYR T DGQ 168
HypEC38-328361   GS---VL R REVPVW SYDLW SMPAH DRDMA E EPVT F MRAQT D PAR TDMG LGQV EYR T DGQ 196
HypEC38-80361    GDE--VP C KPVPVW KSYDLW SMRAN DRELA G EELT F MPAQT D KRR HSMS LGQV EYR T DGQ 168
HypCI4A-59230    GPEYAT E REIPAV Y IYDLW SMRKH DLDIA E EPTV F MRSQT D PVR SIKE LGF YRYP T DGK 195
Ari1             GD---VL R REIPVV Y IYDLW SMPAH DREMA E EEVV F MRAQT D RTR RPMG LGGY EYR T DGK 181
Prx2             GD---VL R RKPE F LYDLW SMPAH DAELA E EPTV F MRAQT D RAR SIHE LGHV EYR T DGK 206

CONSENSUS        XLLXALMRXXXXXXXXXXLXXXXXXXXNCXXXXXXXNDIXSXXKEXXXXXXXXHXEGXXLCXXVXXXXXX 235
HypCI4A-322581   AL LGALMR SMG VVPPE L AIV P FNC SRH S S INDI S S KELLASKN H EEGGVL CSAV S AD 245
HypC027-392541   AL LAALMR SMA IVSPS L EMV P R NCGIH S S INDI S S KEVLAAQT H EEGGML CTAVA SK 266
DalEC12-12539    AL LCALMR CLD KLTQH L DLV P VNCGIH A A INDI S S KEALTAAR H DEGGVL CNSVA ST 238
HypEC38-328361   AL LAALMR SMA TVSPS L EMV P R NCSKH S S INDI S S KEVLAAQT H EEGGML CTAVA SK 266
HypEC38-80361    AL LCALMR CLD KLTQH L DIV P VNCGNH A A INDI S S KEALTATH H DEGGVL CNSVA SA 238
HypCI4A-59230    AL LSALMR SME RPTAE L AAL P ENCSKH S S VNDI S S KEVIAAKT H KEGSFL CSAV K AT 265
Ari1             EL LAALMR SMG KLSPS L QRV E ANCSKH S S VNDI S S KELYTSKT H SEGGIL CTSVQ AQ 251
Prx2             AL LSALMR SMG RLSAD L QDM A ANCAKQ S S VNDI S S KEEASRT H EKECAFL CSAV K AE 276

CONSENSUS        XXXXXXXXXXKRXLXXXXREWEXHXXXXXXXXXXXXXXXXXXXXXXXYXXGLXXQMSGNEXWSXXTXRY 303
HypCI4A-322581   VG SIDGS KR L YLC REWEH RR ETLVKEM-MQVRDT----PA RS YVKGL QMSGNE MWSRTT MRYLA 310
HypC027-392541   AE STDAS KR L HLC REWED EP RILVADI-MAQNDT----PV RA YLQGL QMSGNE LWSRTT LRYVQ 331
DalEC12-12539    TS STASS KR L CMC REWET KR RFVDEL-MGGRDT------T WT YLQGI QMSGNE AWSKLT PRYQI 302
HypEC38-328361   AE STDAS KR L HLC REWED EP RILVADI-MAQNDT----PV RA YLQGL QMSGNE LWSRTT LRYVQ 331
HypEC38-80361    TA STASS KR L CLC REWET KQ QFVDGL-MDGHDA----ET RA YLQGL QMSGNE AWSKIT PRYQI 303
HypCI4A-59230    TA GISATKR L SMV REWEL VE DAMCDALI AASGAGTNSQT RD YMRGL QMSGNE WSCTT PRYIE 335
Ari1             AD TAEAA KR L VMC REWEL RH QLLVARLS EGLET-----PG AA YVEGL QMSGNE IWSQTT LRYSV 317
Prx2             SK GIPAT KR L SMT REWE T VP DEIVAEKI SPDGC---SEA KA YMKGL QMSGNE QWSKTT TRRYN- 342

CONSENSUS                        (SEQ ID NO:10)
HypCI4A-322581   PKD----  313    (SEQ ID NO:1)
HypC027-392541   PRP----  334    (SEQ ID NO:2)
DalEC12-12539    QESEKL-  308    (SEQ ID NO:3)
HypEC38-328361   PRP----  334    (SEQ ID NO:4)
HypEC38-80361    HESDRL-  309    (SEQ ID NO:5)
HypCI4A-59230    AIDQAAR  342    (SEQ ID NO:6)
Ari1             VVD----  320    (SEQ ID NO:7)
Prx2             -------  342    (SEQ ID NO:8)
```

FIG. 4B

| | | |
|---|---|---|
| CONSENSUS 2A | LXDDXXEX | (SEQ ID NO:11) |
| CONSENSUS 2B | DDXXE | (SEQ ID NO:12) |
| HypCI4A-322581 | LIDDLLEY | |
| HypCO27-392541 | LVDDILEH | |
| DalEC12-12539 | LIDDVLED | |
| HypEC38-328361 | LVDDILEH | |
| HypEC38-80361 | LIDDVLEN | |
| HypCI4A-59230 | LIDDILEE | |
| Ari1 | LIDDLLEY | |
| Prx2 | LIDDVLEH | |

| | | |
|---|---|---|
| CONSENSUS 3A | XNDXXSXXKEXX | (SEQ ID NO:13) |
| CONSENSUS 3B | NDXXSXXKE | (SEQ ID NO:14) |
| HypCI4A-322581 | INDIWSFEKELL | |
| HypCO27-392541 | INDIWSYEKEVL | |
| DalEC12-12539 | MNDIWSFEKEAL | |
| HypEC38-328361 | INDIWSYEKEVL | |
| HypEC38-80361 | INDIWSFEKEAL | |
| HypCI4A-59230 | VNDIYSFEKEVI | |
| Ari1 | VNDIYSYEKELY | |
| Prx2 | VNDIYSYDKEEE | |

FIG. 5

```
tcgcgcgttt cggtgatgac ggtgaaaacc tctgacacat gcagctcccg gagacggtca cagcttgtct   70
gtaagcggat gccgggagca gacaagcccg tcagggcgcg tcagcgggtg ttggcgggtg tcggggctgg  140
cttaactatg cggcatcaga gcagattgta ctgagagtgc accatatgcg gtgtgaaata ccgcacagat  210
gcgtaaggag aaaataccgc atcaggcgcc attcgccatt caggctgcgc aactgttggg aagggcgatc  280
ggtgcgggcc tcttcgctat tacgccagct ggcgaaaggg ggatgtgctg caaggcgatt aagttgggta  350
acgccaggcgt tttcccagtc acgacgttgt aaaacgacgg ccagagaatt cgtttaaacC AGTGGGATAA  420
AAGGCAGTCC GAAGGTTTCC GTCATCCTCG TCCTCGTTCT CGTTTTCCAC CTACTCATCT TCCGTTTCTT  490
GAGTGCGTCG CCGCTGGGTT TTCCTGAAAT AAACGCTCTT TCATATTATT TTTTTTCATC TTTTTTTCTT  560
CTATTGTTTT TTTGACTTG TCTTTGACCT TGTCTGTAGC TCTTAACAGA TCAAAGGAAA AGCGAAGGCG  630
CCGCATGATC CTCGTCCTTC ACGAAACACA AACATCAGCC TCTTCACCCT CTTTCCCTGT TTCCTGCTAC  700
GAAATCGACA ACATTCAACA AGTCAGAAAC GCTCCTCTTC ACTAACACA CAATCGACCG CTGCTTTCCT  770
CCTTCCCTCC GCAGTAATCA ACACGTCTAT tctagaaatc TACATctagA CTTGAGAGAG TGGTGGAGTT  840
GACTATCGTG TGGAGTGTTT GGGGAGGGAA AGGGCGGAGC GTGAGTGCAA TGCGAGGTGG GCGAAGTGGG  910
CATGTGATAA ATGGCTGTGT GGTGGAGGCC TTCGCTGCGT GTCTGTGACT GTCTTGATTG TGTGCTTAGA  980
GTGAGATACC AAAGCAAGAT CTTCCCTGCC ATCCTTCAT TGTCCCACGG GCCGAAGAGA TGGGGGGCTT 1050
GACGAGAGGA CAGGGATGCA GGTGCGATGC GGTCCTGTCC tATGGGGCAG GAACCGCTGG GGTGCAGTGG 1120
CACAGAAGAC AGAAGGAGAA AACACATGCA CCAAATAAAC ATATGACAAA GAGTCAAGCA GTAGTCAAAA 1190
CAACCAAAAC GTAAGCAAGA CGGAACAAGA TGGCACGCGT CTGCAACAGA CCGGCTCGCG CCGAACGTGC 1260
CTCCTGCTTT TCAACGATCC TGCGAGGTCA ACCAGGATTT GCTCGCGGG ACGATTTCAT CCCCTTATCA 1330
ACGAGCCCTT GAGGCTCCAG GCGTGCTTCC ACACCCCAGT TGGTAACAGG ACATTGGGGC ATCTTGCCTA 1400
TCTTGTCTTA GTGCCGAAAG CCTCAACGAC CTCCtATGGG GTCTGCTCAA CGCCTCAACC TTGCAGTAAG 1470
GcATCCCCGA GGGCAAGACC CGCAAAGCCT TCTGTCGTCG GACAAAGCGG AGCGAGGGAA CAGGCTCAGC 1540
TCAACCCTCT TGAGAGCCCA TAAGTGCCCC CTGATCTATC TTCAACAGTC TTTCCCTGTC ACAAGAAAAC 1610
CCAGCTAGTT GACCAAGTTG CTAGAGCTGA TACCTTGTAC TTCGCTCTTT GTGTGCTTTA CCTGATTGGA 1680
CATGGACAGA CCTCCCCTTG CTCTTCCTTC TAGGAGCCTG GGCTCTCGCT CTTGTTCTTT CGAGAGACCT 1750
TTCCCTTGAG TTGCGTATCC AGCGATCAAG TATGAAGAGT GCTTTCAAAC CTAGATACGT TCTGCCCAGT 1820
TCTCTTGCCC TTTTCCACAC GTGCTCCACA TCTTCACACG ACTCGCACCA TACCCGACGA AACCCCTCAA 1890
AACATCGCAA CACTTACATC CCGCTCGTGT CCCACCCCG ATGCCATATC CTCTACAGCA GCAGCACCAC 1960
CACCACCACT TCTTAAGtAT GTCGCTCGCC CCCTCGTCGG GCGACTACCC TTCGTCGCAC TGGACGCCGC 2030
TCATCCACCC TCTCTCGGAG AAGGTCACCC GCGAGGTCGA CGGCTACTAC CTCCAGCACT GGCCCTTCCC 2100
GGACGAGCGC TCGCGCAAGA AGTTCGTCGC CGCGGGCTTC TCGCGCGTCA CCTGCTTCTA CTTCCCGAAG 2170
GCGCTCAACG ACCGCATCCA CTTCGCCTGC CGCCTCCTCA CCGTCCTCTT CCTCATCGAC GACCTCCTCG 2240
AGTACATGTC GCTCGAGGAC GGCAAGGCCT ACAACGAGAA GCTCATCCCG ATCTCGCGCG GCGACGTCCT 2310
CCCCGACCGC TCGGTCCCCG TCGAGTACAT CACGTACGAC CTCTGGGAGT CGATGCGCGC CCACGACCGC 2380
ATCATGGCGG ACGACATCCT CGAGCCCGTC TTCACGTTCA TGCGCGCCCA GACGGACTCG GTCCGCCTCG 2450
AGGCCATGGA CCTCGGCCGC TACCTCGAGT ACCGCGAGCG CGACGTCGGC AAGGCGCTCC TCGGCGCCCT 2520
CATGCGCTTC TCGATGGGCC TCGTCGTCCC GCCCGAGGAC CTCGCGATCG TCCGCCCCAT CGACTTCAAC 2590
TGCTCGCGCC ACCTCTCGGT CATCAACGAC ATCTGGTCGT TCGAGAAGGA GCTCCTCGCG TCAAGAACG 2660
CCCACGAGGA AGGCTGGCGTC CTCTGCTCGG CCGTCTCGGT CCTCGCCGAC CAGGTCGGCA TCTCGATCGA 2730
CGGCTCGAAG CGCATCCTCT ACTACCTCTG CCGCGAGTGG GAGCACCGCC ACGAGACGCT CGTCAAGGAG 2800
ATGCTCCAGG TCCGCGACAC GCCCGCCCTC CGCTCGTACG TCAAGGGCCT CGAGTACCAG ATGTCGGGCA 2870
ACGAGATGTG GTCGCGCACC ACCATGCGCT ACCTCGCCCC CAAGGACTGA ctgagcttct gtggaagagc 2940
cagtggtagt agcagtagca gcagcagtag cagccgcagc actcagtgtt ggcgcgagag attgtccatc 3010
ccttcttaac ctaccggaag agaaataagg cctttctccc gtagctgtct tcgtttgttt gtgctgattg 3080
cttggtatga gagtgttgaa tCtcctgcat catgttttc tctgtagtcc tttcctaccc ccgtcatttt 3150
cttttctccc tggttcttAC CCGTACACGC CCATGCTACA CCCTGCCTAC ACACGCGCAC ACGCGCACAA 3220
ACACACACAT ACATCAACAC ACACAATACA GCAATCCGTG CCTCTCTCTT ACTCTATTCA AGCGTGCTGC 3290
GTGGCCTTTG ACTTCATTCC TCTTGTCCAC CCGCCGGCCA CCAGTAGAAC CAGCACCACG TCCACCCTCA 3360
TCTCACTCCT CTTTCCCCCA CATCCCCTAC TACTCCATCC TTCTCATCTA CAGTCACACC TTCCTCCTCT 3430
TCACTTAACC ATGgtAAcca tggtAAGTTA CAAGCAGGAC GGAAGAGTGG ACTCAGATGG GAAAATACAA 3500
ATATTTATGA AGGTGCACAT TTAGATTGCG ACTTTTTCAT GACACAGAGA CACGTGGAGA TTTTCTTACT 3570
CCTCATCTCT GTGTCACTTA ATTTCTTTTT CATCCCTTTA CAACAGTGTT GGTGCGCTCA TCGACCGCAC 3640
ATCTACCTCG CACGCCACCC ATAACCTACC ACAGGCGGTG TTCAAGCCCG TGGCTGCATG CGTCGTCCCT 3710
TCCGCTACCA CCCCCGAGCT TGCACACGAT GGCGGCTCGC TCGTGAGTGG CTGGTGCAAG GCGAAAGCAA 3780
```

FIG. 7A

```
CCACAATATT CTGGCCTTTG CCATTTTATA TTGCCTGGCC TTGACCTTGT AAGCAGCGTC CCCACAGCTT 3850
CCTCCACCAG CACACTGTGT CCCGCATGTG TGGATTGGGG CAGTGGGCAG TCTTTCTTGT TGTCTTGCAC 3920
GCCCGCTGGA GGTCAAGTTG GATCAGTATT TGTACATGCA CGGAAGAGAG CGTGACGAGG CGGAGACAAA 3990
CCGCTCCAAG CCATCTTCCC ATACCAAGCA AACACAACAC GTACTCACCC TCCACTCTCC TTGTCCTTTT 4060
TCCCTCTGAC ACGCGCACCT ACAGCACCCC TCGACGACCC TCACCTGTCT AAATGGCCAA GTTGACCAGT 4130
GCCGTTCCGG TGCTCACCGC GCGCGACGTC GCCGGAGCGG TCGAGTTCTG GACCGACCGG CTCGGGTTCT 4200
CCCGGGACTT CGTGGAGGAC GACTTCGCCG GTGTGGTCCG GGACGACGTG ACCCTGTTCA TCAGCGCGGT 4270
CCAGGACCAG GTGGTGCCGG ACAACACCCT GGCCTGGGTG TGGGTGCGCG GCCTGGACGA GCTGTACGCC 4340
GAGTGGTCGG AGGTCGTGTC CACGAACTTC CGGGACGCCT CCGGGCCGGC CATGACCGAG ATCGGCGAGC 4410
AGCCGTGGGG GCGGGAGTTC GCCCTGCGCG ACCCGGCCGG CAACTGCGTG CACTTCGTGG CCGAGGAGCA 4480
GGACTAAATC TGTTAGTTGC AACAGTAGCA GCAACAGCTG TAGTTTTTGT ACGCGCAGTG CCTTGTGCTA 4550
GGAGGGAGTA GCAGTAGTAG TAGCAGCAGC AGCAGCAGCG ACAATTTTAT GTGTAAGGCG TGGTCCTTGT 4620
GTGCTTTGTG TCTGCTTTGT CTCTCGTGTG TCAAGAGGCA TTCGTAGGGA TTgtttaaac ctcgagtatA 4690
agcttggtgt aatcatggtc atagctgttt cctgtgtgaa attgttatcc gctcacaatt ccacacaaca 4760
tacgagccgg aagcataaag tgtaaagcct ggggtgccta atgagtgagc taactcacat taattgcgtt 4830
gcgctcactg cccgctttcc agtcgggaaa cctgtcgtgc cagctgcatt aatgaatcgg ccaacgcgcg 4900
gggagaggcg gtttgcgtat tgggcgctct tccgcttcct cgctcactga ctcgctgcgc tcggtcgttc 4970
ggctgcggcg agcggtatca gctcactcaa aggcggtaat acggttatcc acagaatcag gggataacgc 5040
aggaaagaac atgtgagcaa aaggccagca aaaggccagg aaccgtaaaa aggccgcgtt gctggcgttt 5110
ttccataggc tccgcccccc tgacgagcat cacaaaaatc gacgctcaag tcagaggtgg cgaaacccga 5180
caggactata aagataccag gcgtttcccc ctggaagctc cctcgtgcgc tctcctgttc cgaccctgcc 5250
gcttaccgga tacctgtccg cctttctccc ttcgggaagc gtggcgcttt ctcatagctc acgctgtagg 5320
tatctcagtt cggtgtaggt cgttcgctcc aagctgggct gtgtgcacga accccccgtt cagcccgacc 5390
gctgcgcctt atccggtaac tatcgtcttg agtccaaccc ggtaagacac gacttatcgc cactggcagc 5460
agccactggt aacaggatta gcagagcgag gtatgtaggc ggtgctacag agttcttgaa gtggtggcct 5530
aactacggct acactagaag aacagtattt ggtatctgcg ctctgctgaa gccagttacc ttcggaaaaa 5600
gagttggtag ctcttgatcc ggcaaacaaa ccaccgctgg tagcggtggt ttttttgttt gcaagcagca 5670
gattacgcgc agaaaaaaag gatctcaaga agatcctttg atcttttcta cggggtctga cgctcagtgg 5740
aacgaaaact cacgttaagg gattttggtc atgagattat caaaaaggat cttcacctag atccttttaa 5810
attaaaaatg aagttttaaa tcaagcccaa tctgaataat gttacaacca attaaccaat tctgattaga 5880
aaaactcatc gagcatcaaa tgaaactgca atttattcat atcaggatta tcaataccat attttttgaaa 5950
aagccgtttc tgtaatgaag gagaaaactc accgaggcag ttccatagga tggcaagatc ctggtatcgg 6020
tctgcgattc cgactcgtcc aacatcaata caacctatta atttcccctc gtcaaaaata aggttatcaa 6090
gtgagaaatc accatgagtg acgactgaat ccggtgagaa tggcaaaagt ttatgcattt ctttccagac 6160
ttgttcaaca ggccagccat tacgctcgtc atcaaaatca ctcgcatcaa ccaaaccgtt attcattcgt 6230
gattgcgcct gagcgagacg aaatacgcga tcgctgttaa aaggacaatt acaaacagga tcgaatgca 6300
accggcgcag gaacactgcc agcgcatcaa caatattttc acctgaatca ggatattctt ctaatacctg 6370
gaatgctgtt tttccgggga tcgcagtggt gagtaaccat gcatcatcag gagtacggat aaaatgcttg 6440
atggtcggaa gaggcataaa ttccgtcagc cagtttagtc tgaccatctc atctgtaaca tcattggcaa 6510
cgctaccttt gccatgtttc agaaacaact ctggcgcatc gggcttccca tacaagcgat agattgtcgc 6580
acctgattgc ccgacattat cgcgagccca tttatatccca tataaatcag catccatgtt ggaatttaat 6650
cgcggcctcg acgtttccg ttgaatatgg ctcataacac ccttgtatt actgtttatg taagcagaca 6720
gttttattgt tcatgatgat atattttat cttgtgcaat gtaacatcag agattttgag acacgggcca 6790
gagctgca 6798    (SEQ ID NO:20)
```

FIG. 7B

```
tcgcgcgttt cggtgatgac ggtgaaaacc tctgacacat gcagctcccg gagacggtca cagcttgtct  70
gtaagcggat gccgggagca gacaagcccg tcagggcgcg tcagcgggtg ttggcgggtg tcggggctgg 140
cttaactatg cggcatcaga gcagattgta ctgagagtgc accatatgcg gtgtgaaata ccgcacagat 210
gcgtaaggag aaaataccgc atcaggcgcc attcgccatt caggctgcgc aactgttggg aagggcgatc 280
ggtgcgggcc tcttcgctat tacgccagct ggcgaaaggg ggatgtgctg caaggcgatt aagttgggta 350
acgccagggt tttcccagtc acgacgttgt aaaacgacgg ccagagaatt cgtttaaacC AGTGGGATAA 420
AAGGCAGTCC GAAGGTTTCC GTCATCCTCG TCCTCGTTCT CGTTTTCCAC CTACTCATCT TCCGTTTCTT 490
GAGTGCGTCG CCGCTGGGTT TTCCTGAAAT AAACGCTCTT TCATATTATT TTTTTTCATC TTTTTTTCTT 560
CTATTGTTTT TTTTGACTTG TCTTTGACCT TGTCTGTAGC TCTTAACAGA TCAAAGGAAA AGCGAAGGCG 630
CCGCATGATC CTCGTCCTTC ACGAAACACA AACATCAGCC TCTTCACCCT CTTTCCCTGT TTCCTGCTAC 700
GAAATCGACA ACATTCAACA AGTCAGAAAC GCTCCTCTTC ACTAACACA CAATCGACCG CTGCTTTCCT 770
CCTTCCCTCC GCAGTAATCA ACACGTCTAT tctagaaatc TACATctagA CTTGAGAGAG TGGTGGAGTT 840
GACTATCGTG TGGAGTGTTT GGGGAGGGAA AGGGCGGAGC GTGAGTGCAA TGCGAGGTGG GCGAAGTGGG 910
CATGTGATAA ATGGCTGTGT GGTGGAGGCC TTCGCTGCGT GTCTGTGACT GTCTTGATTG TGTGCTTAGA 980
GTGAGATACC AAAGCAAGAT CTTCCCTGCC ATCCTTCAT TGTCCCACGG GCCGAAGAGA TGGGGGGCTT 1050
GACGAGAGGA CAGGGATGCA GGTGCGATGC GGTCCTGTCC tATGGGGCAG GAACCGCTGG GGTGCAGTGG 1120
CACAGAAGAC AGAAGGAGAA AACACATGCA CCAAATAAAC ATATGACAAA GAGTCAAGCA GTAGTCAAAA 1190
CAACCAAAAC GTAAGCAAGA CGGAACAAGA TGGCACGCT CTGCAACAGA CCGGCTGCGG CCGAACGTGC 1260
CTCCTGCTTT TCAACGATCC TGCGAGGTCA ACCAGGATTT GCTCGCCGGG ACGATTTCAT CCCCTTATCA 1330
ACGAGCCCTT GAGGCTCCAG GCGTGCTTCC ACACCCCAGT TGGTAACAGG ACATTGGGGC ATCTTGCCTA 1400
TCTTGTCTTA GTGCCGAAAG CCTCAACGAC CTCCtATGGG GTCTGCTCAA CGCCTCAACC TTGCAGTAAG 1470
GcATCCCCGA GGGCAAGACC CGCAAAGCCT TCTGTCGTCG GACAAAGCGG AGCGAGGGAA CAGGCTCAGC 1540
TCAACCCTCT TGAGAGCCCA TAAGTGCCCC CTGATCTATC TTCAACAGTC TTTCCCTGTC ACAAGAAAAC 1610
CCAGCTAGTT GACCAAGTTG CTAGAGCTGA TACCTTGTAC TTCGCTCTTT GTGTGCTTTA CCTGATTGGA 1680
CATGGACAGA CCTCCCCTTG CTCTTCCTTC TAGGAGCCTG GGCTCTCGCT CTTGTTCTTT CGAGAGACCT 1750
TTCCCTTGAG TTGCGTATCC AGCGATCAAG TATGAAGAGT GCTTCAAAC CTAGATACGT TCTGCCCAGT 1820
TCTCTTGCCC TTTTCCACAC GTGCTCCACA TCTTCACACG ACTCGCACCA TACCCGACGA AACCCCTCAA 1890
AACATCGCAA CACTTACATC CCGCTCGTGT CCCACCCCG ATGCCATATC CTCTACAGCA GCAGCACCAC 1960
CACCACCACT TCTTAAGtAT GGCCCCCATG GCGGAGGAGT GCGTCTCGGC GTCGCCCAAC CAGGGCCACG 2030
CCAAGCCCGT CGCCACCCCC ATGCGCCGCG CTGTCCACAT CCCCTCGTCG GAGTGGACCG CCCAGATCCA 2100
CCCTCTCCAC GAGAAGGTCA TCGCCGAGGT CGACGGCTAC TTCCTCCAGC ACTGGCCGTT CCCCTCGGAG 2170
AAGACCCGCA AGAAGTTCGT CGCCGCGGGC TTCTCGCGCG TCACCTGCCT CTACTTCCCG AAGGCGCTCG 2240
ACGACCGCAT CCACTTCGCC TGCCGCCTCC TCACCCTCCT CTTCCTCGTC GACGACATCC TCGAGCACAT 2310
GTCGCTCGAG GACGGCCGCG CTTACAACGA GCGCCTCATG CCTCTCTTCC GCGGCTCGGT CCTCCCCGAC 2380
CGCTCGGTCC CCGTCGAGTG GATCTCGTAC GACCTCTGGG AGTCGATGCG CGCCCACGAC CGCGACATGG 2450
CCGACGAGAT CATCGAGCCG GTCTTCACGT TCATGTGGGC CCAGACCGAC CCCGCCCGCC TCACCGAGAT 2520
GGGCCTCGGC CAGTACCTCG AGTACCGCGA GCGCGACGTC GGCAAGGCGC TCCTCGCCGC CCTCATGCGC 2590
TTCTCGATGG CCCTCATCGT CTCGCCCTCG GACCTCGAGA TGGTCCGCCC CGTCGACCGC AACTGCTCGA 2660
AGCACCTCTC GGTCATCAAC GACATCTGGT CGTACGAGAA GGAAGTCCTC GCCGCCCAGA CCCTCCACGA 2730
GGAAGGCGGC ATGCTCTGCA CCGCCGTCGC GGTCCTCTCG AAGGAAGCGG AGATCTCGAC CGACGCCTCG 2800
AAGCGCGTCC TCTACCACCT CTGCCGCGAG TGGGAGGACG AGCACCGCAT CCTCGTCGCC GACATCCTCG 2870
CCCAGAACGA CACCCCCGTC CTCCGCGCCT ACCTCCAGGG CCTCGAGTTC CAGATGTCGG GCAACGAGCT 2940
CTGGTCGCGC ACCACCCTCC GCTACGTCCA GCCTCGCCCG TGActgagct tctgtggaag agccagtggt 3010
agtagcagta gcagcagcag tagcagccgc agcactcagt gttggcgcga gagattgtcc atcccttctt 3080
aacctaccgg aagagaaata aggcctttct cccgtagctg tcttcgtttg tttgtgctga ttcttggta 3150
tgagagtgtt gaatCtcctg catcatgttt ttctctgtag tcctttccta ccccgtcat ttctttttct 3220
ccctggttct tACCCGTACA CGCCCATGCT ACACCCTGCC TACACACGCG CACACGCGCA CAAACACACA 3290
CATACATCAA CACACACAAT ACAGCAATCC GTGCCTCTCT CTTACTCTAT TCAAGCGTGC TGCGTGGCCT 3360
TTGACTTCAT TCCTCTTGTC CACCCGCCGG CCACCAGTAG AACCAGCACC ACGTCCACCC TCATCTCACT 3430
CCTCTTTCCC CCACATCCCC TACTACTCCA TCCTTCTCAT CTACAGTCAC ACCTTCCTCC TCTTCACTTA 3500
ACCATGgTAA ccatggtAAG TTACAAGCAG GACGGAAGAG TGGACTCAGA TGGGAAAATA CAAATATTTA 3570
TGAAGGTGCA CATTTAGATT GCGACTTTTT CATGACACAG AGACACGTGG AGATTTTCTT ACTCCTCATC 3640
TCTGTGTCAC TTAATTTCTT TTTCATCCCT TTACAACAGT GTTGGTGCGC TCATCGACCG CACATCTACC 3710
TCGCACGCCA CCCATAACCT ACCACAGGCG GTGTTCAAGC CCGTGGCTGC ATGCGTCGTC CCTTCCGCTA 3780
```

FIG. 8A

```
CCACCCCCGA GCTTGCACAC GATGGCGGCT CGCTCGTGAG TGGCTGGTGC AAGGCGAAAG CAACCACAAT 3850
ATTCTGGCCT TTGCCATTTT ATATTGCCTG GCCTTGACCT TGTAAGCAGC GTCCCCACAG CTTCCTCCAC 3920
CAGCACACTG TGTCCCGCAT GTGTGGATTG GGGCAGTGGG CAGTCTTTCT TGTTGTCTTG CACGCCCGCT 3990
GGAGGTCAAG TTGGATCAGT ATTTGTACAT GCACGGAAGA GAGCGTGACG AGGCGGAGAC AAACCGCTCC 4060
AAGCCATCTT CCCATACCAA GCAAACACAA CACGTACTCA CCCTCCACTC TCCTTGTCCT TTTTCCCTCT 4130
GACACGCGCA CCTACAGCAC CCCTCGACGA CCCTCACCTG TCTAAATGGC CAAGTTGACC AGTGCCGTTC 4200
CGGTGCTCAC CGCGCGCGAC GTCGCCGGAG CGGTCGAGTT CTGGACCGAC CGGCTCGGGT TCTCCCGGGA 4270
CTTCGTGGAG GACGACTTCG CCGGTGTGGT CCGGGACGAC GTGACCCTGT TCATCAGCGC GGTCCAGGAC 4340
CAGGTGGTGC CGGACAACAC CCTGGCCTGG GTGTGGGTGC GCGGCCTGGA CGAGCTGTAC GCCGAGTGGT 4410
CGGAGGTCGT GTCCACGAAC TTCCGGGACG CCTCCGGGCC GGCCATGACC GAGATCGGCG AGCAGCCGTG 4480
GGGGCGGGAG TTCGCCCTGC GCGACCCGGC CGGCAACTGC GTGCACTTCG TGGCCGAGGA GCAGGACTAA 4550
ATCTGTTAGT TGCAACAGTA GCAGCAACAG CTGTAGTTTT TGTACGCGCA GTGCCTTGTG CTAGGAGGGA 4620
GTAGCAGTAG TAGTAGCAGC AGCAGCAGCA GCGACAATTT TATGTGTAAG GCGTGGTCCT TGTGTGCTTT 4690
GTGTCTGCTT TGTCTCTCGT GTGTCAAGAG GCATTCGTAG GGATTgttta aacctcgagt atAagcttgg 4760
tgtaatcatg gtcatagctg tttcctgtgt gaaattgtta tccgctcaca attccacaca acatacgagc 4830
cggaagcata aagtgtaaag cctggggtgc ctaatgagtg agctaactca cattaattgc gttgcgctca 4900
ctgcccgctt tccagtcggg aaacctgtcg tgccagctgc attaatgaat cggccaacgc gcggggagag 4970
gcggtttgcg tattgggcgc tcttccgctt cctcgctcac tgactcgctg cgctcggtcg ttcggctgcg 5040
gcgagcggta tcagctcact caaaggcggt aatacggtta tccacagaat caggggataa cgcaggaaag 5110
aacatgtgag caaaaggcca gcaaaaggcc aggaaccgta aaaaggccgc gttgctggcg tttttccata 5180
ggctccgccc cctgacgag catcacaaaa atcgacgctc aagtcagagg tggcgaaacc cgacaggact 5250
ataaagatac caggcgtttc ccctggaag ctccctcgtg cgctctcctg ttccgaccct gccgcttacc 5320
ggatacctgt ccgcctttct cccttcggga agcgtggcgc tttctcatag ctcacgctgt aggtatctca 5390
gttcggtgta ggtcgttcgc tccaagctgg gctgtgtgca cgaaccccc gttcagcccg accgctgcgc 5460
cttatccggt aactatcgtc ttgagtccaa cccgtaaga cacgacttat cgccactggc agcagccact 5530
ggtaacagga ttagcagagc gaggtatgta ggcggtgcta cagagttctt gaagtggtgg cctaactacg 5600
gctacactag aagaacagta tttggtatct gcgctctgct gaagccagtt accttcggaa aaagagttgg 5670
tagctcttga tccggcaaac aaaccaccgc tggtagcggt ggttttttg tttgcaagca gcagattacg 5740
cgcagaaaaa aaggatctca agaagatcct ttgatctttt ctacggggtc tgacgctcag tggaacgaaa 5810
actcacgtta agggattttg gtcatgagat tatcaaaaag gatcttcacc tagatccttt taaattaaaa 5880
atgaagtttt aaatcaagcc caatctgaat aatgttacaa ccaattaacc aattctgatt agaaaaactc 5950
atcgagcatc aaatgaaact gcaatttatt catatcagga ttatcaatac catattttg aaaaagccgt 6020
ttctgtaatg aaggagaaaa ctcaccgagg cagttccata ggatggcaag atcctggtat cggtctgcga 6090
ttccgactcg tccaacatca atacaaccta ttaatttccc ctcgtcaaaa ataaggttat caagtgagaa 6160
atcaccatga gtgacgactg aatccggtga gaatggcaaa agtttatgca tttctttcca gacttgttca 6230
acaggccagc cattacgctc gtcatcaaaa tcactcgcat caaccaaacc gttattcatt cgtgattgcg 6300
cctgagcgag acgaaatacg cgatcgctgt taaaaggaca attacaaaca ggaatcgaat gcaaccggcg 6370
caggaacact gccagcgcat caacaatatt ttcacctgaa tcaggatatt cttctaatac ctggaatgct 6440
gttttccgg ggatcgcagt ggtgagtaac catgcatcat caggagtacg gataaaatgc ttgatggtcg 6510
gaagaggcat aaattccgtc agccagttta gtctgaccat ctcatctgta acatcattgg caacgctacc 6580
tttgccatgt ttcagaaaca actctggcgc atcgggcttc ccatacaagc gatagattgt cgcacctgat 6650
tgcccgacat tatcgcgagc ccatttatac ccatataaat cagcatccat gttggaattt aatcgcggcc 6720
tcgacgtttc ccgttgaata tggctcataa cacccttgt attactgttt atgtaagcag acagttttat 6790
tgttcatgat gatatatttt tatcttgtgc aatgtaacat cagagatttt gagacacggg ccagagctgc 6860
a 6861  (SEQ ID NO:21)
```

FIG. 8B

```
tcgcgcgttt cggtgatgac ggtgaaaacc tctgacacat gcagctcccg gagacggtca cagcttgtct   70
gtaagcggat gccgggagca gacaagcccg tcagggcgcg tcagcgggtg ttggcggtg tcggggctgg  140
cttaactatg cggcatcaga gcagattgta ctgagagtgc accatatgcg gtgtgaaata ccgcacagat  210
gcgtaaggag aaaataccgc atcaggcgcc attcgccatt caggctgcgc aactgttggg aagggcgatc  280
ggtgcgggcc tcttcgctat tacgccagct ggcgaaaggg ggatgtgctg caaggcgatt aagttgggta  350
acgccaggt tttcccagtc acgacgttgt aaaacgacgg ccagagaatt cgtttaaacC AGTGGGATAA  420
AAGGCAGTCC GAAGGTTTCC GTCATCCTCG TCCTCGTTCT CGTTTTCCAC CTACTCATCT TCCGTTTCTT  490
GAGTGCGTCG CCGCTGGGTT TTCCTGAAAT AAACGCTCTT TCATATTATT TTTTTCATC TTTTTTTCTT  560
CTATTGTTTT TTTTGACTTG TCTTTGACCT TGTCTGTAGC TCTTAACAGA TCAAAGGAAA AGCGAAGGCG  630
CCGCATGATC CTCGTCCTTC ACGAAACACA AACATCAGCC TCTTCACCCT CTTTCCCTGT TTCCTGCTAC  700
GAAATCGACA ACATTCAACA AGTCAGAAAC GCTCCTCTTC ACTAACACA CAATCGACCG CTGCTTTCCT  770
CCTTCCCTCC GCAGTAATCA ACACGTCTAT tctacttgta gagctcgtcc atgccgaggg tgatgccggc  840
ggcggtgacg aactcgagga ggaccatgtg gtcgcgcttc tcgttcgggt ccttcgagag ggccgactgg  910
gtcgagaggt agtggttgtc cgggaggagg accgggccgt cgccgatcgg ggtgttctgc tggtagtggt  980
cggcgagctg gaccgagccg tcctcgatgt tgtggcggat cttgaagttg accttgatgc cgttcttctg 1050
cttgtcggcc atgatgtaga cgttgtgcga gttgtagttg tactcgagct tgtggccgag gatgttccg 1120
tcctccttga agtcgatgcc cttgagctcg atgcggttga cgaggtgtc gccctcgaac ttgacctcgg 1190
cgcgggtctt gtagttgccg tcgtccttga agaagatggt gcgctcctgg acgtagccct ccggcatggc 1260
cgacttgaag aagtcgtgct gcttcatgtg gtccgggtag cgcgagaagc actggacgcc gtaggtgagg 1330
gtggtgacga gggtcggcca cgggaccggg agcttgccgg tggtgcagat gaacttgagg gtgagcttgc 1400
cgtaggtgcg gtcgccctcg ccctcgccg agaccgagaa cttgtggccg ttgacgtcgc cgtcgagctc 1470
gacgaggatc gggacgacgc cggtgaagag ctcctcgacc ttcgagacca taCTTGAGAG AGTGGTGGAG 1540
TTGACTATCG TGTGGAGTGT TTGGGGAGGG AAAGGGCGGA GCGTGAGTGG AATGCGAGGT GGGCGAAGTG 1610
GGCATGTGAT AAATGGCTGT GTGGTGGAGG CCTTCGCTGC GTGTCTGTGA CTGTCTTGAT TGTGTGCTTA 1680
GAGTGAGATA CCAAAGCAAG ATCTTCCCTG CCATCCCTTC ATTGTCCCAC GGGCCGAAGA GATGGGGGGC 1750
TTGACGAGAG GACAGGGATG CAGGTGCGAT GCGGTCCTGT CCtATGGGGC AGGAACCGCT GGGGTGCAGT 1820
GGCACAGAAG ACAGAAGGAG AAAACACATG CACCAAATAA ACATATGACA AAGAGTCAAG CAGTAGTCAA 1890
AACAACCAAA ACGTAAGCAA GACGGAACAA GATGGCACGC GTCTGCAACA GACCGGCTCG CGCCGAACGT 1960
GCCTCCTGCT TTTCAACGAT CCTGCGAGGT CAACCAGGAT TTGCTCGCCG GACGATTTC ATCCCCTTAT 2030
CAACGAGCCC TTGAGGCTCC AGGCGTGCTT CCACACCCCA GTTGGTAACA GGACATTGGG GCATCTTGCC 2100
TATCTTGTCT TAGTGCCGAA AGCCTCAACG ACCTCCtATG GGGTCTGCTC AACGCCTCAA CCTTGCAGTA 2170
AGGcATCCCC GAGGGCAAGA CCCGCAAAGC CTTCTGTCGT CGGACAAAGC GGAGCGAGGG AACAGGCTCA 2240
GCTCAACCCT CTTGAGAGCC CATAAGtGCC CCCTGATCtA TCTtCAACAG TCTTTCCCTG TCACAAGAAA 2310
ACCCAGCTAG TTGACCAAGT TGCTAGAGCT GATACCTTGT ACTTCGCTCT TTGTGTGCTT TACCTGATTG 2380
GACATGGACA GACCTCCCCT TGCTCTTCCT TCTAGGAGCC TGGGCTCTCG CTCTTGTTCT TTCGAGAGAC 2450
CTTTCCCTTG AGTTGCGTAT CCAGCGATCA AGTATGAAGA GTGCTTTCAA ACCTAGATAC GTTCTGCCCA 2520
GTTCTCTTGC CCTTTTCCAC ACGTGCTCCA CATCTTCACA CGACTCGCAC CATACCCGAC GAAACCCCTC 2590
AAAACATCGC AACACTTACA TCCCGCTCGT GTCCCACCCC CGATGCCATA TCCTCTACAG CAGCAGCACC 2660
ACCACCACCA CTTCTTAAGg atcctatagc tggatcctga gcttctgtgg aagagccagt ggtagtagca 2730
gtagcagcag cagtagcagc cgcagcactc agtgttggcg cgagagattg tccatccctt cttaacctac 2800
cggaagagaa ataaggcctt tctcccgtag ctgtcttcgt ttgtttgtgc tgattgcttg gtatgagagt 2870
gttgaatCtc ctgcatcatg tttttctctg tagtccttc ctaccccgt cattttcttt tctccctggt 2940
tcttACCCGT ACACGCCCAT GCTACACCCT GCCTACACAC GCGCACACGC GCACAAACAC ACACATACAT 3010
CAACACACAC AATACAGCAA TCCGTGCCTC TCTCTTACTC TATTCAAGCG TGCTGCGTGG CCTTTGACTT 3080
CATTCCTCTT GTCCACCCGC CGGCCACCAG TAGAACCAGC ACCACGTCCA CCCTCATCTC ACTCCTCTTT 3150
CCCCCACATC CCCTACTACT CCATCCTTCT CATCTACAGT CACACCTTCC TCCTCTTCAC TTAACCATGg 3220
TAAccatggt AAGTTACAAG CAGGACGGAA GAGTGGACTC AGATGGGAAA ATACAAATAT TTATGAAGGT 3290
GCACATTTAG ATTGCGACTT TTTCATGACA CAGAGACACG TGGAGATTTT CTTACTCCTC ATCTCTGTGT 3360
CACTTAATTT CTTTTTCATC CCTTTACAAC AGTGTTGGTG CGCTCATCGA CCGCACATCT ACCTCGACG 3430
CCACCCATAA CCTACCACAG GCGGTGTTCA AGCCGTGGC TGCATGCGTC GTCCCTTCCG CTACCACCCC 3500
CGAGCTTGCA CACGATGGCG GCTCGCTCGT GAGTGGCTGG TGCAAGGCGA AAGCAACCAC AATATTCTGG 3570
CCTTTGCCAT TTTATATTGC CTGGCCTTGA CCTTGTAAGC AGCGTCCCCA CAGCTTCCTC CACCAGCACA 3640
CTGTGTCCCG CATGTGTGGA TTGGGGCAGT GGGCAGTCTT TCTTGTTGTC TTGCACGCCC GCTGGAGGTC 3710
AAGTTGGATC AGTATTTGTA CATGCACGGA AGAGAGCGTG ACGAGGCGGA GACAAACCGC TCCAAGCCAT 3780
```

FIG. 9A

```
CTTCCCATAC CAAGCAAACA CAACACGTAC TCACCCTCCA CTCTCCTTGT CCTTTTTCCC TCTGACACGC 3850
GCACCTACAG CACCCCTCGA CGACCCTCAC CTGTCTAAAT GGCCAAGTTG ACCAGTGCCG TTCCGGTGCT 3920
CACCGCGCGC GACGTCGCCG GAGCGGTCGA GTTCTGGACC GACCGGCTCG GGTTCTCCCG GGACTTCGTG 3990
GAGGACGACT TCGCCGGTGT GGTCCGGGAC GACGTGACCC TGTTCATCAG CGCGGTCCAG GACCAGGTGG 4060
TGCCGGACAA CACCCTGGCC TGGGTGTGGG TGCGCGGCCT GGACGAGCTG TACGCCGAGT GGTCGGAGGT 4130
CGTGTCCACG AACTTCCGGG ACGCCTCCGG GCCGGCCATG ACCGAGATCG GCGAGCAGCC GTGGGGGCGG 4200
GAGTTCGCCC TGCGCGACCC GGCCGGCAAC TGCGTGCACT TCGTGGCCGA GGAGCAGGAC TAAATCTGTT 4270
AGTTGCAACA GTAGCAGCAA CAGCTGTAGT TTTTGTACGC GCAGTGCCTT GTGCTAGGAG GGAGTAGCAG 4340
TAGTAGTAGC AGCAGCAGCA GCAGCGACAA TTTTATGTGT AAGGCGTGGT CCTTGTGTGC TTTGTGTCTG 4410
CTTTGTCTCT CGTGTGTCAA GAGGCATTCG TAGGGATTgt ttaaacctcg agtatAagct tggtgtaatc 4480
atggtcatag ctgtttcctg tgtgaaattg ttatccgctc acaattccac acaacatacg agccggaagc 4550
ataaagtgta aagcctgggg tgcctaatga gtgagctaac tcacattaat tgcgttgcgc tcactgcccg 4620
ctttccagtc gggaaacctg tcgtgccagc tgcattaatg aatcggccaa cgcgcgggga gaggcggttt 4690
gcgtattggg cgctcttccg cttcctcgct cactgactcg ctgcgctcgg tcgttcggct gcggcgagcg 4760
gtatcagctc actcaaaggc ggtaatacgg ttatccacag aatcagggga taacgcagga agaacatgt 4830
gagcaaaagg ccagcaaaag gccaggaacc gtaaaaaggc cgcgttgctg gcgtttttcc ataggctccg 4900
ccccctgac gagcatcaca aaaatcgacg ctcaagtcag aggtggcgaa acccgacagg actataaaga 4970
taccaggcgt ttccccctgg aagctccctc gtgcgctctc ctgttccgac cctgccgctt accggatacc 5040
tgtccgcctt tctcccttcg ggaagcgtgg cgctttctca tagctcacgc tgtaggtatc tcagttcggt 5110
gtaggtcgtt cgctccaagc tgggctgtgt gcacgaaccc cccgttcagc ccgaccgctg cgccttatcc 5180
ggtaactatc gtcttgagtc caacccggta agacacgact tatcgccact ggcagcagcc actggtaaca 5250
ggattagcag agcgaggtat gtaggcggtg ctacagagtt cttgaagtgg tggcctaact acggctacac 5320
tagaagaaca gtatttggta tctgcgctct gctgaagcca gttaccttcg aaaaagagt tggtagctct 5390
tgatccggca aacaaaccac cgctggtagc ggtggttttt ttgtttgcaa gcagcagatt acgcgcagaa 5460
aaaaggatc tcaagaagat cctttgatct tttctacggg gtctgacgct cagtggaacg aaaactcacg 5530
ttaagggatt ttggtcatga gattatcaaa aaggatcttc acctagatcc ttttaaatta aaaatgaagt 5600
tttaaatcaa gcccaatctg aataatgtta caaccaatta accaattctg attagaaaaa ctcatcgagc 5670
atcaaatgaa actgcaattt attcatatca ggattatcaa taccatattt tgaaaaagc cgtttctgta 5740
atgaaggaga aaactcaccg aggcagttcc ataggatggc aagatcctgg tatcggtctg cgattccgac 5810
tcgtccaaca tcaatacaac ctattaattt ccctcgtca aaataaggt tatcaagtga gaaatcacca 5880
tgagtgacga ctgaatccgg tgagaatggc aaaagtttat gcatttcttt ccagacttgt tcaacaggcc 5950
agccattacg ctcgtcatca aaatcactcg catcaaccaa accgttattc attcgtgatt gcgcctgagc 6020
gagacgaaat acgcgatcgc tgttaaaagg acaattacaa acaggaatcg aatgcaaccg gcgcaggaac 6090
actgccagcg catcaacaat attttcacct gaatcaggat attcttctaa tacctggaat gctgttttc 6160
cggggatcgc agtggtgagt aaccatgcat catcaggagt acggataaaa tgcttgatgg tcgaagagg 6230
cataaattcc gtcagccagt ttagtctgac catctcatct gtaacatcat tggcaacgct acctttgcca 6300
tgtttcagaa acaactctgg cgcatcgggc ttcccataca agcgatagat tgtcgcacct gattgcccga 6370
cattatcgcg agcccattta tacccatata aatcagcatc catgttggaa tttaatcgcg gcctcgacgt 6440
ttcccgttga atatggctca taacacccct tgtattactg tttatgtaag cagacagttt tattgttcat 6510
gatgatatat ttttatcttg tgcaatgtaa catcagagat tttgagacac gggccagagc tgca 6574
(SEQ ID NO:22)
```

FIG. 9B

```
tcgcgcgttt cggtgatgac ggtgaaaacc tctgacacat gcagctcccg gagacggtca cagcttgtct  70
gtaagcggat gccgggagca gacaagcccg tcagggcgcg tcagcgggtg ttggcgggtg tcggggctgg 140
cttaactatg cggcatcaga gcagattgta ctgagagtgc accatatgcg gtgtgaaata ccgcacagat 210
gcgtaaggag aaaataccgc atcaggcgcc attcgccatt caggctgcgc aactgttggg aagggcgatc 280
ggtgcgggcc tcttcgctat tacgccagct ggcgaaaggg ggatgtgctg caaggcgatt aagttgggta 350
acgccaggt  tttcccagtc acgacgttgt aaaacgacgg ccagagaatt cgtttaaacC AGTGGGATAA 420
AAGGCAGTCC GAAGGTTTCC GTCATCCTCG TCCTCGTTCT CGTTTTCCAC CTACTCATCT TCCGTTTCTT 490
GAGTGCGTCG CCGCTGGGTT TTCCTGAAAT AAACGCTCTT TCATATTATT TTTTTTCATC TTTTTTTCTT 560
CTATTGTTTT TTTTGACTTG TCTTTGACCT TGTCTGTAGC TCTTAACAGA TCAAAGGAAA AGCGAAGGCG 630
CCGCATGATC CTCGTCCTTC ACGAAACACA AACATCAGCC TCTTCACCCT CTTTCCCTGT TTCCTGCTAC 700
GAAATCGACA ACATTCAACA AGTCAGAAAC GCTCCTCTTC ACTGAACACA CAATCGACCG CTGCTTTCCT 770
CCTTCCCTCC GCAGTAATCA ACACGTCTAT tctagaaatc TACATctagA CTTGAGAGAG TGGTGGAGTT 840
GACTATCGTG TGGAGTGTTT GGGGAGGGAA AGGGCGGAGC GTGAGTGCAA TGCGAGGTGG GCGAAGTGGG 910
CATGTGATAA ATGGCTGTGT GGTGGAGGCC TTCGCTGCGT GTCTGTGACT GTCTTGATTG TGCTTAGA 980
GTGAGATACC AAAGCAAGAT CTTCCCTGCC ATCCTTCAT TGTCCCACGG GCCGAAGAGA TGGGGGGCTT 1050
GACGAGAGGA CAGGGATGCA GGTGCGATGC GGTCCTGTCC tATGGGGCAG GAACCGCTGG GGTGCAGTGG 1120
CACAGAAGAC AGAAGGAGAA AACACATGCA CCAAATAAAC ATATGACAAA GAGTCAAGCA GTAGTCAAAA 1190
CAACCAAAAC GTAAGCAAGA CGGAACAAGA TGGCACGCGT CTGCAACAGA CCGGCTCGCG CCGAACGTGC 1260
CTCCTGCTTT TCAACGATCC TGCGAGGTCA ACCAGGATTT GCTCGCCGGG ACGATTTCAT CCCCTTATCA 1330
ACGAGCCCTT GAGGCTCCAG GCGTGCTTCC ACACCCCAGT TGGTAACAGG ACATTGGGGC ATCTTGCCTA 1400
TCTTGTCTTA GTGCCGAAAG CCTCAACGAC CTCCtATGGG GTCTGCTCAA CGCCTCAACC TTGCAGTAAG 1470
GcATCCCCGA GGGCAAGACC CGCAAAGCCT TCTGTCGTCG GACAAAGCGG AGCGAGGGAA CAGGCTCAGC 1540
TCAACCCTCT TGAGAGCCCA TAAGTGCCCC CTGATCTATC TTCAACAGTC TTTCCCTGTC ACAAGAAAAC 1610
CCAGCTAGTT GACCAAGTTG CTAGAGCTGA TACCTTGTAC TTCGCTCTTT GTGTGCTTTA CCTGATTGGA 1680
CATGGACAGA CCTCCCCTTG CTCTTCCTTC TAGGAGCCTG GGCTCTCGCT CTTGTTCTTT CGAGAGACCT 1750
TTCCCTTGAG TTGCGTATCC AGCGATCAAG TATGAAGAGT GCTTTCAAAC CTAGATACGT TCTGCCCAGT 1820
TCTCTTGCCC TTTTCCACAC GTGCTCCACA TCTTCACACG ACTCGCACCA TACCCGACGA AACCCCTCAA 1890
AACATCGCAA CACTTACATC CCGCTCGTGT CCCACCCCG ATGCCATATC CTCTACAGCA GCAGCACCAC 1960
CACCACCACT TCTTAAGgat cctatagctg gatcctgagc ttctgtggaa gagccagtgg tagtagcagt 2030
agcagcagca gtagcagccg cagcactcag tgttggcgcg agagattgtc catcccttct taacctaccg 2100
gaagagaaat aaggcctttc tccgtagct  gtcttcgttt gtttgtgctg attgcttggt atgagagtgt 2170
tgaatCtcct gcatcatgtt tttctctgta gtcctttcct accccgtca ttttcttttc tccctggttc 2240
ttACCCGTAC ACGCCATGC  TACACCCTGC CTACACACGC GCACACGCGC ACAAACACAC ACATACATCA 2310
ACACACACAA TACAGCAATC CGTGCCTCTC TCTTACTCTA TTCAAGCGTG CTGCGTGGCC TTTGACTTCA 2380
TTCCTCTTGT CCACCCGCCG GCCACCAGTA GAACCAGCAC CACGTCCACC CTCATCTCAC TCCTCTTTCC 2450
CCCACATCCC CTACTACTCC ATCCTTCTCA TCTACAGTCA CACCTTCCTC CTCTTCACTT AACCATGgTA 2520
AccatggtAA GTTACAAGCA GGACGGAAGA GTGGACTCAG ATGGGAAAAT ACAAATATTT ATGAAGGTGC 2590
ACATTTAGAT TGCGACTTTT TCATGACACA GAGACACGTG GAGATTTTCT TACTCCTCAT CTCTGTGTCA 2660
CTTAATTTCT TTTTCATCCC TTTACAACAG TGTTGGTGCG CTCATCGACC GCACATCTAC CTCGCACGCC 2730
ACCCATAACC TACCACAGGC GGTGTTCAAG CCCGTGGCTG CATGCGTCGT CCCTTCCGCT ACCACCCCG  2800
AGCTTGCACA CGATGGCGGC TCGCTCGTGA GTGGCTGGTG CAAGGCGAAA GCAACCACAA TATTCTGGCC 2870
TTTGCCATTT TATATTGCCT GGCCTTGACC TTGTAAGCAG CGTCCCCACA GCTTCCTCCA CCAGCACACT 2940
GTGTCCCGCA TGTGTGGATT GGGGCAGTGG GCAGTCTTTC TTGTTGTCTT GCACGCCCGC TGGAGGTCAA 3010
GTTGGATCAG TATTTGTACA TGCACGGAAG AGAGCGTGAC GAGGCGGAGA CAAACCGCTC CAAGCCATCT 3080
TCCCATACCA AGCAAACACA ACACGTACTC ACCCTCCACT CTCCTTGTCC TTTTTCCCTC TGACACGCGC 3150
ACCTACAGCA CCCCTCGACG ACCCTCACCT GTCTAAATGG CCAAGTTGAC CAGTGCCGTT CCGGTGCTCA 3220
CCGCGCGCGA CGTCGCCGGA GCGGTCGAGT CTGGACCGA  CCGGCTCGGG TTCTCCCGGG ACTTCGTGGA 3290
GGACGACTTC GCCGGTGTGG TCCGGGACGA CGTGACCCTG TTCATCAGCG CGGTCCAGGA CCAGGTGGTG 3360
CCGGACAACA CCCTGGCCTG GGTGTGGGTG CGCGGCCTGG ACGAGCTGTA CGCCGAGTGG TCGGAGGTCG 3430
TGTCCACGAA CTTCCGGGAC GCCTCCGGGC CGGCCATGAC CGAGATCGGC GAGCAGCCGT GGGGCGGGA  3500
GTTCGCCCTG CGCGACCCGG CCGGCAACTG CGTGCACTTC GTGGCCGAGG AGCAGGACTA AATCTGTTAG 3570
TTGCAACAGT AGCAGCAACA GCTGTAGTTT TTGTACGCGC AGTGCCTTGT GCTAGGAGGG AGTAGCAGTA 3640
GTAGTAGCAG CAGCAGCAGC AGCGACAATT TTATGTGTAA GGCGTGGTCC TTGTGTGCTT TGTGTCTGCT 3710
TTGTCTCTCG TGTGTCAAGA GGCATTCGTA GGGATTgttt aaacctcgag tatAagcttg gtgtaatcat 3780
```

FIG. 10A

```
ggtcatagct gtttcctgtg tgaaattgtt atccgctcac aattccacac aacatacgag ccggaagcat 3850
aaagtgtaaa gcctggggtg cctaatgagt gagctaactc acattaattg cgttgcgctc actgcccgct 3920
ttccagtcgg gaaacctgtc gtgccagctg cattaatgaa tcggccaacg cgcggggaga ggcggtttgc 3990
gtattgggcg ctcttccgct tcctcgctca ctgactcgct gcgctcggtc gttcggctgc ggcgagcggt 4060
atcagctcac tcaaaggcgg taatacggtt atccacagaa tcaggggata acgcaggaaa gaacatgtga 4130
gcaaaaggcc agcaaaaggc caggaaccgt aaaaaggccg cgttgctggc gtttttccat aggctccgcc 4200
ccctgacga gcatcacaaa aatcgacgct caagtcagag gtggcgaaac ccgacaggac tataaagata 4270
ccaggcgttt ccccctggaa gctccctcgt gcgctctcct gttccgaccc tgccgcttac cggatacctg 4340
tccgccttc tcccttcggg aagcgtggcg ctttctcata gctcacgctg taggtatctc agttcggtgt 4410
aggtcgttcg ctccaagctg ggctgtgtgc acgaacccc cgttcagccc gaccgctgcg ccttatccgg 4480
taactatcgt cttgagtcca acccggtaag acacgactta tcgccactgg cagcagccac tggtaacagg 4550
attagcagag cgaggtatgt aggcggtgct acagagttct tgaagtggtg gcctaactac ggctacacta 4620
gaagaacagt atttggtatc tgcgctctgc tgaagccagt taccttcgga aaaagagttg gtagctcttg 4690
atccggcaaa caaaccaccg ctggtagcgg tggttttttt gtttgcaagc agcagattac gcgcagaaaa 4760
aaaggatctc aagaagatcc tttgatcttt tctacggggt ctgacgctca gtggaacgaa aactcacgtt 4830
aagggatttt ggtcatgaga ttatcaaaaa ggatcttcac ctagatcctt ttaaattaaa aatgaagttt 4900
taaatcaagc ccaatctgaa taatgttaca accaattaac caattctgat tagaaaaact catcgagcat 4970
caaatgaaac tgcaatttat tcatatcagg attatcaata ccatatttt gaaaagccg tttctgtaat 5040
gaaggagaaa actcaccgag gcagttccat aggatggcaa gatcctggta tcggtctgcg attccgactc 5110
gtccaacatc aatacaacct attaatttcc cctcgtcaaa aataaggtta tcaagtgaga atcaccatg 5180
agtgacgact gaatccggtg agaatggcaa aagtttatgc atttctttcc agacttgttc aacaggccag 5250
ccattacgct cgtcatcaaa atcactcgca tcaaccaaac cgttattcat tcgtgattgc gcctgagcga 5320
gacgaaatac gcgatcgctg ttaaaaggac aattacaaac aggaatcgaa tgcaaccggc gcaggaacac 5390
tgccagcgca tcaacaatat tttcacctga atcaggatat tcttctaata cctggaatgc tgttttccg 5460
gggatcgcag tggtgagtaa ccatgcatca tcaggagtac ggataaaatg cttgatggtc ggaagaggca 5530
taaattccgt cagccagttt agtctgacca tctcatctgt aacatcattg gcaacgctac ctttgccatg 5600
tttcagaaac aactctggcg catcgggctt cccatacaag cgatagattg tcgcacctga ttgcccgaca 5670
ttatcgcgag cccatttata cccatataaa tcagcatcca tgttggaatt taatcgcggc ctcgacgttt 5740
cccgttgaat atggctcata cacccttg tattactgtt tatgtaagca gacagtttta ttgttcatga 5810
tgatatattt ttatcttgtg caatgtaaca tcagagattt tgagacacgg gccagagctg ca 5872
(SEQ ID NO:23)
```

CROP PROTECTION IN ALGAE BY EXOGENOUS TERPENE EXPRESSION

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD14795_ST25.txt," created on Jan. 20, 2021 (size of 84.6 kilobytes), which is hereby incorporated by reference in its entirety.

FIELD

The present disclosure relates to terpene synthases capable of producing terpenoids. In one instance, a transformed organism can include terpene synthases or vectors encoding such synthases. One method of employing such synthases and organisms includes protecting an algal culture, in which the produced terpenoid can act as a biocide.

BACKGROUND

Algae include a broad class of aquatic photoautotrophic organisms that can have high biomass yields per acre, as compared to terrestrial crops. For instance, algae can be grown using non-fresh water sources on non-arable land. Yet culturing algae can provide challenges, such as pond crash events that can drastically impact the economics and feasibility of large scale microalgae cultivation.

SUMMARY

The present disclosure relates to terpene synthases selected to produce terpenoid compounds using a genetically modified organism (e.g., a genetically modified algal cell). Such terpenoid compounds can have any useful purpose, such as for crop protection.

Accordingly, in a first aspect, the present disclosure encompasses a method of protecting an algal culture, the method including: introducing a terpenoid (e.g., a sesquiterpene) to an algal culture; and cultivating the algal culture in the presence of the terpenoid, thereby providing a stabilized culture.

In some embodiments, said introducing includes introducing a transformed organism to the algal culture, wherein the transformed organism includes an exogenous fungal terpene synthase or a nucleic acid encoding the exogenous fungal terpene synthase. In some embodiments, the transformed organism includes one exogenous fungal terpene synthase (or a nucleic acid encoding the synthase); two different exogenous fungal terpene synthases (or a nucleic acid encoding the two synthases, e.g., in a single plasmid or in separate plasmids); or three or more different exogenous fungal terpene synthases (or a nucleic acid encoding the three or more synthases, e.g., in a single plasmid or in separate plasmids). In particular embodiments, the transformed organism is configured to produce the terpenoid.

In some embodiments, the terpenoid includes any described herein. Non-limiting terpenoids (e.g., monoterpenes, sesquiterpenes, diterpenes, and/or triterpenes) include aristolochene, germacrene A, germacrene B, germacrene C, germacrene D, germacrene E, valencene, eudesmene, eudesmane, 4-epi-aristolochene, 5-epi-aristolochene, 4,5-di-epi-aristolochene, eremophilene, selinene, cadinene, α-cadinene, β-cadinene, γ-cadinene, δ-cadinene, muurolene, amorphene, and/or bulgarene, as well as others described herein.

In some embodiments, the stabilized culture is configured for crop protection and/or configured to be protected from a predator or a pond crash. In other embodiments, the stabilized culture produces the terpenoid configured to be a biocide (e.g., against a rotifer, protist, protozoa, or zooplankton).

In some embodiments, the stabilized culture includes a wild type algal cell and a transformed algal cell. In particular embodiments, the transformed algal cell includes an exogenous fungal terpene synthase (e.g., any described herein) or a nucleic acid encoding the exogenous fungal terpene synthase.

In other embodiments, the stabilized culture includes a wild type algal cell, a first transformed algal cell, and a second transformed algal cell. In particular embodiments, each of the first and second transformed algal cells includes a different exogenous fungal terpene synthase. In other embodiments, each of the first and second transformed algal cells includes a different nucleic acid encoding a different exogenous fungal terpene synthase.

In a second aspect, the present disclosure is an isolated, genetically engineered organism (e.g., a microbial organism or an alga) including: an exogenous fungal terpene synthase or a nucleic acid encoding the exogenous fungal terpene synthase. In some embodiments, the organism is configured to produce a terpenoid (e.g., any described herein).

In yet another aspect, the present disclosure relates to a method of protecting a crop, in which the method includes exposing the crop to one or more organisms (e.g., any described herein), thereby protecting the crop from one or more predators. In particular embodiments, the crop includes microalgae, and the predator includes a rotifer.

In any embodiment herein, the exogenous fungal terpene synthase includes a polypeptide sequence having at least 90% sequence identity to any one of SEQ ID Nos:1-8 and 10-18, as described herein.

In any embodiment herein, the nucleic acid encoding the exogenous fungal terpene synthase includes a nucleic acid sequence encoding a polypeptide sequence having at least 90% sequence identity to any one of SEQ ID NOs:1-8 and 10-18, as described herein.

In any embodiment herein, the exogenous fungal terpene synthase includes a polypeptide sequence having at least 90% sequence identity to LXDDXXEZ (SEQ ID NO:15) or a fragment thereof; where Z is any amino acid (e.g., D, E, N, Q, R, H, K, F, Y, or W); and where X is selected from the group consisting of G, A, V, I, and L. In other embodiments, the exogenous fungal terpene synthase includes a polypeptide sequence having at least 90% sequence identity to DDXXE (SEQ ID NO:16); where X is selected from the group consisting of G, A, V, I, and L.

In any embodiment herein, the exogenous fungal terpene synthase includes a polypeptide sequence having at least 90% sequence identity to XNDXXSXXKEXX (SEQ ID NO:17); where X is selected from the group consisting of G, A, V, I, L, D, E, M, F, Y, and W. In other embodiments, the exogenous fungal terpene synthase includes a polypeptide sequence having at least 90% sequence identity to NDXXSXXKE (SEQ ID NO:18); where X is selected from the group consisting of G, A, V, I, L, D, E, F, Y, and W.

In any embodiment herein, the exogenous fungal terpene synthase includes a polypeptide having at least 90% sequence identity to any one of SEQ ID NOs:1-8, as described herein.

In any embodiment herein, the nucleic acid encoding the exogenous fungal terpene synthase includes a nucleic acid sequence encoding a polypeptide sequence having at least 90% sequence identity to any one of SEQ ID NOs:1-8, as described herein.

In any embodiment herein, the nucleic acid encoding the exogenous fungal terpene synthase is provided as a plasmid vector.

In any embodiment herein, the exogenous terpene synthase includes a polypeptide sequence having at least 90% (e.g., 91%, 92%, 93%, 94%, 95%, 96%, 97%, 98%, 99%, or 99.9%) sequence identity to any polypeptide sequence described herein, or a fragment thereof (e.g., a fragment including 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more amino acids).

In any embodiment herein, the nucleic acid encoding the exogenous terpene synthase includes a nucleic acid sequence encoding a polypeptide sequence having at least 90% (e.g., 91%, 92%, 93%, 94%, 95%, 96%, 97%, 98%, 99%, or 99.9%) sequence identity to any polypeptide sequence described herein, or a complement thereof.

In any embodiment herein, the exogenous terpene synthase is a polypeptide sequence including any sequence described herein, e.g., in FIGS. 4A-4B or FIG. 5. In some embodiments, the nucleic acid encoding the exogenous enzyme, or a complement thereof is a nucleic acid sequence encoding any polypeptide sequence described herein (e.g., as in FIGS. 4A-4B or FIG. 5).

In any embodiment herein, the nucleic acid encoding the exogenous enzyme and/or the nucleic acid encoding the exogenous terpene synthase is provided as a plasmid vector (e.g., as in FIG. 6A-6D, 7A-7B, 8A-8B, 9A-9B, or 10A-10B).

In any embodiment herein, the organism is configured to produce one or more terpenoid compounds selected from the group consisting of a monoterpene, a sesquiterpene, and a diterpene. In other embodiments, the terpenoid compound is a compound shown in FIG. 1.

In any embodiment herein, the terpenoid compound is a compound shown in FIG. 1.

In any embodiment herein, the transformed organism or the isolated, genetically engineered organism further includes: an exogenous terpenoid precursor, an exogenous enzyme configured to synthesize a terpenoid precursor, or a nucleic acid encoding the exogenous enzyme. In some embodiments, the nucleic acid encoding the exogenous enzyme is provided as a plasmid vector.

In any embodiment herein, the exogenous terpenoid precursor includes dimethylallyl pyrophosphate, isopentenyl pyrophosphate, farnesyl diphosphate, geranyl pyrophosphate, or a salt thereof.

In any embodiment herein, the exogenous enzyme includes a farnesyl pyrophosphate synthase or a prenyl transferase. Other non-limiting exogenous enzymes include acetyl-CoA acetyltransferase, HMG-CoA synthase, HMG-CoA reductase, mevalonate kinase, phosphomevalonate kinase, mevalonate diphosphate decarboxylase, isoprenyl diphosphate isomerase, and geranyl pyrophosphate synthase.

In any embodiment herein, the organism is an algal cell; and the exogenous terpenoid precursor, exogenous enzyme, and/or exogenous terpene synthase, as well as nucleic acids thereof encoding the polypeptide or complements thereof, are derived from a fungus.

In any embodiment herein, the organism is configured to effectively degrade an endogenous terpenoid precursor or an exogenous terpenoid precursor, e.g., as compared to an organism lacking the exogenous enzyme configured to synthesize a terpenoid precursor and/or lacking the nucleic acid encoding the exogenous enzyme. Additional details follow.

Definitions

As used herein, the term "about" means+/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, complementary DNA (cDNA), DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with cytosine (C). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides), the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., J. Mol. Biol. 1990; 215:403-10; Zhang J et al., Genome Res. 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); a group of amino acids having heterocyclic chains consists of proline (Pro, P), histidine (His, H), and tryptophan (Trp, W); and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., J. Mol. Biol. 1981; 147:195-7) and BLAST (Basic Local Alignment Search Tool; Altschul S F et al., J. Mol. Biol. 1990; 215:403-10). These and other alignment algorithms are accessible using publicly available computer software such as "Best Fit" (Smith T F et al., Adv. Appl. Math. 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the disclosure will be apparent from the following description and the claims.

BRIEF DESCRIPTION OF THE DRAWINGS

FIGS. 4A-4B show polypeptide sequences for terpene synthases (TPSs). Provided are (A) various sequences (SEQ ID NOs:1-8) and (B) a comparison of sequences with a consensus sequence (SEQ ID NO:10). At each position, X in SEQ ID NO:10 can be an amino acid present at the aligned position in one of SEQ ID NOs:1-8.

FIG. 5 shows consensus sequences for TPSs. Provided are (A) consensus sequence 2A (SEQ ID NO:11) and a shorter consensus sequence 2B (SEQ ID NO:12); and (B) consensus sequence 3A (SEQ ID NO:13) and a shorter consensus sequence 3B (SEQ ID NO:14).

FIGS. 7A-7B show a non-limiting sequence for a vector including HypCI4A-322581 at location 1979-2924 in SEQ ID NO:20.

FIGS. 8A-8B show a non-limiting sequence for a vector including HypCO27-392541 at location 1979-2983 in SEQ ID NO:21.

FIGS. 9A-9B show a non-limiting sequence for a vector including GFP at location 802-1521 in SEQ ID NO:22.

FIGS. 10A-10B show a non-limiting sequence for a transformation vector including possible insertion sites at location 802-819, 1978-1994, and/or 2514-2525 in SEQ ID NO:23.

DETAILED DESCRIPTION

The present disclosure relates to terpene synthases capable of degrading precursors into terpenoid compounds. Such synthases can be provided by an isolated, genetically engineered organism. In one instance, the organism includes an exogenous terpene synthase (e.g., an exogenous endophytic fungal terpene synthase) or a nucleic acid encoding the exogenous terpene synthase.

As described herein, the terpenoid compound can serve as a biocide, which protects an algal culture from predation. Accordingly, the present disclosure relates to use of a terpenoid or a terpene synthase (or transformed organisms having the terpene synthase) within an algal culture. In some embodiments, the present disclosure encompasses methods of protecting an algal culture by introducing an isolated, genetically engineered organism to an algal culture, in which the organism is configured to provide or produce an exogenous terpene synthase. The methods can include other useful steps, including optionally treating the culture to one or more terpenoid compounds or terpenoid precursors. More than one type of terpene synthase, as well as more than one type of organism each independently including a synthase, can be employed within the method.

Figure 1:
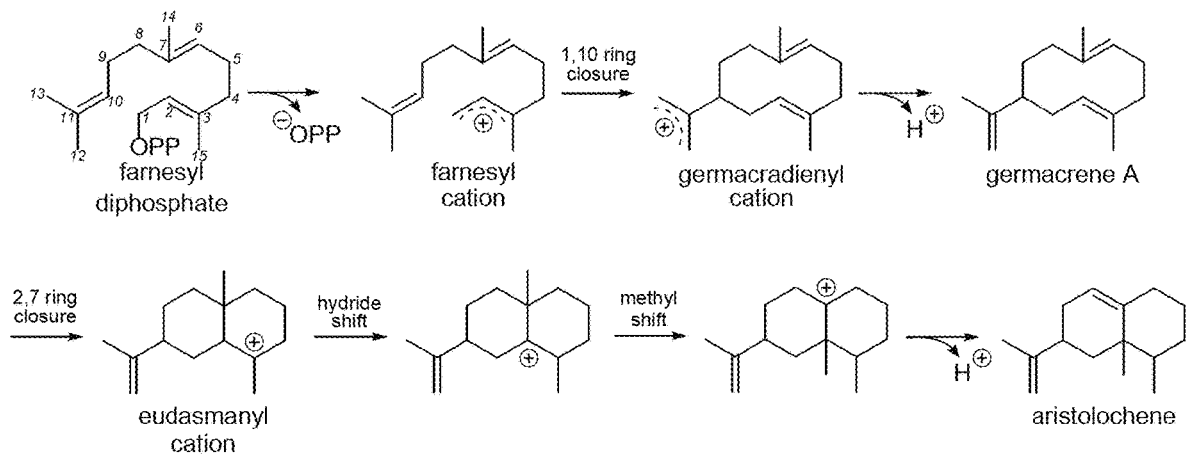
FIG. 1 shows a non-limiting schematic of a biosynthetic mechanism for providing aristolochene.

Such synthases can assist in the production of terpenoid compounds, such as monoterpenes, sesquiterpenes, diterpenes, and triterpenes by processing precursors. Exemplary terpenoid compounds include a monoterpene (e.g., a $C_{10}$ terpenoid compound or any such as camphene, carene, citral, citronellal, citronellol, halomon, limonene, linalool, myrcene, ocimene, phellandrene, pinene, sabinene, terpinene, terpinolene, and thujene), a sesquiterpene (e.g., a $C_{15}$ compound or any such as aristolochene, germacrene A, germacrene B, germacrene C, germacrene D, germacrene E, valencene, eudesmene, eudesmane, 4-epi-aristolochene, 5-epi-aristolochene, 4,5-di-epi-aristolochene, eremophilene, selinene, cadinene, α-cadinene, β-cadinene, γ-cadinene, δ-cadinene, muurolene, amorphene, bulgarene, caryophyllene, copaene, dictyophorine A, dictyophorine B, farnesene, farnesol, guaiazulene, humulene, longifolene, patchoulol, vetivazulene, and zingiberene, including bicyclic forms thereof), a diterpene (e.g., a $C_{20}$ compound or any such as abietane, cembrene A, labdane, phytane, sclarene, stemarene, stemodene, taxadiene, or taxane), or a triterpene (e.g., a $C_{30}$ compound or any such as hopane, lanostane, malabaricane, oleanane, polypodatetraene, or squalene), as well as salts thereof. Exemplary terpenoid precursors include mevalonic acid, dimethylallyl pyrophosphate, isopentenyl pyrophosphate, farnesyl diphosphate, geranyl pyrophosphate, or a salt thereof. Other exemplary terpenoid compounds and terpenoid precursors are provided in FIG. 1.

In particular instances, a combination of two or more different terpenoids is introduced to the algal culture. In some embodiments, the combination includes two or more different classes of terpenoids, such as a combination of a sesquiterpene with a monoterpene. In other embodiments, the combination includes a first organism configured to produce a first terpenoid and a second organism configured to produce a second terpenoid, wherein the first and second terpenoids are different. In yet other embodiments, the first and second terpenoids are from two different classes of terpenoids (e.g., a class of a sesquiterpene and a class of a monoterpene).

The terpene synthase can be identified in any useful manner. In one instance, naturally occurring terpene synthases can be screened to identify those that increase production of one or more terpenoid compounds (e.g., terpenoid compounds obtained by degrading a biomass, such as in the presence of one or more synthases). Exemplary synthases include those fungal terpene synthases (e.g., endophytic fungal terpene synthases, such as those for *Hypocreales* or *Xylariales*, including *Hypoxylon* and *Daldinia*). Exemplary terpene synthases are provided in FIGS. 4A-4B, as well as those motifs provided in FIG. 5.

In one embodiment, the exogenous fungal terpene synthase includes a polypeptide sequence having at least 90% sequence identity to the following:

(SEQ ID NO: 10)
$X_1X_2X_3X_4X_5X_6X_7HPX_{10}X_{11}X_{12}X_{13}VX_{15}X_{16}EX_{18}X_{19}X_{20}YX_{22}$ $X_{23}X_{24}X_{25}WX_{27}FPX_{30}X_{31}X_{32}X_{33}X_{34}X_{35}X_{36}FX_{38}X_{39}AX_{41}$ $FX_{43}X_{44}X_{45}TCX_{48}YFPX_{52}AX_{54}X_{55}DRIX_{59}FACRLLTX_{67}$

-continued

LFLX$_{71}$DDX$_{74}$LEX$_{77}$MSX$_{80}$X$_{81}$X$_{82}$GX$_{84}$AX$_{86}$NX$_{88}$X$_{89}$LX$_{91}$X$_{92}$

X$_{93}$X$_{94}$X$_{95}$GX$_{97}$X$_{98}$X$_{99}$X$_{100}$X$_{101}$PX$_{103}$X$_{104}$X$_{105}$X$_{106}$PX$_{108}$

X$_{109}$X$_{110}$X$_{111}$X$_{112}$X$_{113}$DLWX$_{117}$SMRX$_{121}$X$_{122}$DX$_{124}$X$_{125}$

X$_{126}$AX$_{128}$X$_{129}$X$_{130}$X$_{131}$EPX$_{134}$FX$_{136}$FMX$_{139}$X$_{140}$QTDX$_{144}$

X$_{145}$RX$_{147}$X$_{148}$X$_{149}$X$_{150}$X$_{151}$LGX$_{154}$YX$_{156}$X$_{157}$YRX$_{160}$X$_{161}$

DX$_{163}$GX$_{165}$X$_{166}$LLX$_{169}$ALMRX$_{174}$X$_{175}$X$_{176}$X$_{177}$X$_{178}$X$_{179}$

X$_{180}$X$_{181}$X$_{182}$X$_{183}$X$_{184}$LX$_{186}$X$_{187}$X$_{188}$X$_{189}$X$_{190}$X$_{191}$X$_{192}$

X$_{193}$NCX$_{196}$X$_{197}$X$_{198}$X$_{199}$X$_{200}$X$_{201}$X$_{202}$NDIX$_{206}$SX$_{208}$X$_{209}$

KEX$_{212}$X$_{213}$X$_{214}$X$_{215}$X$_{216}$X$_{217}$X$_{218}$HX$_{220}$EGX$_{223}$X$_{224}$

LCX$_{227}$X$_{228}$VX$_{230}$X$_{231}$X$_{232}$X$_{233}$X$_{234}$X$_{235}$X$_{236}$X$_{237}$X$_{238}$

X$_{239}$X$_{240}$X$_{241}$X$_{242}$X$_{243}$KRX$_{246}$LX$_{248}$X$_{249}$X$_{250}$X$_{251}$

REWEX$_{256}$X$_{257}$HX$_{259}$X$_{260}$X$_{261}$X$_{262}$X$_{263}$X$_{264}$X$_{265}$X$_{266}$X$_{267}$

X$_{268}$X$_{269}$X$_{270}$X$_{271}$X$_{272}$X$_{273}$X$_{274}$X$_{275}$X$_{276}$X$_{277}$X$_{278}$X$_{279}$

X$_{280}$X$_{281}$YX$_{283}$X$_{284}$GLX$_{287}$X$_{288}$QMSGNEX$_{295}$WSX$_{298}$X$_{299}$

TX$_{301}$RY, wherein:

$X_1$, $X_{43}$, $X_{105}$, or $X_{175}$ is C, S, or T;

$X_2$, $X_{11}$, $X_{193}$, $X_{234}$, $X_{237}$, $X_{249}$, $X_{256}$, $X_{260}$, or $X_{270}$ is any amino acid (e.g., G, A, V, I, L, D, E, R, H, K, C, S, T, N, Q, F, Y, W, P, M, or absent);

$X_3$, $X_{22}$, $X_{174}$, $X_{206}$, $X_{208}$, $X_{248}$, or $X_{288}$ is F, Y, or W;

$X_4$ or $X_{227}$ is C, S, T, N, or Q;

$X_5$, $X_{48}$, $X_{80}$, $X_{86}$, $X_{180}$, $X_{224}$, or $X_{261}$ is A, V, I, L, M, P, F, Y, or W;

$X_6$ or $X_{295}$ is A, V, I, L, M, N, or Q;

$X_7$, $X_{104}$, $X_{145}$, or $X_{179}$ is A, V, I, L, M, R, H, K, C, S, or T;

$X_{10}$, $X_{34}$, $X_{41}$, $X_{52}$, $X_{54}$, $X_{106}$, $X_{121}$, $X_{265}$, or $X_{301}$ is G, A, V, I, L, M, P, R, H, or K;

$X_{12}$, $X_{44}$, or $X_{157}$ is D, E, R, H, or K;

$X_{13}$, $X_{16}$, $X_{39}$, $X_{125}$, $X_{187}$, $X_{257}$, $X_{263}$, or $X_{264}$ is G, A, V, I, L, M, D, E, R, H, or K;

$X_{15}$, $X_{149}$, $X_{186}$, $X_{241}$, $X_{268}$, or $X_{281}$ is G, A, V, I, L, C, S, T, D, E, P, N, or Q;

$X_{18}$, $X_{33}$, $X_{45}$, $X_{101}$, $X_{112}$, $X_{134}$, $X_{136}$, $X_{140}$, $X_{169}$, $X_{196}$, $X_{200}$, $X_{214}$, $X_{215}$, $X_{223}$, $X_{228}$, $X_{233}$, $X_{236}$, $X_{239}$, $X_{240}$, $X_{242}$, $X_{243}$, $X_{251}$, $X_{262}$, $X_{272}$, $X_{278}$, $X_{283}$, or $X_{299}$ is G, A, V, I, L, M, C, S, or T;

$X_{19}$, $X_{20}$, $X_{55}$, $X_{88}$, $X_{103}$, $X_{109}$, $X_{117}$, $X_{128}$, $X_{129}$, $X_{192}$, $X_{235}$, or $X_{287}$ is G, D, E, N, or Q;

$X_{23}$, $X_{67}$, $X_{71}$, $X_{74}$, $X_{111}$, $X_{130}$, $X_{131}$, $X_{147}$, $X_{156}$, $X_{163}$, $X_{178}$, $X_{191}$, $X_{199}$, $X_{201}$, $X_{218}$, $X_{231}$, $X_{232}$, $X_{238}$, $X_{246}$, $X_{267}$, or $X_{279}$ is G, A, V, I, or L;

$X_{24}$ is A, V, I, L, D, E, N, or Q;

$X_{25}$, $X_{27}$, $X_{32}$, $X_{59}$, $X_{122}$, $X_{165}$, or $X_{198}$ is C, P, R, H, K, N, or Q;

$X_{30}$ is C, S, T, D, E, N, or Q;

$X_{31}$, $X_{190}$, or $X_{213}$ is A, V, I, L, D, E, P, F, Y, or W;

$X_{35}$, $X_{84}$, $X_{148}$, $X_{183}$, or $X_{220}$ is C, S, T, D, E, R, H, or K;

$X_{36}$, $X_{144}$, or $X_{181}$ is C, S, T, P, R, H, or K;

$X_{38}$, $X_{91}$, $X_{93}$, $X_{100}$, $X_{126}$, $X_{176}$, $X_{188}$, $X_{202}$, $X_{250}$, $X_{266}$, or $X_{267}$ is A, V, I, L, M, C, S, T, or absent;

$X_{77}$, $X_{139}$, or $X_{154}$ is G, D, E, N, Q, R, H, K, P, F, Y, or W;

$X_{81}$, $X_{108}$, $X_{166}$, $X_{177}$, or $X_{212}$ is G, A, V, I, L, D, or E;

$X_{82}$, $X_{160}$, $X_{184}$, $X_{209}$, or $X_{271}$ is G, D, or E;

$X_{89}$, $X_{95}$, $X_{161}$, or $X_{189}$ is R, H, or K;

$X_{92}$ or $X_{97}$ is C, S, T, D, E, P, F, Y, or W;

$X_{94}$ is A, V, I, L, C, S, T, P, F, Y, or W;

$X_{98}$ or $X_{99}$ is D, E, F, Y, W, or absent;

$X_{110}$ or $X_{113}$ is R, H, K, F, Y, or W;

$X_{124}$, $X_{182}$, $X_{197}$, or $X_{269}$ is G, A, V, I, L, P, R, H, K, N, or Q;

$X_{150}$ is C, M, R, H, or K;

$X_{151}$ is G, C, S, T, D, or E;

$X_{216}$ or $X_{230}$ is A, V, I, L, C, S, T, P, R, H, K, N, or Q;

$X_{217}$ or $X_{298}$ is C, S, T, P, R, H, K, N, or Q;

$X_{259}$ or $X_{284}$ is D, E, P, R, H, K, N, or Q;

$X_{273}$, $X_{274}$, $X_{275}$, $X_{276}$, or $X_{277}$ is G, C, S, T, N, Q, D, E, P, or absent; and $X_{280}$ is A, V, I, L, R, H, K, P, F, Y, or W.

The exogenous fungal terpene synthase can also be characterized by a consensus sequence that is an aspartate rich motif. In one embodiment, the exogenous fungal terpene synthase includes a polypeptide sequence having at least 90% sequence identity to the following:

LX$_1$DDX$_2$X$_3$EX$_4$ (SEQ ID NO:11), wherein:

$X_1$, $X_2$, or $X_3$ is A, V, I, or L; and $X_4$ is any amino acid (e.g., D, E, R, H, K, N, Q, P, F, Y, or W).

In another embodiment, the exogenous fungal terpene synthase includes a polypeptide sequence having at least 90% sequence identity to the following:

DDX$_1$X$_2$E (SEQ ID NO:12), wherein:

$X_1$ or $X_2$ is A, V, I, or L.

The exogenous fungal terpene synthase can also be characterized by a consensus sequence that is an NSE/DTE triad motif. In one embodiment, the exogenous fungal terpene synthase includes a polypeptide sequence having at least 90% sequence identity to the following:

X$_1$NDX$_2$X$_3$SX$_4$X$_5$KEX$_6$X$_7$ (SEQ ID NO:13), wherein:

$X_1$ is A, V, I, L, M, S, or T;

$X_2$ is A, V, I, or L (e.g., I);

$X_3$ or $X_4$ is F, Y, or W;

$X_5$ is D or E;

$X_6$ is A, V, I, L, D, or E; and $X_7$ is any amino acid (e.g., A, V, I, L, D, E, F, Y, or W).

In another embodiment, the exogenous fungal terpene synthase includes a polypeptide sequence having at least 90% sequence identity to the following:

NDX$_1$X$_2$SX$_3$X$_4$KE (SEQ ID NO:14), wherein:

$X_1$ is A, V, I, or L;

$X_2$ or $X_3$ is F, Y, or W; and $X_4$ is D or E.

The organism can also include proteins in one or more pathways that facilitate production of a terpenoid precursor. Thus, in some instances, the organism includes an exogenous terpenoid precursor, an exogenous enzyme configured to synthesize a terpenoid precursor, and/or a nucleic acid encoding the exogenous enzyme. The exogenous enzyme can include one or more in a mevalonate pathway and/or the 2-C-methyl-D-erythritol 4-phosphate/1-deoxy-D-xylulose 5-phosphate pathway (MEP/DOXP pathway). Exemplary exogenous enzymes include an acetoacetyl-CoA thiolase, 3-hydroxy-3-methyl-glutaryl-coenzyme A (HMG-CoA) synthase, HMG-CoA reductase, mevalonate-5-kinase, mevalonate-3-kinase, mevalonate-3-phosphate-5-kinase, phosphomevalonate kinase, mevalonate-5-pyrophosphate decarboxylase, isopentenyl pyrophosphate isomerase, DOXP synthase, 4-diphosphocytidyl-2-C-methyl-D-erythritol synthase, 4-diphosphocytidyl-2-C-methyl-D-erythritol kinase, 2-C-methyl-D-erythritol 2,4-cyclodiphosphate synthase, 4-hydroxy-3-methylbut-2-en-1-yl diphosphate (HMB-PP) synthase, and HMB-PP reductase.

The culture can include any useful organism, such as algae, chlorophytes, diatoms, plankton, protists, and/or cyanobacteria. For instance, algae can include one or more photosynthetic organisms, including one or more microalgae, macroalgae, diatoms, green algae, yellow algae, phytoplankton, haptophytes, and/or cyanobacteria. Exemplary algae include *Achnanthes, Ankistrodesmus* (e.g., *A. falcatus* or *A. fusiformis*), *Aphanizomenon, Arthrospira* (e.g., *A. maxima*), *Bacillariophyceae, Botryococcus* (e.g., *B. braunii*), *Chlamydocapsa* (e.g., *C. bacillus*), *Chlamydomonas* (e.g., *C. perigranulata* or *C. reinhardtii*), *Chlorella* (e.g., *C. marina, C. vulgaris, C. sorokiniana, C. minutissima,* or *C. pyrenoidosa*), *Chlorococcum* (e.g., *C. infusionum, C. littorals*, or *C. humicola*), *Chlorogloeopsis* (e.g., *C. fritschii*), *Chlorophyceae, Chrysophyceae, Cyanophyceae, Dunaliella* (e.g., *D. bardawil, D. bioculata, D. primolecta, D. tertiolecta,* or *D. salina*), *Ellipsoidion, Isochrysis, Kirchneriella* (e.g., *K. lunaris*), *Nannochloropsis* (e.g., *N. salina* or *N. oculata*), *Neochloris* (e.g., *N. oleoabundans*), *Nitzschia, Phaeodactylum* (e.g., *P. tricornutum*), *Porphyridium* (e.g., *P. purpureum*), *Pyrmnesium* (e.g., *P. parvum*), *Scenedesmus* (e.g., *S. obliquus, S. quadricauda,* or *S. dimorphus*), *Schizochytrium, Skeletonema* (e.g., *S. costatum*), *Spirogyra, Spirulina* (e.g., *S. maxima* or *S. platensis*), *Synechococcus* (e.g., *S. elongatus*), and/or *Tetraselmis* (e.g., *T. maculata* or *T. suecica*). Additional algae species and organisms are described in Schneider R C S et al., "Potential production of biofuel from microalgae biomass produced in wastewater," in Biodiesel—Feedstocks, Production and Applications, Prof. Zhen Fang (ed.), InTech, 2012, 22 pp., which is incorporated herein by reference in its entirety.

The algal culture or the stabilized culture can be used in any useful manner. In one instance, the culture or a product thereof is employed to produce biofuels, chemical intermediates, amino acids, nutrients, animal feed (e.g., fish feed), fertilizer, glycerine, biopolymers, and others.

Methods

The present disclosure includes any use of the terpene synthases or transformed organisms described herein. Such use can include a method of protecting an algal culture (e.g., any described herein) by introducing a terpenoid to the culture. The terpenoid can be provided as a chemical compound (e.g., any terpenoid compound or terpenoid precursor, as described herein) or provided as an organism producing that compound.

Culturing in the presence of terpenoid (e.g., as a compound or a transformed organism) can provide a stabilized culture. In one instance, the terpenoid provides a biocidal effect that provides protection against pond crash events or predation (e.g., by a microorganism, such as a rotifer, protist, protozoa, or zooplankton). In some non-limiting instances, a terpenoid precursor can be provided to the culture, thereby increasing the precursor concentration for conversion into the terpenoid.

The stabilized culture can include non-transformed and transformed organisms. For instance, the culture can include non-transformed, wild type algal cells and transformed algal cells. Transformed cells can be produced in any useful manner, such as electroporation, particle bombardment, *Agrobacterium tumefaciens*-mediated transformation, conjugation, and methods involving glass beads and carbon whiskers.

Figure 6A:
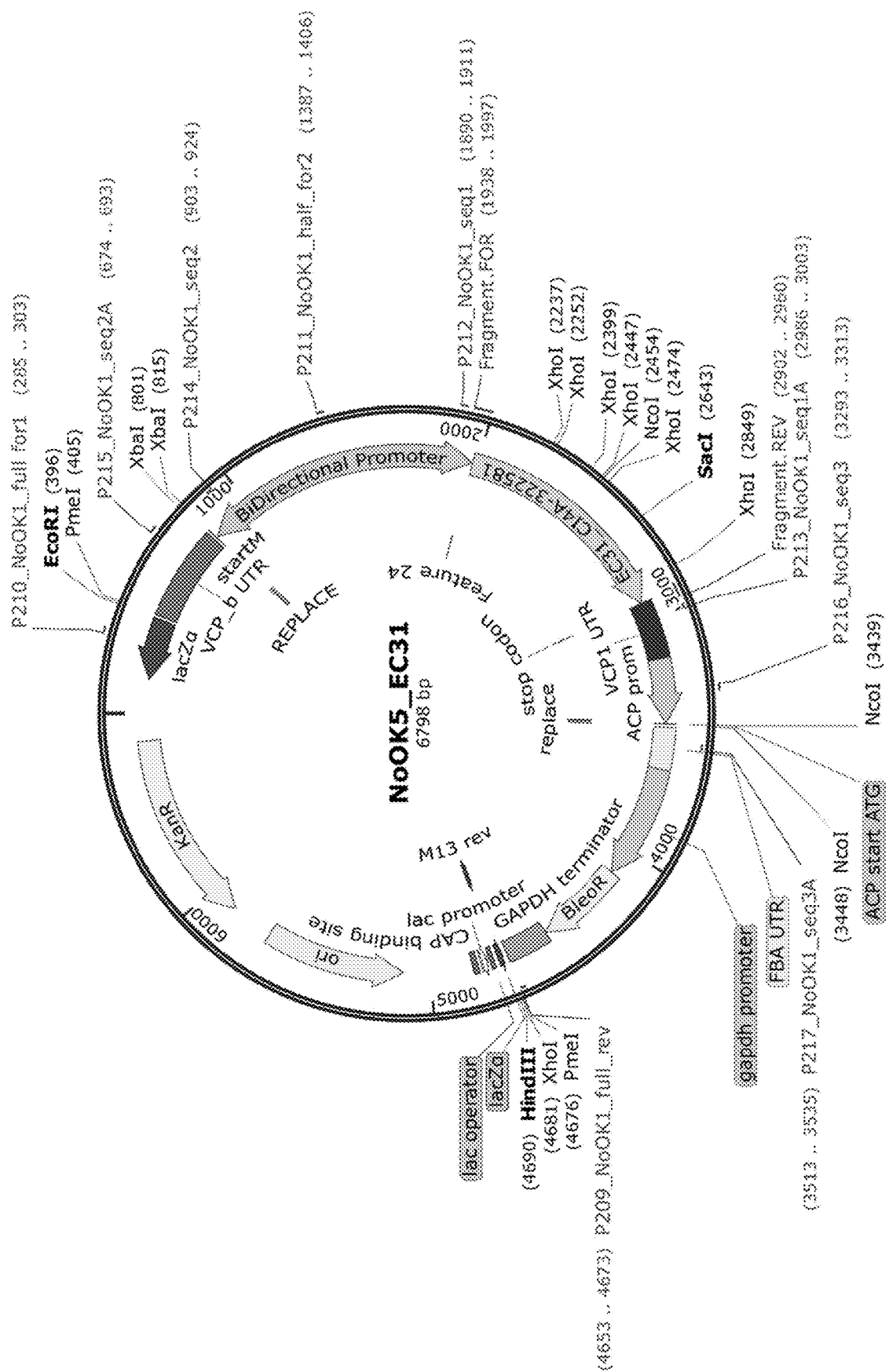
FIGS. 6A-6D show non-limiting plasmid maps for (A) a vector including HypCI4A-322581; (B) a vector including HypCO27-392541; (C) a vector including green fluorescent protein (GFP); and (D) a transformation vector for *Nannochloropsis*, in which one or more synthases can be expressed using this vector.
Figure 6B:
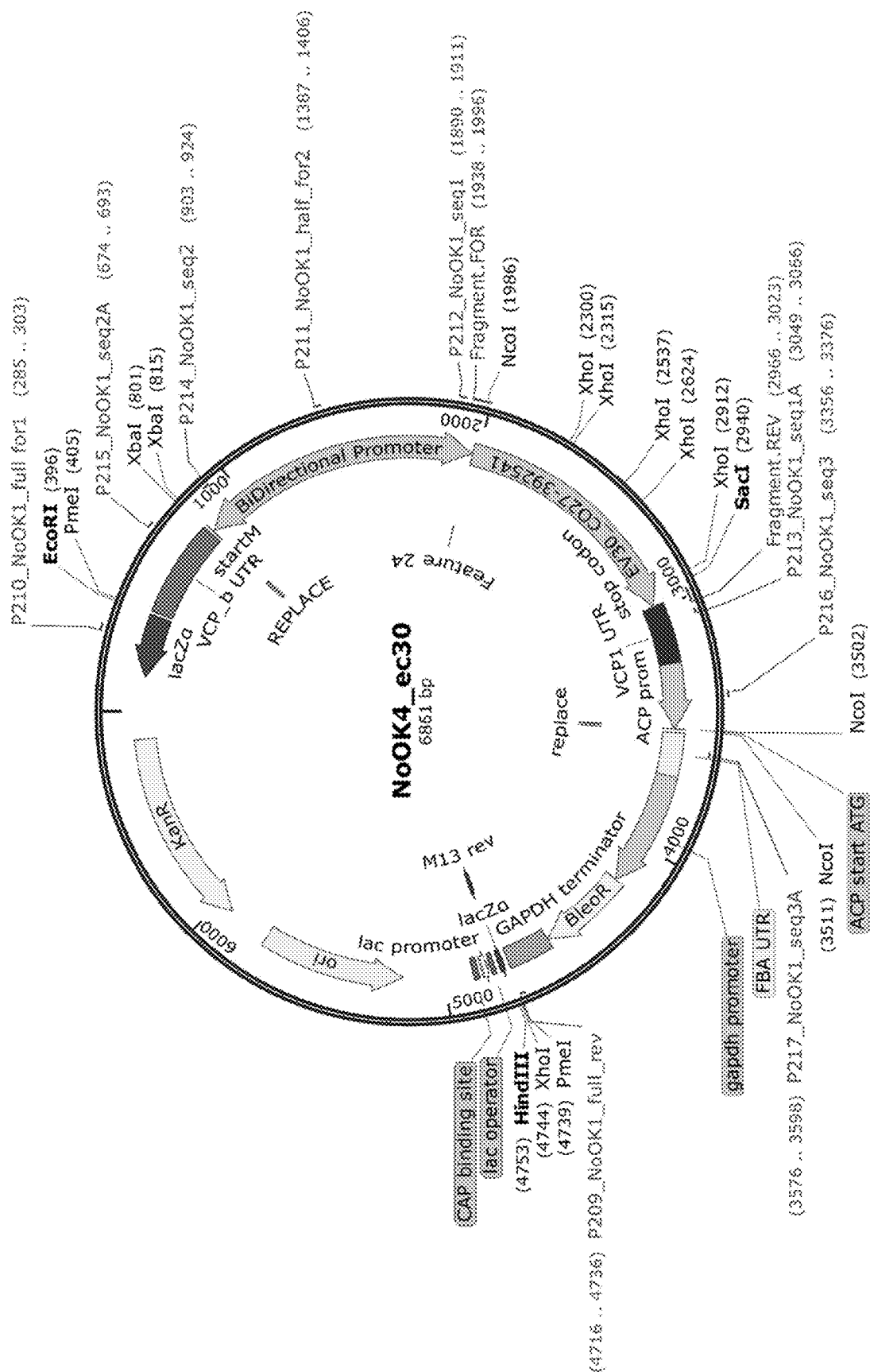
Figure 6C:
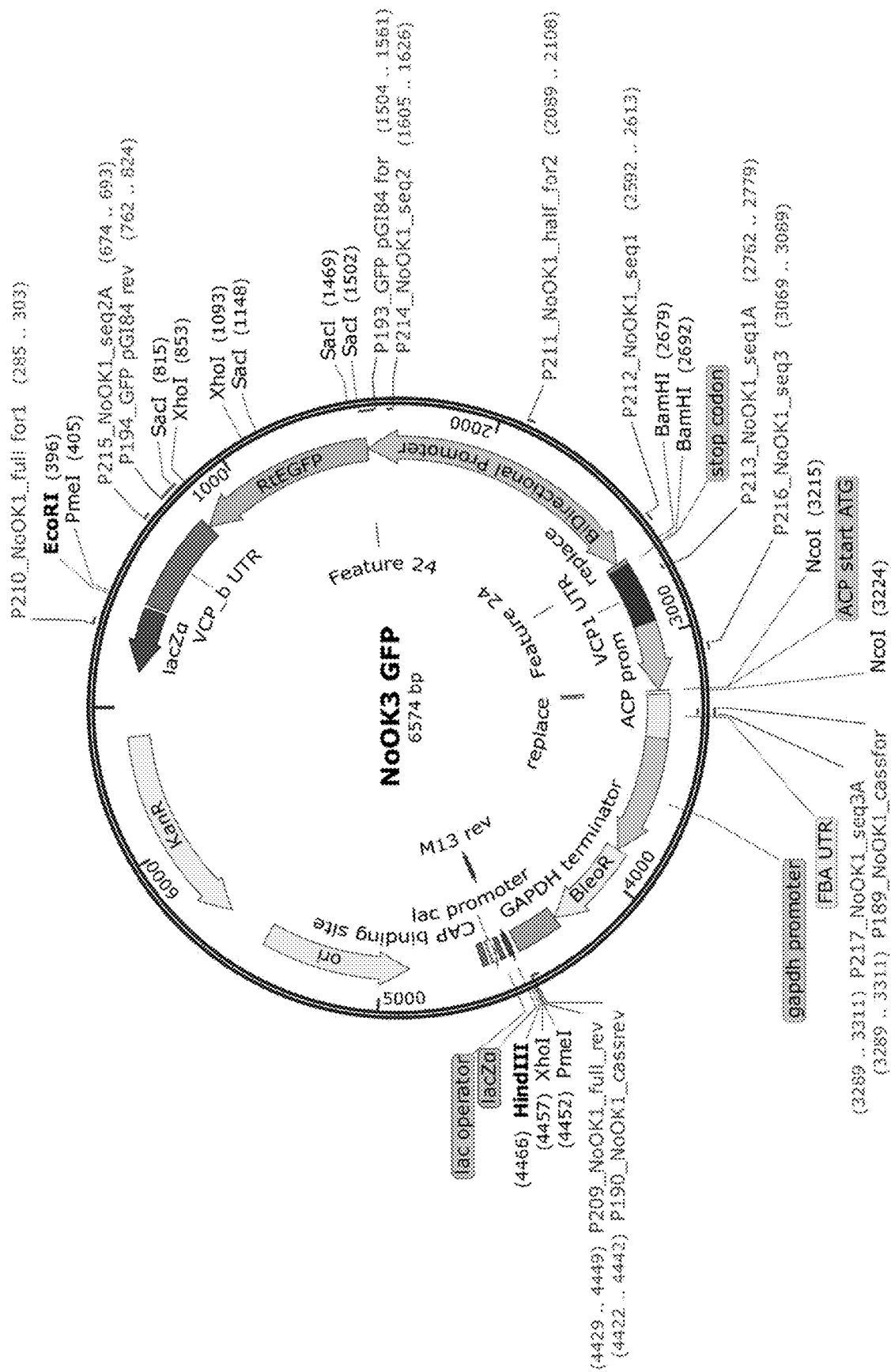
Figure 6D:
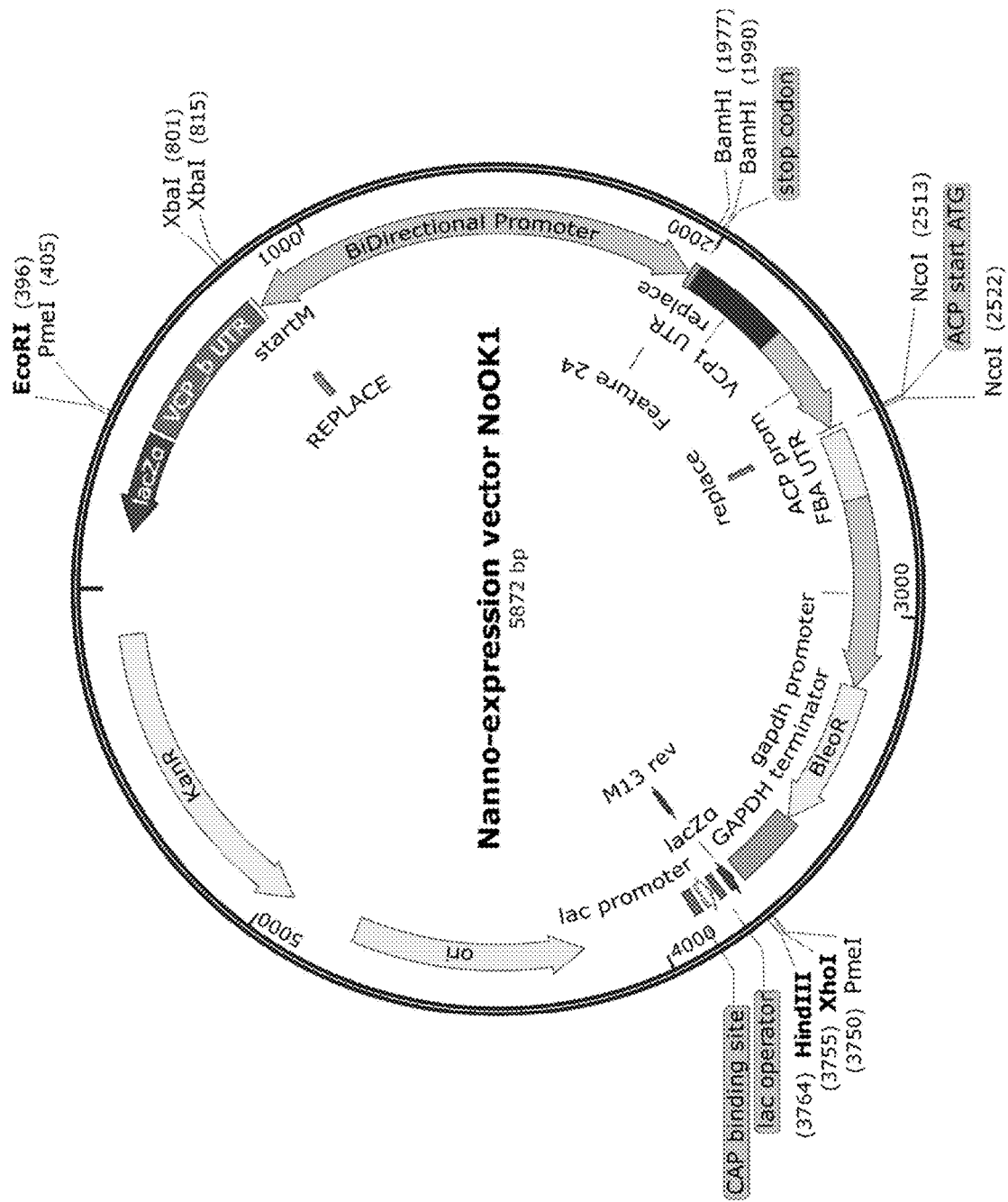

The transformed organism or cell can include the use of a plasmid vector. Non-limiting vectors are provided in FIGS. 6A-6D, in which non-limiting sequences for vectors can include any in FIGS. 7A-7B, 8A-8B, 9A-9B, and 10A-10B. Of note, FIG. 6D shows a transformation vector that can allow for up to three simultaneous expressed genes to be inserted. Bleomycin resistance protein from *Streptoalloteichus hindustanus* (Sh ble) is the selection marker. This vector can be designed for Gibson insertions (e.g., at insertion location 802-819 in SEQ ID NO:23; at insertion location 1978-1994 in SEQ ID NO:23; and/or at insertion location 2514-2525 in SEQ ID NO:23), in which software confirmation confirms use of the Gibson strategy to provide desired insertions (e.g., at boundaries ATG .- - -. TAA (or TGA as stop), in which - - - provides the gene sequence. The vector can include other constructs designed and optimized for other functionalities, e.g., for fusion PCR cloning and/or for removable selection cassettes.

EXAMPLES

Example 1: Crop Protection in Microalgae by Terpene Expression

Transformation vectors were produced and introduced into the microalgae *Nannochloropsis oceanica* (*N. oceanica*) by electroporation for transgenic production of endophytic sesquiterpenes. Gas chromatography-mass spectrometry (GC-MS) analysis of the culture medium for the genetically transformed *N. oceanica* indicated the presence of sesquiterpene products. The primary product was indicated to be aristolochene, which significantly increased predation resistance at rotifer concentrations between 10-50/mL.

Cultivation assays of *N. oceanica* in the presence of rotifers, which are common algae grazers and culture-crash inducing agents, indicate up to 50% increased survival of the sesquiterpene producing cultures over controls, indicating potential for algae crop-protection applications. Additional details follow.

Example 2: Experimental Methods

The following provides non-limiting transformation protocols of *N. oceanica*. In particular, an electroporation protocol can be used to transform *N. oceanica* with an antibiotic resistance and terpene synthase-containing plasmid (e.g., see FIGS. 6A-6B). Culture media (F2N, at 50% salt) were inoculated with *N. oceanica* and allowed to grow to stationary phase. Algal cells were pelleted (5 minutes at 4000 rpm and 4° C.), washed (with 2 mL 1 M sorbitol), and kept on ice for the rest of the procedure. The sorbitol and pellet solutions were split into multiple aliquots, and cells were pelleted. Then, the pellet was washed (four times with ice cold 1 M sorbitol), and the supernatant was removed after the fourth wash (~25 μL wet cells in each tube). Each tube was brought to a 50 μL volume with ice cold 1 M sorbitol, and DNA to be transformed into algae (200-500 ng) was added to cells and mixed.

Plasmids included those containing terpene synthase or GFP, zeocin resistance, and kanamycin resistance, which were delivered via electroporation. Immediately after electroporation, cells were resuspended (with a 1:1 mixture of cold F2N 50% salt: 1M sorbitol), put back on ice, and incubated overnight. The culture was then pelleted, washed, and then plated on F2N agar plates with zeocin or another antibiotic marker. Colonies were replated onto agar plates and then grown, as desired. The translated GFP sequence was as follows:

(SEQ ID NO: 24)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

-continued

VYIMADKQKNGIKVNFKIRHNIEDGSVQLADHYQQNTPIGDGPVLLPDNH

YLSTQSALSKDPNEKRDHMVLLEFVTAAGITLGMDELYK*.

Solid phase microextraction (SPME) and GC-MS analysis were employed to measure volatile organic carbon (VOC) signatures in algal samples. For instance, SPME columns were exposed to 3 mL of cultures grown on a well plate or in a flask. Resultant analysis by GC-MS provided elution peaks, in which terpenes generally eluted at about 12.7-12.9 minutes.

Example 3: Pond Crash Prevention by Terpene Production in N. oceanica

Microalgae cultivation has long been considered a promising technology with high biomass yield and minimal use of resources, such as fresh water and arable land. Furthermore, microalgae can be readily converted into a variety of biofuels including diesel, jet, and spark ignition fuels with limited processing requirements making microalgae a very promising technology for a renewable and domestic fuel source. While much progress has been made in discovering new strains and cultivation strategies to increase yields and lower costs, there has been limited progress in understanding and limiting pond crash events. There are estimates that about 20% of all large scale outdoor cultures will result in a crash, which has drastic impacts on the economics and feasibility of large scale microalgae cultivation.

Many strategies for crop protection have been explored, each with varying degrees of success. Pond crashes remain a significant hurdle for widespread and cost-competitive algal cultivation in open raceway ponds. Described herein are genetically engineered, saltwater algae strains for sesquiterpene production to act as a biocide against the diverse suite of natural predators and competition in open raceway ponds.

Figure 2:
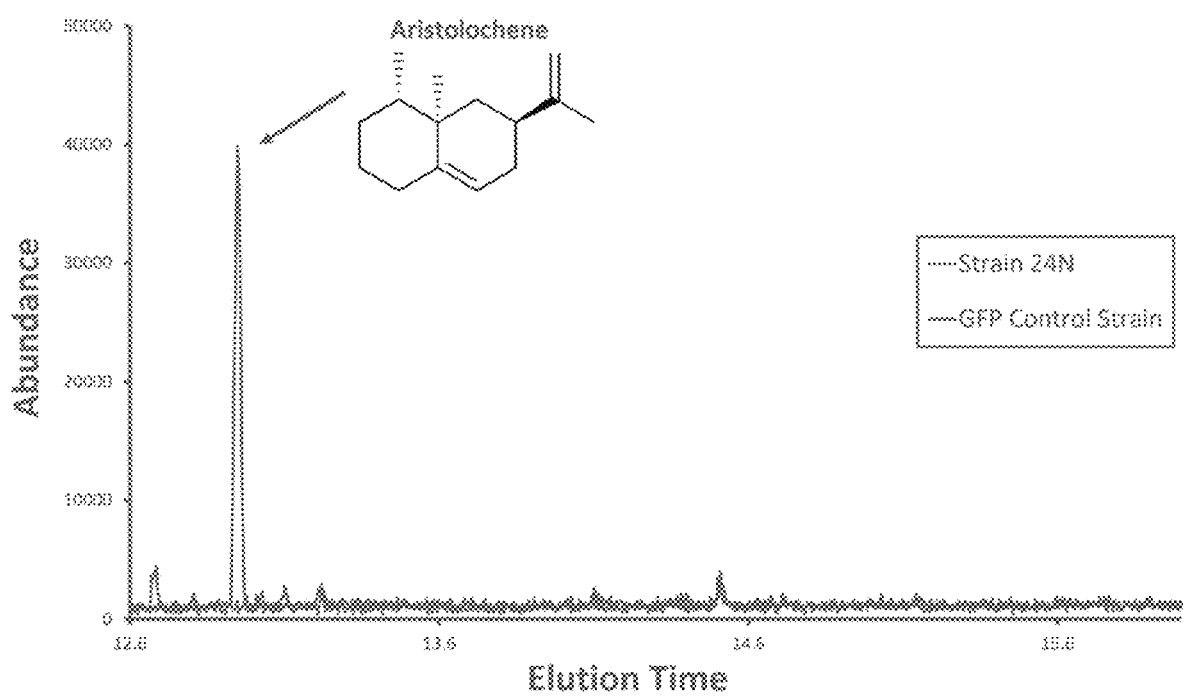
FIG. 2 shows a gas chromatograph terpene profile for strain 24N and a control strain (expressing green fluorescent protein, GFP). The identified peak shows the presence of aristolochene for strain 24N expressing an exogenous terpene synthase.

Algae strains were tested for volatile compounds via the manual SPME injection method for gas chromatography. In particular, culture 24N produced the highest concentration of terpenes (FIG. 2), and the terpene produced by this particular strain was aristolochene. In comparison, the strain that was transformed with the control gene for GFP did not produce a detectable concentration of terpenes.

Figure 3A:
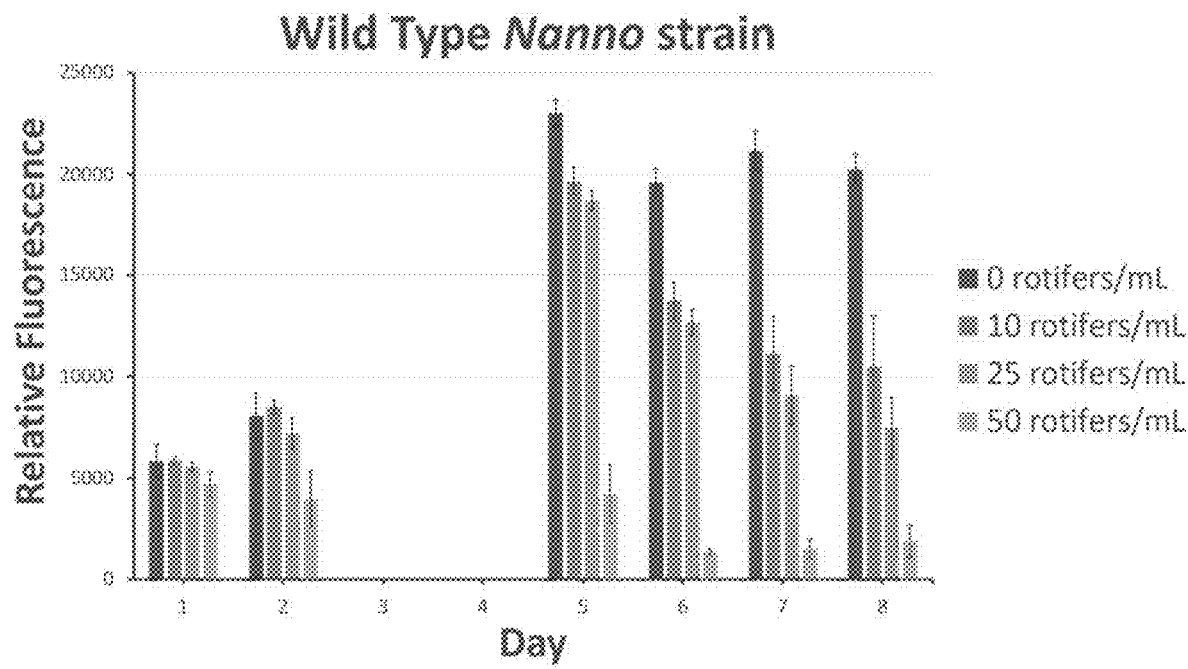
FIGS. 3A-3B show culture stability in the presence of predation by rotifers. Provided are graphs showing (A) a culture including wild type *Nannochloropsis oceanica* (*N. oceanica*) exposed to increasing *Brachionus plicatilis* (rotifers) concentrations and (B) a transformed culture including *N. oceanica* strain 24N having a HypCI4A-322581 (*Hypoxylon* sp. CI-4A, sesquiterpene synthase) gene.
Figure 3B:
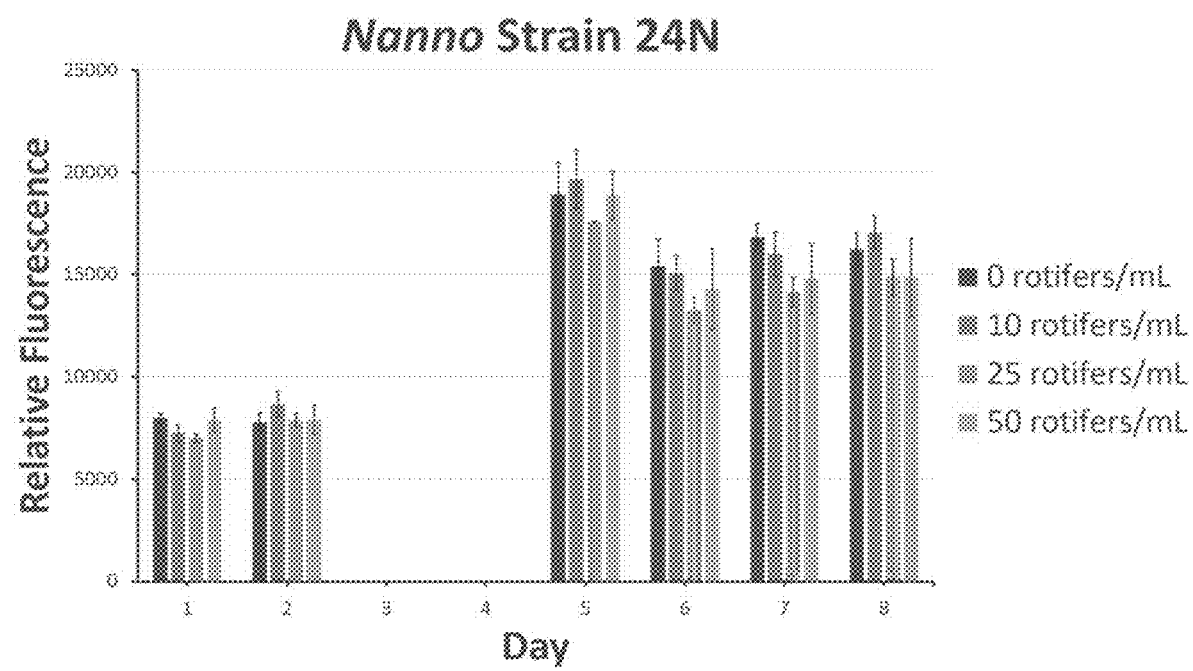

FIGS. 3A-3B show culture stability against predation. The strain that was not subject to transformation was severely inhibited by increasing *Brachionus plicatilis* (rotifers) concentrations until eventual crash (FIG. 3A). In contrast, the terpene-producing strain 24N was not significantly inhibited by predators (FIG. 3B).

FIGS. 4A-4B and FIG. 5 show non-limiting sequences for a terpene synthase, and FIGS. 6A-6D show non-limiting plasmids for the insertion of a gene into *Nannochloropsis* species of haploid containing microalgae. Specifically, the species was *N. oceanica* with two different sesquiterpene synthases that were cloned and electroporated into the genome.

As described herein, the *N. oceanica* genome was successfully transformed to provide an organism that produces a terpene. The algae is more susceptible to pond crashes if the *Brachionus plicatilis* (rotifer) concentration is allowed to increase to over 25 rotifers per mL. However, at lower rotifer concentration, the transformed algae was resistant to predatory grazing.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An isolated, genetically engineered organism comprising:
- a first exogenous fungal terpene synthase or a nucleic acid encoding the first exogenous fungal terpene synthase, wherein the first exogenous fungal terpene synthase comprises a polypeptide sequence having at least 90% sequence identity to SEQ ID NO: 1, or wherein the nucleic acid encoding the first exogenous fungal terpene synthase comprises a nucleic acid sequence encoding a polypeptide sequence having at least 90% sequence identity to SEQ ID NO: 1; and
- a second exogenous fungal terpene synthase or a nucleic acid encoding the second exogenous fungal terpene synthase, wherein the second exogenous fungal terpene synthase comprises a polypeptide sequence having at least 90% sequence identity to SEQ ID NO: 2, or wherein the nucleic acid encoding the second exogenous fungal terpene synthase comprises a nucleic acid sequence encoding a polypeptide sequence having at least 90% sequence identity to SEQ ID NO: 2; and
- wherein the isolated, genetically engineered organism produces aristolochene.

2. The organism of claim 1, thereby configured to produce a terpenoid or a sesquiterpene.

3. The organism of claim 1, wherein the nucleic acid encoding the first exogenous fungal terpene synthase and the second exogenous fungal terpene synthase is provided as a plasmid vector.

4. The organism of claim 1, wherein the first exogenous fungal terpene synthase comprises a polypeptide having at least 95% sequence identity to SEQ ID NO: 1, or wherein the nucleic acid encoding the first exogenous fungal terpene synthase comprises a nucleic acid sequence encoding a polypeptide sequence having at least 95% sequence identity to SEQ ID NO: 1; and wherein the second exogenous fungal terpene synthase comprises a polypeptide having at least 95% sequence identity to SEQ ID NO: 2, or wherein the nucleic acid encoding the second exogenous fungal terpene synthase comprises a nucleic acid sequence encoding a polypeptide sequence having at least 95% sequence identity to SEQ ID NO: 2.

5. The organism of claim 1, further comprising:
- an exogenous terpenoid precursor, an exogenous enzyme configured to synthesize a terpenoid precursor, or a nucleic acid encoding the exogenous enzyme.

6. The organism of claim 5, wherein the exogenous terpenoid precursor comprises dimethylallyl pyrophosphate, isopentenyl pyrophosphate, farnesyl diphosphate, geranyl pyrophosphate, or a salt thereof.

7. The organism of claim 5, wherein the exogenous enzyme comprises a farnesyl pyrophosphate synthase or a prenyl transferase.

* * * * *

SEQUENCE LISTING

```
<160> NUMBER OF SEQ ID NOS: 24

<210> SEQ ID NO 1
<211> LENGTH: 313
<212> TYPE: PRT
<213> ORGANISM: Hypoxylon sp. CI4A

<400> SEQUENCE: 1

Met Ser Leu Ala Pro Ser Ser Gly Asp Tyr Pro Ser Ser His Trp Thr
1               5                   10                  15

Pro Leu Ile His Pro Leu Ser Glu Lys Val Thr Arg Glu Val Asp Gly
                20                  25                  30

Tyr Tyr Leu Gln His Trp Pro Phe Pro Asp Glu Arg Ser Arg Lys Lys
            35                  40                  45

Phe Val Ala Ala Gly Phe Ser Arg Val Thr Cys Phe Tyr Phe Pro Lys
        50                  55                  60

Ala Leu Asn Asp Arg Ile His Phe Ala Cys Arg Leu Leu Thr Val Leu
65                  70                  75                  80

Phe Leu Ile Asp Asp Leu Leu Glu Tyr Met Ser Leu Glu Asp Gly Lys
                85                  90                  95
```

-continued

Ala Tyr Asn Glu Lys Leu Ile Pro Ile Ser Arg Gly Asp Val Leu Pro
                100                 105                 110

Asp Arg Ser Val Pro Val Glu Tyr Ile Thr Tyr Asp Leu Trp Glu Ser
        115                 120                 125

Met Arg Ala His Asp Arg Ile Met Ala Asp Ile Leu Glu Pro Val
    130                 135                 140

Phe Thr Phe Met Arg Ala Gln Thr Asp Ser Val Arg Leu Glu Ala Met
145                 150                 155                 160

Asp Leu Gly Arg Tyr Leu Glu Tyr Arg Glu Arg Asp Val Gly Lys Ala
                165                 170                 175

Leu Leu Gly Ala Leu Met Arg Phe Ser Met Gly Leu Val Pro Pro
            180                 185                 190

Glu Asp Leu Ala Ile Val Arg Pro Ile Asp Phe Asn Cys Ser Arg His
        195                 200                 205

Leu Ser Val Ile Asn Asp Ile Trp Ser Phe Glu Lys Glu Leu Leu Ala
    210                 215                 220

Ser Lys Asn Ala His Glu Glu Gly Gly Val Leu Cys Ser Ala Val Ser
225                 230                 235                 240

Val Leu Ala Asp Gln Val Gly Ile Ser Ile Asp Gly Ser Lys Arg Ile
                245                 250                 255

Leu Tyr Tyr Leu Cys Arg Glu Trp Glu His Arg His Glu Thr Leu Val
            260                 265                 270

Lys Glu Met Leu Gln Val Arg Asp Thr Pro Ala Leu Arg Ser Tyr Val
        275                 280                 285

Lys Gly Leu Glu Tyr Gln Met Ser Gly Asn Glu Met Trp Ser Arg Thr
    290                 295                 300

Thr Met Arg Tyr Leu Ala Pro Lys Asp
305                 310

<210> SEQ ID NO 2
<211> LENGTH: 334
<212> TYPE: PRT
<213> ORGANISM: Hypoxylon sp. CO27

<400> SEQUENCE: 2

Met Ala Pro Met Ala Glu Glu Cys Val Ser Ala Ser Pro Asn Gln Gly
1               5                   10                  15

His Ala Lys Pro Val Ala Thr Pro Met Arg Arg Ala Val His Ile Pro
            20                  25                  30

Ser Ser Glu Trp Thr Ala Gln Ile His Pro Leu His Glu Lys Val Ile
        35                  40                  45

Ala Glu Val Asp Gly Tyr Phe Leu Gln His Trp Pro Phe Pro Ser Glu
    50                  55                  60

Lys Thr Arg Lys Lys Phe Val Ala Ala Gly Phe Ser Arg Val Thr Cys
65                  70                  75                  80

Leu Tyr Phe Pro Lys Ala Leu Asp Asp Arg Ile His Phe Ala Cys Arg
                85                  90                  95

Leu Leu Thr Leu Leu Phe Leu Val Asp Asp Ile Leu Glu His Met Ser
            100                 105                 110

Leu Glu Asp Gly Arg Ala Tyr Asn Glu Arg Leu Met Pro Leu Phe Arg
        115                 120                 125

Gly Ser Val Leu Pro Asp Arg Ser Val Pro Val Glu Trp Ile Ser Tyr
    130                 135                 140

Asp Leu Trp Glu Ser Met Arg Ala His Asp Arg Asp Met Ala Asp Glu
145                 150                 155                 160

```
Ile Ile Glu Pro Val Phe Thr Phe Met Trp Ala Gln Thr Asp Pro Ala
                165                 170                 175

Arg Leu Thr Glu Met Gly Leu Gly Gln Tyr Leu Glu Tyr Arg Glu Arg
            180                 185                 190

Asp Val Gly Lys Ala Leu Leu Ala Ala Leu Met Arg Phe Ser Met Ala
        195                 200                 205

Leu Ile Val Ser Pro Ser Asp Leu Glu Met Val Arg Pro Val Asp Arg
    210                 215                 220

Asn Cys Ser Lys His Leu Ser Val Ile Asn Asp Ile Trp Ser Tyr Glu
225                 230                 235                 240

Lys Glu Val Leu Ala Ala Gln Thr Leu His Glu Glu Gly Gly Met Leu
                245                 250                 255

Cys Thr Ala Val Ala Val Leu Ser Lys Glu Ala Glu Ile Ser Thr Asp
            260                 265                 270

Ala Ser Lys Arg Val Leu Tyr His Leu Cys Arg Glu Trp Glu Asp Glu
        275                 280                 285

His Arg Ile Leu Val Ala Asp Ile Leu Ala Gln Asn Asp Thr Pro Val
    290                 295                 300

Leu Arg Ala Tyr Leu Gln Gly Leu Glu Phe Gln Met Ser Gly Asn Glu
305                 310                 315                 320

Leu Trp Ser Arg Thr Thr Leu Arg Tyr Val Gln Pro Arg Pro
                325                 330

<210> SEQ ID NO 3
<211> LENGTH: 308
<212> TYPE: PRT
<213> ORGANISM: Daldinia eschscholzii EC12

<400> SEQUENCE: 3

Met Glu Tyr Ala Gln Ser Thr Phe Thr Leu Leu Cys His Pro Arg Phe
1               5                   10                  15

Glu Val Val Glu Arg Glu Thr Asn Glu Tyr Phe Ile Ala Asn Trp Pro
            20                  25                  30

Phe Pro Asp Val Asn Ser Arg Asp Lys Phe Leu Lys Ala Gly Phe Ser
        35                  40                  45

Arg Cys Thr Cys Val Tyr Phe Pro Lys Ala Lys Asp Asp Arg Ile His
    50                  55                  60

Phe Ala Cys Arg Leu Leu Thr Leu Leu Phe Leu Ile Asp Asp Val Leu
65                  70                  75                  80

Glu Asp Met Ser Phe Glu Glu Gly Thr Ala Tyr Asn Gly Arg Leu Met
                85                  90                  95

Ser Ile Ile Arg Gly Asp Glu Val Pro Asp Arg Ser Ile Pro Val Gln
            100                 105                 110

Tyr Ile Ser His Asp Leu Trp Gln Ser Met Arg Ala His Asp Gln Arg
        115                 120                 125

Leu Ala Asp Gly Ile Leu Glu Pro Leu Phe Ile Phe Met Gln Ala Gln
    130                 135                 140

Thr Asp Lys Arg Arg Ala His Ser Met Ser Leu Gly Gln Tyr Ile Glu
145                 150                 155                 160

Tyr Arg Asp Lys Asp Ile Gly Gln Ala Leu Leu Cys Ala Leu Met Arg
                165                 170                 175

Phe Cys Leu Asp Ile Lys Leu Thr Gln His Glu Leu Asp Leu Val Arg
            180                 185                 190

Pro Ala Asp Val Asn Cys Gly Ile His Ile Ala Ile Met Asn Asp Ile
        195                 200                 205
```

```
Trp Ser Phe Glu Lys Glu Ala Leu Thr Ala Ala Arg Gly His Asp Glu
    210                 215                 220

Gly Gly Val Leu Cys Asn Ser Val Ala Ile Leu Ser Thr Glu Thr Ser
225                 230                 235                 240

Leu Ser Thr Ala Ser Ser Lys Arg Val Leu Tyr Cys Met Cys Arg Glu
                245                 250                 255

Trp Glu Thr Lys His Arg Arg Phe Val Asp Glu Leu Gly Gly Gly Arg
            260                 265                 270

Asp Thr Thr Leu Trp Thr Tyr Leu Gln Gly Leu Glu Tyr Gln Met Ser
        275                 280                 285

Gly Asn Glu Ala Trp Ser Lys Leu Thr Pro Arg Tyr Gln Ile Gln Glu
290                 295                 300

Ser Glu Lys Leu
305

<210> SEQ ID NO 4
<211> LENGTH: 334
<212> TYPE: PRT
<213> ORGANISM: Hypoxylon sp. EC38

<400> SEQUENCE: 4

Met Ala Pro Met Val Glu Glu Tyr Val Pro Thr Ser Pro Thr Gln Asp
1               5                   10                  15

Tyr Ala Lys Pro Val Ala Thr Pro Ile Gln Arg Ala Val His Ile Pro
            20                  25                  30

Ala Ser Glu Trp Thr Ala Gln Ile His Pro Leu His Glu Lys Val Ile
        35                  40                  45

Val Glu Val Asp Gly Tyr Phe Leu Gln His Trp Pro Phe Pro Asn Glu
    50                  55                  60

Lys Ala Arg Lys Lys Phe Val Ala Ala Gly Phe Ser Arg Val Thr Cys
65                  70                  75                  80

Leu Tyr Phe Pro Lys Ala Leu Asp Asp Arg Ile His Phe Ala Cys Arg
                85                  90                  95

Leu Leu Thr Leu Leu Phe Leu Val Asp Asp Ile Leu Glu His Met Ser
            100                 105                 110

Leu Glu Asp Gly Arg Ala Tyr Asn Glu Arg Leu Met Pro Leu Phe Arg
        115                 120                 125

Gly Ser Val Leu Pro Asp Arg Ser Val Pro Val Glu Trp Ile Ser Tyr
    130                 135                 140

Asp Leu Trp Glu Ser Met Arg Ala His Asp Arg Asp Met Ala Asp Glu
145                 150                 155                 160

Ile Ile Glu Pro Val Phe Thr Phe Met Arg Ala Gln Thr Asp Pro Ala
                165                 170                 175

Arg Leu Thr Asp Met Gly Leu Gly Gln Tyr Leu Glu Tyr Arg Glu Arg
            180                 185                 190

Asp Val Gly Lys Ala Leu Leu Ala Ala Leu Met Arg Phe Ser Met Ala
        195                 200                 205

Leu Thr Val Ser Pro Ser Asp Leu Glu Met Val Arg Pro Val Asp Arg
    210                 215                 220

Asn Cys Ser Lys His Leu Ser Val Ile Asn Asp Ile Trp Ser Tyr Glu
225                 230                 235                 240

Lys Glu Val Leu Ala Ala Gln Thr Leu His Glu Glu Gly Gly Met Leu
                245                 250                 255

Cys Thr Ala Val Ala Val Leu Ser Lys Glu Ala Glu Ile Ser Thr Asp
            260                 265                 270
```

```
Ala Ser Lys Arg Val Leu Tyr His Leu Cys Arg Glu Trp Glu Asp Glu
            275                 280                 285

His Arg Ile Leu Val Ala Asp Ile Leu Ala Gln Asn Asp Thr Pro Val
            290                 295                 300

Leu Arg Ala Tyr Leu Gln Gly Leu Glu Phe Gln Met Ser Gly Asn Glu
305                 310                 315                 320

Leu Trp Ser Arg Thr Thr Leu Arg Tyr Val Gln Pro Arg Pro
                325                 330
```

<210> SEQ ID NO 5
<211> LENGTH: 309
<212> TYPE: PRT
<213> ORGANISM: Hypoxylon sp. EC38

<400> SEQUENCE: 5

```
Met Glu Tyr Ala Gln Ser Thr Phe Ser Leu Leu Arg His Pro Arg Phe
1               5                   10                  15

Glu Glu Val Glu Arg Glu Thr Asn Glu Tyr Phe Leu Ala Asn Trp Pro
            20                  25                  30

Phe Pro Asp Leu Asn Ser Arg Asp Lys Phe Leu Lys Ala Gly Phe Thr
            35                  40                  45

Arg Cys Thr Cys Met Tyr Phe Pro Lys Ala Lys Asp Asp Arg Ile Gln
50                  55                  60

Phe Ala Cys Arg Leu Leu Thr Leu Leu Phe Leu Ile Asp Asp Val Leu
65                  70                  75                  80

Glu Asn Met Ser Phe Glu Glu Gly Thr Ala Tyr Asn Gly Lys Leu Met
                85                  90                  95

Pro Ile Ile Arg Gly Asp Glu Val Pro Asn Cys Ser Val Pro Val Gln
            100                 105                 110

Lys Ile Ser Tyr Asp Leu Trp Gln Ser Met Arg Ala Asn Asp Arg Glu
            115                 120                 125

Leu Ala Asp Gly Ile Leu Glu Pro Leu Phe Ile Phe Met Arg Ala Gln
            130                 135                 140

Thr Asp Lys Arg Arg Ala His Ser Met Ser Leu Gly Gln Tyr Leu Glu
145                 150                 155                 160

Tyr Arg Asp Lys Asp Ile Gly Gln Ala Leu Leu Cys Ala Leu Met Arg
                165                 170                 175

Phe Cys Leu Asp Ile Lys Leu Thr Gln His Glu Leu Asp Ile Val Arg
            180                 185                 190

Pro Ala Asn Val Asn Cys Gly Asn His Ile Ala Val Ile Asn Asp Ile
            195                 200                 205

Trp Ser Phe Glu Lys Glu Ala Leu Thr Ala Thr His Ala His Asp Glu
210                 215                 220

Gly Gly Val Leu Cys Asn Ser Val Ala Ile Leu Ser Ala Glu Thr Ala
225                 230                 235                 240

Leu Ser Thr Ala Ser Ser Lys Arg Val Leu Tyr Cys Leu Cys Arg Glu
                245                 250                 255

Trp Glu Thr Lys His Gln Gln Phe Val Asp Gly Leu Gly Asp Gly His
            260                 265                 270

Asp Ala Glu Thr Leu Arg Ala Tyr Leu Gln Gly Leu Glu Tyr Gln Met
            275                 280                 285

Ser Gly Asn Glu Ala Trp Ser Lys Ile Thr Pro Arg Tyr Gln Ile His
            290                 295                 300

Glu Ser Asp Arg Leu
305
```

<210> SEQ ID NO 6
<211> LENGTH: 342
<212> TYPE: PRT
<213> ORGANISM: Hypoxylon sp. CI4A

<400> SEQUENCE: 6

```
Met Ser Val Ala Val Glu Thr Ile Thr Ala Pro Thr Val Thr Leu Ser
1               5                   10                  15

Thr Ser Lys Pro Leu Val Lys Glu Thr Trp Lys Ile Pro Ala Ser Gly
            20                  25                  30

Trp Thr Pro Met Ile His Pro Arg Ala Glu Val Ser Arg Glu Val
        35                  40                  45

Asp Asn Tyr Phe Leu Glu His Trp Asn Phe Pro Asp Asp Asn Ala Arg
    50                  55                  60

Ser Thr Phe Leu Lys Ala Gly Phe Ser Arg Val Thr Cys Leu Tyr Phe
65                  70                  75                  80

Pro Leu Ala Lys Asp Asp Arg Ile His Phe Ala Cys Arg Leu Leu Thr
                85                  90                  95

Val Leu Phe Leu Ile Asp Asp Ile Leu Glu Glu Met Ser Phe Ala Asp
                100                 105                 110

Gly Glu Ala Leu Asn Asn Arg Leu Ile Glu Leu Ser Lys Gly Pro Glu
            115                 120                 125

Tyr Ala Thr Pro Asp Arg Ser Ile Pro Ala Glu Tyr Val Ile Tyr Asp
130                 135                 140

Leu Trp Glu Ser Met Arg Lys His Asp Leu Asp Leu Ala Asn Glu Val
145                 150                 155                 160

Leu Glu Pro Thr Phe Val Phe Met Arg Ser Gln Thr Asp Arg Val Arg
                165                 170                 175

Leu Ser Ile Lys Glu Leu Gly Glu Tyr Leu Arg Tyr Arg Glu Lys Asp
            180                 185                 190

Val Gly Lys Ala Leu Leu Ser Ala Leu Met Arg Tyr Ser Met Glu Leu
        195                 200                 205

Arg Pro Thr Ala Glu Glu Leu Ala Ala Leu Arg Pro Leu Glu Glu Asn
    210                 215                 220

Cys Ser Lys His Ile Ser Ile Val Asn Asp Ile Tyr Ser Phe Glu Lys
225                 230                 235                 240

Glu Val Ile Ala Ala Lys Thr Gly His Lys Glu Gly Ser Phe Leu Cys
                245                 250                 255

Ser Ala Val Lys Val Val Ala Thr Glu Thr Ala Leu Gly Ile Ser Ala
            260                 265                 270

Thr Lys Arg Val Leu Trp Ser Met Val Arg Glu Trp Glu Leu Val His
        275                 280                 285

Asp Ala Met Cys Asp Ala Leu Leu Leu Ala Ala Ser Gly Ala Gly Thr
    290                 295                 300

Asn Ser Gln Thr Val Arg Asp Tyr Met Arg Gly Leu Gln Tyr Gln Met
305                 310                 315                 320

Ser Gly Asn Glu Leu Trp Ser Cys Thr Thr Pro Arg Tyr Ile Glu Ala
                325                 330                 335

Ile Asp Gln Ala Ala Arg
            340
```

<210> SEQ ID NO 7
<211> LENGTH: 320
<212> TYPE: PRT
<213> ORGANISM: Aspergillus terreus

```
<400> SEQUENCE: 7

Met Lys Lys Pro Asn Gly Thr Asn Gly Ala Ser Ser Ser Leu Glu Pro
1               5                   10                  15

Pro Pro Ser Thr Phe Gln Pro Leu Cys His Pro Leu Val Glu Glu Val
            20                  25                  30

Ser Lys Glu Val Asp Gly Tyr Phe Leu Gln His Trp Asn Phe Pro Asn
        35                  40                  45

Glu Lys Ala Arg Lys Lys Phe Val Ala Ala Gly Phe Ser Arg Val Thr
    50                  55                  60

Cys Leu Tyr Phe Pro Lys Ala Leu Asp Asp Arg Ile His Phe Ala Cys
65                  70                  75                  80

Arg Leu Leu Thr Val Leu Phe Leu Ile Asp Asp Leu Leu Glu Tyr Met
                85                  90                  95

Ser Phe Glu Glu Gly Ser Ala Tyr Asn Glu Lys Leu Ile Pro Ile Ser
            100                 105                 110

Arg Gly Asp Val Leu Pro Asp Arg Ser Ile Pro Val Glu Tyr Ile Ile
        115                 120                 125

Tyr Asp Leu Trp Glu Ser Met Arg Ala His Asp Arg Glu Met Ala Asp
    130                 135                 140

Glu Ile Leu Glu Pro Val Phe Leu Phe Met Arg Ala Gln Thr Asp Arg
145                 150                 155                 160

Thr Arg Ala Arg Pro Met Gly Leu Gly Gly Tyr Leu Gly Tyr Arg Glu
                165                 170                 175

Arg Asp Val Gly Lys Glu Leu Leu Ala Ala Leu Met Arg Phe Ser Met
            180                 185                 190

Gly Leu Lys Leu Ser Pro Ser Glu Leu Gln Arg Val Arg Glu Ile Asp
        195                 200                 205

Ala Asn Cys Ser Lys His Leu Ser Val Val Asn Asp Ile Tyr Ser Tyr
    210                 215                 220

Glu Lys Glu Leu Tyr Thr Ser Lys Thr Ala His Ser Glu Gly Gly Ile
225                 230                 235                 240

Leu Cys Thr Ser Val Gln Ile Leu Ala Gln Glu Ala Asp Val Thr Ala
                245                 250                 255

Glu Ala Ala Lys Arg Val Leu Phe Val Met Cys Arg Glu Trp Glu Leu
            260                 265                 270

Arg His Gln Leu Leu Val Ala Arg Leu Ser Ala Glu Gly Leu Glu Thr
        275                 280                 285

Pro Gly Leu Ala Ala Tyr Val Glu Gly Leu Glu Tyr Gln Met Ser Gly
    290                 295                 300

Asn Glu Leu Trp Ser Gln Thr Thr Leu Arg Tyr Ser Val Val Val Asp
305                 310                 315                 320

<210> SEQ ID NO 8
<211> LENGTH: 342
<212> TYPE: PRT
<213> ORGANISM: Penicillium roqueforti

<400> SEQUENCE: 8

Met Ala Thr Ser Thr Glu Thr Ile Ser Ser Leu Ala Gln Pro Phe Val
1               5                   10                  15

His Leu Glu Asn Pro Ile Asn Ser Pro Leu Val Lys Glu Thr Ile Arg
            20                  25                  30

Pro Arg Asn Asp Thr Thr Ile Thr Pro Pro Thr Gln Trp Ser Tyr
        35                  40                  45
```

Leu Cys His Pro Arg Val Lys Glu Val Gln Asp Glu Val Asp Gly Tyr
 50                  55                  60

Phe Leu Glu Asn Trp Lys Phe Pro Ser Phe Lys Ala Val Arg Thr Phe
 65                  70                  75                  80

Leu Asp Ala Lys Phe Ser Glu Val Thr Cys Leu Tyr Phe Pro Leu Ala
                 85                  90                  95

Leu Asp Asp Arg Ile His Phe Ala Cys Arg Leu Leu Thr Val Leu Phe
             100                 105                 110

Leu Ile Asp Asp Val Leu Glu His Met Ser Phe Ala Asp Gly Glu Ala
         115                 120                 125

Tyr Asn Asn Arg Leu Ile Pro Ile Ser Arg Gly Asp Val Leu Pro Asp
130                 135                 140

Arg Thr Lys Pro Glu Glu Phe Ile Leu Tyr Asp Leu Trp Glu Ser Met
145                 150                 155                 160

Arg Ala His Asp Ala Glu Leu Ala Asn Glu Val Leu Glu Pro Thr Phe
                165                 170                 175

Val Phe Met Arg Ala Gln Thr Asp Arg Ala Arg Leu Ser Ile His Glu
            180                 185                 190

Leu Gly His Tyr Leu Glu Tyr Arg Glu Lys Asp Val Gly Lys Ala Leu
        195                 200                 205

Leu Ser Ala Leu Met Arg Phe Ser Met Gly Leu Arg Leu Ser Ala Asp
    210                 215                 220

Glu Leu Gln Asp Met Lys Ala Leu Glu Ala Asn Cys Ala Lys Gln Leu
225                 230                 235                 240

Ser Val Val Asn Asp Ile Tyr Ser Tyr Asp Lys Glu Glu Glu Ala Ser
                245                 250                 255

Arg Thr Gly His Lys Glu Gly Ala Phe Leu Cys Ser Ala Val Lys Val
            260                 265                 270

Leu Ala Glu Glu Ser Lys Leu Gly Ile Pro Ala Thr Lys Arg Val Leu
        275                 280                 285

Trp Ser Met Thr Arg Glu Trp Glu Thr Val His Asp Glu Ile Val Ala
    290                 295                 300

Glu Lys Ile Ala Ser Pro Asp Gly Cys Ser Glu Ala Ala Lys Ala Tyr
305                 310                 315                 320

Met Lys Gly Leu Glu Tyr Gln Met Ser Gly Asn Glu Gln Trp Ser Lys
                325                 330                 335

Thr Thr Arg Arg Tyr Asn
            340

<210> SEQ ID NO 9

<400> SEQUENCE: 9

000

<210> SEQ ID NO 10
<211> LENGTH: 303
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(7)
<223> OTHER INFORMATION: Xaa can be any naturally occurring amino acid

```
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (22)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (30)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(45)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
```

```
-continued

<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (91)..(95)
<223> OTHER INFORMATION: Xaa can be any naturally occurring amino acid
<220> FEATURE:
<221> NAME/KEY: misc_feature
<222> LOCATION: (97)..(101)
<223> OTHER INFORMATION: Xaa can be any naturally occurring amino acid
<220> FEATURE:
<221> NAME/KEY: misc_feature
<222> LOCATION: (103)..(106)
<223> OTHER INFORMATION: Xaa can be any naturally occurring amino acid
<220> FEATURE:
<221> NAME/KEY: misc_feature
<222> LOCATION: (108)..(113)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (121)..(122)
<223> OTHER INFORMATION: Xaa can be any naturally occurring amino acid
<220> FEATURE:
<221> NAME/KEY: misc_feature
<222> LOCATION: (124)..(126)
<223> OTHER INFORMATION: Xaa can be any naturally occurring amino acid
<220> FEATURE:
<221> NAME/KEY: misc_feature
<222> LOCATION: (128)..(131)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (144)..(145)
<223> OTHER INFORMATION: Xaa can be any naturally occurring amino acid
<220> FEATURE:
<221> NAME/KEY: misc_feature
<222> LOCATION: (147)..(151)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (160)..(161)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
```

```
<220> FEATURE:
<221> NAME/KEY: misc_feature
<222> LOCATION: (165)..(166)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (174)..(184)
<223> OTHER INFORMATION: Xaa can be any naturally occurring amino acid
<220> FEATURE:
<221> NAME/KEY: misc_feature
<222> LOCATION: (186)..(193)
<223> OTHER INFORMATION: Xaa can be any naturally occurring amino acid
<220> FEATURE:
<221> NAME/KEY: misc_feature
<222> LOCATION: (196)..(202)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid
<220> FEATURE:
<221> NAME/KEY: misc_feature
<222> LOCATION: (212)..(218)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (223)..(224)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (230)..(243)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (248)..(251)
<223> OTHER INFORMATION: Xaa can be any naturally occurring amino acid
<220> FEATURE:
<221> NAME/KEY: misc_feature
<222> LOCATION: (256)..(257)
<223> OTHER INFORMATION: Xaa can be any naturally occurring amino acid
<220> FEATURE:
<221> NAME/KEY: misc_feature
<222> LOCATION: (259)..(281)
<223> OTHER INFORMATION: Xaa can be any naturally occurring amino acid
<220> FEATURE:
<221> NAME/KEY: misc_feature
<222> LOCATION: (283)..(284)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
```

<220> FEATURE:
<221> NAME/KEY: misc_feature
<222> LOCATION: (298)..(299)
<223> OTHER INFORMATION: Xaa can be any naturally occurring amino acid
<220> FEATURE:
<221> NAME/KEY: misc_feature
<222> LOCATION: (301)..(301)
<223> OTHER INFORMATION: Xaa can be any naturally occurring amino acid

<400> SEQUENCE: 10

Xaa Xaa Xaa Xaa Xaa Xaa Xaa His Pro Xaa Xaa Xaa Val Xaa Xaa
1               5                   10                  15

Glu Xaa Xaa Xaa Tyr Xaa Xaa Xaa Xaa Trp Xaa Phe Pro Xaa Xaa Xaa
            20                  25                  30

Xaa Xaa Xaa Xaa Phe Xaa Xaa Ala Xaa Phe Xaa Xaa Xaa Thr Cys Xaa
        35                  40                  45

Tyr Phe Pro Xaa Ala Xaa Xaa Asp Arg Ile Xaa Phe Ala Cys Arg Leu
50                  55                  60

Leu Thr Xaa Leu Phe Leu Xaa Asp Asp Xaa Leu Glu Xaa Met Ser Xaa
65                  70                  75                  80

Xaa Xaa Gly Xaa Ala Xaa Asn Xaa Xaa Leu Xaa Xaa Xaa Xaa Xaa Gly
            85                  90                  95

Xaa Xaa Xaa Xaa Xaa Pro Xaa Xaa Xaa Xaa Pro Xaa Xaa Xaa Xaa Xaa
            100                 105                 110

Xaa Asp Leu Trp Xaa Ser Met Arg Xaa Xaa Asp Xaa Xaa Xaa Ala Xaa
            115                 120                 125

Xaa Xaa Xaa Glu Pro Xaa Phe Xaa Phe Met Xaa Xaa Gln Thr Asp Xaa
130                 135                 140

Xaa Arg Xaa Xaa Xaa Xaa Xaa Leu Gly Xaa Tyr Xaa Xaa Tyr Arg Xaa
145                 150                 155                 160

Xaa Asp Xaa Gly Xaa Xaa Leu Leu Xaa Ala Leu Met Arg Xaa Xaa Xaa
            165                 170                 175

Xaa Xaa Xaa Xaa Xaa Xaa Xaa Xaa Leu Xaa Xaa Xaa Xaa Xaa Xaa Xaa
            180                 185                 190

Xaa Asn Cys Xaa Xaa Xaa Xaa Xaa Xaa Asn Asp Ile Xaa Ser Xaa
            195                 200                 205

Xaa Lys Glu Xaa Xaa Xaa Xaa Xaa Xaa His Xaa Glu Gly Xaa Xaa
    210                 215                 220

Leu Cys Xaa Xaa Val Xaa Xaa Xaa Xaa Xaa Xaa Xaa Xaa Xaa Xaa
225                 230                 235                 240

Xaa Xaa Xaa Lys Arg Xaa Leu Xaa Xaa Xaa Xaa Arg Glu Trp Glu Xaa
            245                 250                 255

Xaa His Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Tyr Xaa Xaa Gly Leu Xaa Xaa
            275                 280                 285

Gln Met Ser Gly Asn Glu Xaa Trp Ser Xaa Xaa Thr Xaa Arg Tyr
    290                 295                 300

<210> SEQ ID NO 11
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid

```
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 11

Leu Xaa Asp Asp Xaa Xaa Glu Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 12

Asp Asp Xaa Xaa Glu
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 13

Xaa Asn Asp Xaa Xaa Ser Xaa Xaa Lys Glu Xaa Xaa
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
```

```
<400> SEQUENCE: 14

Asn Asp Xaa Xaa Ser Xaa Xaa Lys Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is any amino acid (e.g., G, A, V, I, and L)
<220> FEATURE:
<221> NAME/KEY: MISC_FEATURE
<222> LOCATION: (5)..(6)
<223> OTHER INFORMATION: X is any amino acid (e.g., G, A, V, I, and L)
<220> FEATURE:
<221> NAME/KEY: misc_feature
<222> LOCATION: (8)..(8)
<223> OTHER INFORMATION: Xaa can be any naturally occurring amino acid

<400> SEQUENCE: 15

Leu Xaa Asp Asp Xaa Xaa Glu Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(4)
<223> OTHER INFORMATION: X ia any amino acid (e.g., G, A, V, I, and L)

<400> SEQUENCE: 16

Asp Asp Xaa Xaa Glu
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X ia any amino acid (e.g., G, A, V, I, L, D, E,
      M, F, Y, and W)
<220> FEATURE:
<221> NAME/KEY: MISC_FEATURE
<222> LOCATION: (4)..(5)
<223> OTHER INFORMATION: X ia any amino acid (e.g., G, A, V, I, L, D, E,
      M, F, Y, and W)
<220> FEATURE:
<221> NAME/KEY: MISC_FEATURE
<222> LOCATION: (7)..(8)
<223> OTHER INFORMATION: X ia any amino acid (e.g., G, A, V, I, L, D, E,
      M, F, Y, and W)
<220> FEATURE:
<221> NAME/KEY: MISC_FEATURE
<222> LOCATION: (11)..(12)
<223> OTHER INFORMATION: X ia any amino acid (e.g., G, A, V, I, L, D, E,
      M, F, Y, and W)
```

```
<400> SEQUENCE: 17

Xaa Asn Asp Xaa Xaa Ser Xaa Xaa Lys Glu Xaa Xaa
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(4)
<223> OTHER INFORMATION: X ia any amino acid (e.g., G, A, V, I, L, D, E,
      M, F, Y, and W)
<220> FEATURE:
<221> NAME/KEY: MISC_FEATURE
<222> LOCATION: (6)..(7)
<223> OTHER INFORMATION: X ia any amino acid (e.g., G, A, V, I, L, D, E,
      M, F, Y, and W)

<400> SEQUENCE: 18

Asn Asp Xaa Xaa Ser Xaa Xaa Lys Glu
1               5

<210> SEQ ID NO 19

<400> SEQUENCE: 19

000

<210> SEQ ID NO 20
<211> LENGTH: 6798
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (146)..(396)
<223> OTHER INFORMATION: lacZalpha; Codon start: 1; Gene: lacZ fragment;
      Product: LacZalpha fragment of beta-galactosidase; Translation:
      LAVVLQRRDWENPGVTQLNRLAAHPPFASWRNSEEARTDRPSQQLRSLNGEWRLMRYFLLTHLCG
      ISHRIWCTLSTICSDAA*
<220> FEATURE:
<221> NAME/KEY: misc_feature
<222> LOCATION: (410)..(799)
<223> OTHER INFORMATION: VCP_b UTR
<220> FEATURE:
<221> NAME/KEY: misc_feature
<222> LOCATION: (802)..(819)
<223> OTHER INFORMATION: REPLACE; Note: Replace by XbaI digest. Insert
      ORF with ATG.PROTEIN.TAA. Kozak/Start Met is AGT.ATG
<220> FEATURE:
<221> NAME/KEY: misc_feature
<222> LOCATION: (813)..(815)
<223> OTHER INFORMATION: startM; start methionine
<220> FEATURE:
<221> NAME/KEY: promoter
<222> LOCATION: (819)..(1977)
<223> OTHER INFORMATION: Bidirectional promoter
<220> FEATURE:
<221> NAME/KEY: misc_feature
<222> LOCATION: (820)..(825)
<223> OTHER INFORMATION: Feature 24; Note: KOZAK:
      CTCTCTCAAGT.ATG.Protein.TAA. Add ORF by ATG-ORF-TAA. (no overhang
      needed)
<220> FEATURE:
<221> NAME/KEY: misc_feature
<222> LOCATION: (1972)..(1972)
<223> OTHER INFORMATION: Feature 24; Note: Promoter protein
      junction: CCACCACCACTTCTTAAGt.ATG.protein.taa.
```

```
<220> FEATURE:
<221> NAME/KEY: misc_feature
<222> LOCATION: (1979)..(2924)
<223> OTHER INFORMATION: E31_CI4A-322581; Translation: HypCI4A-322581
      (SEQ ID NO:1) (315 codons, 1 internal stop codon)
<220> FEATURE:
<221> NAME/KEY: misc_feature
<222> LOCATION: (2924)..(2924)
<223> OTHER INFORMATION: stop codon
<220> FEATURE:
<221> NAME/KEY: misc_feature
<222> LOCATION: (2925)..(3168)
<223> OTHER INFORMATION: VCP1 UTR
<220> FEATURE:
<221> NAME/KEY: promoter
<222> LOCATION: (3169)..(3440)
<223> OTHER INFORMATION: ACP prom
<220> FEATURE:
<221> NAME/KEY: misc_feature
<222> LOCATION: (3435)..(3435)
<223> OTHER INFORMATION: KOZAK; Note: Add gibson fragment by adding
      C.ATG.ORF.TAA. Restored sequence is CTCTTCAC.TTA.ACC.ATG.
<220> FEATURE:
<221> NAME/KEY: misc_feature
<222> LOCATION: (3440)..(3451)
<223> OTHER INFORMATION: replace; Note: Replace by gibson. Digest NcoI
      first, then add CATG.PROTEIN.TAA. CATG is C with start methionine.
      Use Phusion for insert.
<220> FEATURE:
<221> NAME/KEY: misc_feature
<222> LOCATION: (3441)..(3443)
<223> OTHER INFORMATION: ACP start ATG
<220> FEATURE:
<221> NAME/KEY: misc_feature
<222> LOCATION: (3455)..(3631)
<223> OTHER INFORMATION: FBA UTR
<220> FEATURE:
<221> NAME/KEY: promoter
<222> LOCATION: (3632)..(4112)
<223> OTHER INFORMATION: gapdh promoter
<220> FEATURE:
<221> NAME/KEY: misc_feature
<222> LOCATION: (4113)..(4487)
<223> OTHER INFORMATION: BleoR; Gene: Sh ble from Streptoalloteichus
      hindustanus; Product: antibiotic-binding protein; Note: confers
      resistance to bleomycin, phleomycin, and Zeocin(TM)
<220> FEATURE:
<221> NAME/KEY: misc_feature
<222> LOCATION: (4488)..(4672)
<223> OTHER INFORMATION: GAPDH terminator
<220> FEATURE:
<221> NAME/KEY: misc_feature
<222> LOCATION: (4691)..(4712)
<223> OTHER INFORMATION: lacZalpha; Gene: lacZ fragment; Product:
      LacZalpha fragment of beta-galactosidase; Translation: MTMITPS
<220> FEATURE:
<221> NAME/KEY: primer_bind
<222> LOCATION: (4708)..(4724)
<223> OTHER INFORMATION: M13 rev; Note: common sequencing primer, one of
      multiple similar variants
<220> FEATURE:
<221> NAME/KEY: protein_bind
<222> LOCATION: (4732)..(4748)
<223> OTHER INFORMATION: lac operator; Bound moiety: lac repressor
      encoded by lacI; Note: The lac repressor binds to the lac operator
      to inhibit transcription in E. coli. This inhibition can be
      relieved by adding lactose or isopropyl-beta-D-
      thiogalactopyranoside (IPTG).
<220> FEATURE:
<221> NAME/KEY: promoter
<222> LOCATION: (4756)..(4786)
<223> OTHER INFORMATION: lac promoter; Note: promoter for the E. coli
      lac operon
<220> FEATURE:
<221> NAME/KEY: protein_bind
<222> LOCATION: (4801)..(4822)
<223> OTHER INFORMATION: CAP binding site; Bound moiety: E. coli
      catabolite activator protein; Note: CAP binding activates
      transcription in the presence of cAMP.
```

```
<220> FEATURE:
<221> NAME/KEY: rep_origin
<222> LOCATION: (5110)..(5698)
<223> OTHER INFORMATION: ori; Direction: LEFT; Note: high-copy-number
      ColE1/pMB1/pBR322/pUC origin of replication
<220> FEATURE:
<221> NAME/KEY: misc_feature
<222> LOCATION: (5876)..(6685)
<223> OTHER INFORMATION: KanR; Gene: aph(3')-Ia; Product: aminoglycoside
      phosphotransferase; Note: confers resistance to kanamycin in
      bacteria or G418 (Geneticin) in eukaryotes

<400> SEQUENCE: 20
```

| | | | | | |
|---|---|---|---|---|---|
| tcgcgcgttt | cggtgatgac | ggtgaaaacc | tctgacacat | gcagctcccg | gagacggtca    60 |
| cagcttgtct | gtaagcggat | gccgggagca | gacaagcccg | tcagggcgcg | tcagcgggtg   120 |
| ttggcgggtg | tcggggctgg | cttaactatg | cggcatcaga | gcagattgta | ctgagagtgc   180 |
| accatatgcg | gtgtgaaata | ccgcacagat | gcgtaaggag | aaaataccgc | atcaggcgcc   240 |
| attcgccatt | caggctgcgc | aactgttggg | aagggcgatc | ggtgcgggcc | tcttcgctat   300 |
| tacgccagct | ggcgaaaggg | ggatgtgctg | caaggcgatt | aagttgggta | acgccagggt   360 |
| tttcccagtc | acgacgttgt | aaaacgacgg | ccagagaatt | cgtttaaacc | agtgggataa   420 |
| aaggcagtcc | gaaggtttcc | gtcatcctcg | tcctcgttct | cgttttccac | ctactcatct   480 |
| tccgtttctt | gagtgcgtcg | ccgctgggtt | ttcctgaaat | aaacgctctt | tcatattatt   540 |
| ttttttcatc | tttttttctt | ctattgtttt | ttttgacttg | tctttgacct | tgtctgtagc   600 |
| tcttaacaga | tcaaaggaaa | agcgaaggcg | ccgcatgatc | ctcgtccttc | acgaaacaca   660 |
| aacatcagcc | tcttcaccct | ctttccctgt | tcctgctac  | gaaatcgaca | acattcaaca   720 |
| agtcagaaac | gctcctcttc | actgaacaca | caatcgaccg | ctgctttcct | cttccctcc    780 |
| gcagtaatca | acacgtctat | tctagaaatc | tacatctaga | cttgagagag | tggtggagtt   840 |
| gactatcgtg | tggagtgttt | ggggagggaa | agggcggagc | gtgagtgcaa | tgcgaggtgg   900 |
| gcgaagtggg | catgtgataa | atggctgtgt | ggtggaggcc | ttcgctgcgt | gtctgtgact   960 |
| gtcttgattg | tgtgcttaga | gtgagatacc | aaagcaagat | cttccctgcc | atcccttcat  1020 |
| tgtcccacgg | gccgaagaga | tgggggggctt | gacgagagga | cagggatgca | ggtgcgatgc  1080 |
| ggtcctgtcc | tatggggcag | gaaccgctgg | ggtgcagtgg | cacagaagac | agaaggagaa  1140 |
| aacacatgca | ccaaataaac | atatgacaaa | gagtcaagca | gtagtcaaaa | caaccaaaac  1200 |
| gtaagcaaga | cggaacaaga | tggcacgcgt | ctgcaacaga | ccggctcgcg | ccgaacgtgc  1260 |
| ctcctgcttt | tcaacgatcc | tgcgaggtca | accaggattt | gctcgccggg | acgatttcat  1320 |
| cccccttatca | acgagcccctt | gaggctccag | gcgtgcttcc | acaccccagt | tggtaacagg  1380 |
| acattggggc | atcttgccta | tcttgtctta | gtgccgaaag | cctcaacgac | ctcctatggg  1440 |
| gtctgctcaa | cgcctcaacc | ttgcagtaag | gcatccccga | gggcaagacc | cgcaaagcct  1500 |
| tctgtcgtcg | dacaaagcgg | agcgagggaa | caggctcagc | tcaaccctct | tgagagccca  1560 |
| taagtgcccc | ctgatctatc | ttcaacagtc | tttccctgtc | acaagaaaac | ccagctagtt  1620 |
| gaccaagttg | ctagagctga | taccttgtac | ttcgctcttt | gtgtgcttta | cctgattgga  1680 |
| catggacaga | cctcccccttg | ctcttccttc | taggagcctg | ggctctcgct | cttgttcttt  1740 |
| cgagagacct | ttcccttgag | ttgcgtatcc | agcgatcaag | tatgaagagt | gctttcaaac  1800 |
| ctagatacgt | tctgcccagt | tctccttgcc | ttttccacac | gtgctccaca | tcttcacacg  1860 |
| actcgcacca | tacccgacga | aaccccctcaa | aacatcgcaa | cacttacatc | ccgctcgtgt  1920 |
| cccacccccg | atgccatatc | ctctacagca | gcagcaccac | caccaccact | tcttaagtat  1980 |

-continued

```
gtcgctcgcc ccctcgtcgg gcgactaccc ttcgtcgcac tggacgccgc tcatccaccc    2040
tctctcggag aaggtcaccc gcgaggtcga cggctactac ctccagcact ggcccttccc    2100
ggacgagcgc tcgcgcaaga agttcgtcgc cgcgggcttc tcgcgcgtca cctgcttcta    2160
cttcccgaag gcgctcaacg accgcatcca cttcgcctgc cgcctcctca ccgtcctctt    2220
cctcatcgac gacctcctcg agtacatgtc gctcgaggac ggcaaggcct acaacgagaa    2280
gctcatcccg atctcgcgcg cgacgtcctc ccccgaccgc tcggtccccg tcgagtacat    2340
cacgtacgac ctctgggagt cgatgcgcgc ccacgaccgc atcatggcgg acgacatcct    2400
cgagcccgtc ttcacgttca tgcgcgccca gacggactcg gtccgcctcg aggccatgga    2460
cctcggccgc tacctcgagt accgcgagcg cgacgtcggc aaggcgctcc tcggcgccct    2520
catgcgcttc tcgatgggcc tcgtcgtccc gcccgaggac ctcgcgatcg tccgcccat     2580 cgacttcaac tgctcgcgcc acctctcggt catcaacgac atctggtcgt tcgagaagga    2640
gctcctcgcg tcgaagaacg cccacgagga aggcggcgtc ctctgctcgg ccgtctcggt    2700
cctcgccgac caggtcggca tctcgatcga cggctcgaag cgcatcctct actacctctg    2760
ccgcgagtgg gagcaccgcc acgagacgct cgtcaaggag atgctccagg tccgcgacac    2820
gcccgccctc cgctcgtacg tcaagggcct cgagtaccag atgtcgggca acgagatgtg    2880
gtcgcgcacc accatgcgct acctcgcccc caaggactga ctgagcttct gtggaagagc    2940
cagtggtagt agcagtagca gcagcagtag cagccgcagc actcagtgtt ggcgcgagag    3000
attgtccatc ccttcttaac ctaccggaag agaaataagg cctttctccc gtagctgtct    3060
tcgtttgttt gtgctgattg cttggtatga gagtgttgaa tctcctgcat catgttttc     3120 tctgtagtcc tttcctaccc ccgtcatttt cttttctccc tggttcttac ccgtacacgc    3180
ccatgctaca ccctgcctac acacgcgcac acgcgcacaa acacacacat acatcaacac    3240
acacaataca gcaatccgtg cctctctctt actctattca agcgtgctgc gtggcctttg    3300
acttcattcc tcttgtccac ccgccggcca ccagtagaac cagcaccacg tccaccctca    3360
tctcactcct ctttccccca catcccctac tactccatcc ttctcatcta cagtcacacc    3420
ttcctcctct tcacttaacc atggtaacca tggtaagtta caagcaggac ggaagagtgg    3480
actcagatgg gaaaatacaa atatttatga aggtgcacat ttagattgcg acttttcat     3540 gacacagaga cacgtggaga ttttcttact cctcatctct gtgtcactta atttcttttt    3600
catcccttta caacagtgtt ggtgcgctca tcgaccgcac atctacctcg cacgccaccc    3660
ataacctacc acaggcggtg ttcaagcccg tggctgcatg cgtcgtccct tccgctacca    3720
cccccgagct tgcacacgat ggcggctcgc tcgtgagtgg ctggtgcaag gcgaaagcaa    3780
ccacaatatt ctggcctttg ccattttata ttgcctggcc ttgaccttgt aagcagcgtc    3840
cccacagctt cctccaccag cacactgtgt cccgcatgtg tggattgggg cagtgggcag    3900 tcttcttgt tgtcttgcac gcccgctgga ggtcaagttg gatcagtatt tgtacatgca     3960
cggaagagag cgtgacgagg cggagacaaa ccgctccaag ccatcttccc ataccaagca    4020
aacacaacac gtactcaccc tccactctcc ttgtcctttt tccctctgac acgcgcacct    4080
acagcacccc tcgacgaccc tcacctgtct aaatggccaa gttgaccagt gccgttccgg    4140
tgctcaccgc gcgcgacgtc gccggagcgg tcgagttctg gaccgaccgg ctcgggttct    4200
cccgggactt cgtggaggac gacttcgccg gtgtggtccg ggacgacgtg accctgttca    4260
tcagcgcggt ccaggaccag gtggtgccgg acaacaccct ggcctgggtg tgggtgcgcg    4320
gcctggacga gctgtacgcc gagtggtcgg aggtcgtgtc cacgaacttc cgggacgcct    4380
```

```
ccgggccggc catgaccgag atcggcgagc agccgtgggg gcgggagttc gccctgcgcg    4440
acccggccgg caactgcgtg cacttcgtgg ccgaggagca ggactaaatc tgttagttgc    4500
aacagtagca gcaacagctg tagtttttgt acgcgcagtg ccttgtgcta ggagggagta    4560
gcagtagtag tagcagcagc agcagcagcg acaattttat gtgtaaggcg tggtccttgt    4620
gtgctttgtg tctgctttgt ctctcgtgtg tcaagaggca ttcgtaggga ttgtttaaac    4680
ctcgagtata agcttggtgt aatcatggtc atagctgttt cctgtgtgaa attgttatcc    4740
gctcacaatt ccacacaaca tacgagccgg aagcataaag tgtaaagcct ggggtgccta    4800
atgagtgagc taactcacat taattgcgtt gcgctcactg cccgctttcc agtcgggaaa    4860
cctgtcgtgc cagctgcatt aatgaatcgg ccaacgcgcg gggagaggcg gtttgcgtat    4920
tgggcgctct tccgcttcct cgctcactga ctcgctgcgc tcggtcgttc ggctgcggcg    4980
agcggtatca gctcactcaa aggcggtaat acggttatcc acagaatcag gggataacgc    5040
aggaaagaac atgtgagcaa aaggccagca aaaggccagg aaccgtaaaa aggccgcgtt    5100
gctggcgttt ttccataggc tccgcccccc tgacgagcat cacaaaaatc gacgctcaag    5160
tcagaggtgg cgaaacccga caggactata aagataccag gcgtttcccc ctggaagctc    5220
cctcgtgcgc tctcctgttc cgaccctgcc gcttaccgga tacctgtccg cctttctccc    5280
ttcgggaagc gtggcgcttt ctcatagctc acgctgtagg tatctcagtt cggtgtaggt    5340
cgttcgctcc aagctgggct gtgtgcacga accccccgtt cagcccgacc gctgcgcctt    5400
atccggtaac tatcgtcttg agtccaaccc ggtaagacac gacttatcgc cactggcagc    5460
agccactggt aacaggatta gcagagcgag gtatgtaggc ggtgctacag agttcttgaa    5520
gtggtggcct aactacggct acactagaag aacagtattt ggtatctgcg ctctgctgaa    5580
gccagttacc ttcggaaaaa gagttggtag ctcttgatcc ggcaaacaaa ccaccgctgg    5640
tagcggtggt ttttttgttt gcaagcagca gattacgcgc agaaaaaaag gatctcaaga    5700
agatcctttg atcttttcta cggggtctga cgctcagtgg aacgaaaact cacgttaagg    5760
gattttggtc atgagattat caaaaaggat cttcacctag atccttttaa attaaaaatg    5820
aagttttaaa tcaagcccaa tctgaataat gttacaacca attaaccaat ctgattaga    5880 aaaactcatc gagcatcaaa tgaaactgca atttattcat atcaggatta tcaataccat    5940 attttttgaaa aagccgtttc tgtaatgaag gagaaaactc accgaggcag ttccatagga    6000
tggcaagatc ctggtatcgg tctgcgattc cgactcgtcc aacatcaata caacctatta    6060
atttcccctc gtcaaaaata aggttatcaa gtgagaaatc accatgagtg acgactgaat    6120
ccggtgagaa tggcaaaagt ttatgcattt cttttccaga cttgttcaaca ggccagccat    6180 tacgctcgtc atcaaaatca ctcgcatcaa ccaaaccgtt attcattcgt gattgcgcct    6240
gagcgagacg aaatacgcga tcgctgttaa aaggacaatt acaaacagga atcgaatgca    6300
accggcgcag gaacactgcc agcgcatcaa caatatttc acctgaatca ggatattctt    6360 ctaataccctg gaatgctgtt tttccgggga tcgcagtggt gagtaaccat gcatcatcag    6420
gagtacggat aaaatgcttg atggtcggaa gaggcataaa ttccgtcagc cagtttagtc    6480
tgaccatctc atctgtaaca tcattggcaa cgctacctt gccatgtttc agaaacaact    6540
ctggcgcatc gggcttccca tacaagcgat agattgtcgc acctgattgc ccgacattat    6600
cgcgagccca tttatacca tataaatcag catccatgtt ggaatttaat cgcggcctcg    6660
acgtttcccg ttgaatatgg ctcataacac cccttgtatt actgtttatg taagcagaca    6720
```

-continued

```
gttttattgt tcatgatgat atatttttat cttgtgcaat gtaacatcag agattttgag    6780
acacgggcca gagctgca                                                   6798
```

```
<210> SEQ ID NO 21
<211> LENGTH: 6861
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (146)..(396)
<223> OTHER INFORMATION: lacZalpha; Codon start: 1; Gene: lacZ fragment;
      Product: LacZalpha fragment of beta-galactosidase; Translation:
      LAVVLQRRDWENPGVTQLNRLAAHPPFASWRNSEEARTDRPSQQLRSLNGEWRLMRYFLLTHLCG
      ISHRIWCTLSTICSDAA*
<220> FEATURE:
<221> NAME/KEY: misc_feature
<222> LOCATION: (410)..(799)
<223> OTHER INFORMATION: VCP_b UTR
<220> FEATURE:
<221> NAME/KEY: misc_feature
<222> LOCATION: (802)..(819)
<223> OTHER INFORMATION: REPLACE; Note: Replace by XbaI digest. Insert
      ORF with ATG.PROTEIN.TAA. ozak/Start met is AGT.ATG
<220> FEATURE:
<221> NAME/KEY: misc_feature
<222> LOCATION: (813)..(815)
<223> OTHER INFORMATION: startM; start methionine
<220> FEATURE:
<221> NAME/KEY: promoter
<222> LOCATION: (819)..(1977)
<223> OTHER INFORMATION: bidirectional promoter
<220> FEATURE:
<221> NAME/KEY: misc_feature
<222> LOCATION: (820)..(825)
<223> OTHER INFORMATION: Feature 24; Note: KOZAK:
      CTCTCTCAAGT.ATG.Protein.TAA. Add ORF by ATG-ORF-TAA. (no overhang
      needed)
<220> FEATURE:
<221> NAME/KEY: misc_feature
<222> LOCATION: (1972)..(1972)
<223> OTHER INFORMATION: Feature 24; Note: Promoter protein junction:
      CCACCACCACTTCTTAAGt.ATG.protein.taa.
<220> FEATURE:
<221> NAME/KEY: misc_feature
<222> LOCATION: (1979)..(2983)
<223> OTHER INFORMATION: EV30_CO27-392541; Translation: HypCO27-392541
      (SEQ ID NO:2)
<220> FEATURE:
<221> NAME/KEY: misc_feature
<222> LOCATION: (2987)..(2987)
<223> OTHER INFORMATION: stop codon
<220> FEATURE:
<221> NAME/KEY: misc_feature
<222> LOCATION: (2988)..(3231)
<223> OTHER INFORMATION: VCP1 UTR
<220> FEATURE:
<221> NAME/KEY: promoter
<222> LOCATION: (3232)..(3503)
<223> OTHER INFORMATION: ACP prom
<220> FEATURE:
<221> NAME/KEY: misc_feature
<222> LOCATION: (3498)..(3498)
<223> OTHER INFORMATION: KOZAK; Note: Add gibson fragment by adding
      C.ATG.ORF.TAA. Restored sequence is CTCTTCAC.TTA.ACC.ATG
<220> FEATURE:
<221> NAME/KEY: misc_feature
<222> LOCATION: (3503)..(3514)
<223> OTHER INFORMATION: replace; NOTE: Replace by gibson. Digest NcoI
      first, then add CATG.PROTEIN.TAA. CATG is C with start methionine.
      Use Phusion for insert
<220> FEATURE:
<221> NAME/KEY: misc_feature
<222> LOCATION: (3504)..(3506)
<223> OTHER INFORMATION: ACP start ATG
```

```
<220> FEATURE:
<221> NAME/KEY: misc_feature
<222> LOCATION: (3518)..(3694)
<223> OTHER INFORMATION: FBA UTR
<220> FEATURE:
<221> NAME/KEY: promoter
<222> LOCATION: (3695)..(4175)
<223> OTHER INFORMATION: gadph promoter
<220> FEATURE:
<221> NAME/KEY: misc_feature
<222> LOCATION: (4176)..(4550)
<223> OTHER INFORMATION: BleoR; Gene: Sh ble from Streptoalloteichus
      hindustanus; Product: antibiotic-binding protein; Note: confers
      resistance to bleomycin, phleomycin, and Zeocin(TM)
<220> FEATURE:
<221> NAME/KEY: misc_feature
<222> LOCATION: (4551)..(4735)
<223> OTHER INFORMATION: GAPDH terminator
<220> FEATURE:
<221> NAME/KEY: misc_feature
<222> LOCATION: (4754)..(4775)
<223> OTHER INFORMATION: lacZalpha; Gene: lacZ fragment; Product:
      LacZalpha fragment of beta-galactosidase; Translation: MTMITPS
<220> FEATURE:
<221> NAME/KEY: primer_bind
<222> LOCATION: (4771)..(4787)
<223> OTHER INFORMATION: M13 rev; Note: common sequencing primer, one of
      multiple similar variants
<220> FEATURE:
<221> NAME/KEY: protein_bind
<222> LOCATION: (4795)..(4811)
<223> OTHER INFORMATION: lac operator; Bound moiety: lac repressor
      encoded by lacI; Note: The lac repressor binds to the lac operator
      to inhibit transcription in E. coli. This inhibition can be
      relieved by adding lactose or isopropyl-beta-D-
      thiogalactopyranoside (IPTG).
<220> FEATURE:
<221> NAME/KEY: promoter
<222> LOCATION: (4819)..(4849)
<223> OTHER INFORMATION: lac promoter; Note: promoter for the E. coli
      lac operon
<220> FEATURE:
<221> NAME/KEY: protein_bind
<222> LOCATION: (4864)..(4885)
<223> OTHER INFORMATION: CAP binding site; Bound moiety: E. coli
      catabolite activator protein; Note: CAP binding activates
      transcription in the presence of cAMP.
<220> FEATURE:
<221> NAME/KEY: rep_origin
<222> LOCATION: (5173)..(5761)
<223> OTHER INFORMATION: ori; Direction: LEFT; Note: high-copy-number
      ColE1/pMB1/pBR322/pUC origin of replication
<220> FEATURE:
<221> NAME/KEY: misc_feature
<222> LOCATION: (5939)..(6748)
<223> OTHER INFORMATION: KanR; Gene: aph(3')-Ia; Product: aminoglycoside
      phosphotransferase; Note: confers resistance to kanamycin in
      bacteria or G418 (Geneticin) in eukaryotes

<400> SEQUENCE: 21
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg       120 ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagagaatt cgtttaaacc agtgggataa       420
aaggcagtcc gaaggtttcc gtcatcctcg tcctcgttct cgttttccac ctactcatct       480
tccgtttctt gagtgcgtcg ccgctgggtt ttcctgaaat aaacgctctt tcatattatt       540
```

```
tttttttcatc ttttttttctt ctattgtttt ttttgacttg tctttgacct tgtctgtagc    600
tcttaacaga tcaaaggaaa agcgaaggcg ccgcatgatc ctcgtccttc acgaaacaca    660
aacatcagcc tcttcaccct ctttccctgt ttcctgctac gaaatcgaca acattcaaca    720
agtcagaaac gctcctcttc actgaacaca caatcgaccg ctgctttcct ccttccctcc    780
gcagtaatca acacgtctat tctagaaatc tacatctaga cttgagagag tggtggagtt    840
gactatcgtg tggagtgttt ggggagggaa agggcggagc gtgagtgcaa tgcgaggtgg    900
gcgaagtggg catgtgataa atggctgtgt ggtggaggcc ttcgctgcgt gtctgtgact    960
gtcttgattg tgtgcttaga gtgagatacc aaagcaagat cttccctgcc atcccttcat   1020
tgtcccacgg gccgaagaga tgggggctt gacgagagga cagggatgca ggtgcgatgc   1080
ggtcctgtcc tatggggcag gaaccgctgg ggtgcagtgg cacagaagac agaaggagaa   1140
aacacatgca ccaaataaac atatgacaaa gagtcaagca gtagtcaaaa caaccaaaac   1200
gtaagcaaga cggaacaaga tggcacgcgt ctgcaacaga ccggctcgcg ccgaacgtgc   1260
ctcctgcttt tcaacgatcc tgcgaggtca accaggattt gctcgccggg acgatttcat   1320 cccccttatca acgagccctt gaggctccag gcgtgcttcc acaccccagt tggtaacagg   1380
acattggggc atcttgccta tcttgtctta gtgccgaaag cctcaacgac ctcctatggg   1440
gtctgctcaa cgcctcaacc ttgcagtaag catccccga gggcaagacc cgcaaagcct   1500
tctgtcgtcg gacaaagcgg agcgagggaa caggctcagc tcaaccctct tgagagccca   1560
taagtgcccc ctgatctatc ttcaacagtc tttccctgtc acaagaaaac ccagctagtt   1620
gaccaagttg ctagagctga taccttgtac ttcgctcttt gtgtgcttta cctgattgga   1680
catggacaga cctcccttg ctcttccttc taggagcctg ggctctcgct cttgttcttt   1740
cgagagacct ttcccttgag ttgcgtatcc agcgatcaag tatgaagagt gctttcaaac   1800
ctagatacgt tctgcccagt tctcttgccc ttttccacac gtgctccaca tcttcacacg   1860
actcgcacca tacccgacga aacccctcaa aacatcgcaa cacttacatc ccgctcgtgt   1920 cccaccccccg atgccatatc ctctacagca gcagccacac caccaccact tcttaagtat   1980
ggcccccatg gcggaggagt gcgtctcggc gtcgcccaac cagggccacg ccaagcccgt   2040 cgccacccc atgcgccgcg ctgtccacat cccctcgtcg gagtggaccg cccagatcca   2100
ccctctccac gagaaggtca tcgccgaggt cgacggctac ttcctccagc actgccgtt   2160 ccctcggag aagacccgca agaagttcgt cgccgcgggc ttctcgcgcg tcacctgcct   2220
ctacttcccg aaggcgctcg acgaccgcat ccacttcgcc tgccgcctcc tcaccctcct   2280
cttcctcgtc gacgacatcc tcgagcacat gtcgctcgag acggccgcg cttacaacga   2340 gcgcctcatg cctctcttcc gcggctcggt cctcccccgac cgtcggtcc ccgtcgagtg   2400 gatctcgtac gacctctggg agtcgatgcg cgcccacgac cgcgacatgg ccgacgagat   2460
catcgagccg gtcttcacgt tcatgtgggc ccagaccgac cccgcccgcc tcaccgagat   2520
gggcctcggc cagtacctcg agtaccgcga gcgcgacgtc ggcaaggcgc tcctcgccgc   2580
cctcatgcgc ttctcgatgg ccctcatcgt ctcgccctcg gacctcgaga tggtccgccc   2640
cgtcgaccgc aactgctcga agcacctctc ggtcatcaac gacatctggt cgtacgagaa   2700
ggaagtcctc gccgcccaga ccctccacga ggaaggcggc atgctctgca ccgccgtcgc   2760
ggtcctctcg aaggaagcgg agatctcgac cgacgcctcg aagcgcgtcc tctaccacct   2820
ctgccgcgag tgggaggacg agcaccgcat cctcgtcgcc gacatcctcg cccagaacga   2880 caccccccgtc ctccgcgcct acctccaggg cctcgagttc cagatgtcgg gcaacgagct   2940
```

```
ctggtcgcgc accaccctcc gctacgtcca gcctcgcccg tgactgagct tctgtggaag    3000
agccagtggt agtagcagta gcagcagcag tagcagccgc agcactcagt gttggcgcga    3060
gagattgtcc atcccttctt aacctaccgg aagagaaata aggcctttct cccgtagctg    3120
tcttcgtttg tttgtgctga ttgcttggta tgagagtgtt gaatctcctg catcatgttt    3180
ttctctgtag tcctttccta cccccgtcat tttcttttct ccctggttct tacccgtaca    3240
cgccatgct acaccctgcc tacacacgcg cacacgcgca caaacacaca catacatcaa     3300
cacacacaat acagcaatcc gtgcctctct cttactctat tcaagcgtgc tgcgtggcct    3360
ttgacttcat tcctcttgtc cacccgccgg ccaccagtag aaccagcacc acgtccaccc    3420
tcatctcact cctctttccc ccacatcccc tactactcca tccttctcat ctacagtcac    3480
accttcctcc tcttcactta accatggtaa ccatggtaag ttacaagcag gacggaagag    3540
tggactcaga tgggaaaata caaatattta tgaaggtgca catttagatt gcgactttt     3600
catgacacag agacacgtgg agattttctt actcctcatc tctgtgtcac ttaatttctt    3660
tttcatccct ttacaacagt gttggtgcgc tcatcgaccg cacatctacc tcgcacgcca    3720
cccataacct accacaggcg gtgttcaagc ccgtggctgc atgcgtcgtc ccttccgcta    3780
ccaccccga gcttgcacac gatggcggct cgctcgtgag tggctggtgc aaggcgaaag     3840
caaccacaat attctggcct ttgccatttt atattgcctg gccttgacct tgtaagcagc    3900
gtccccacag cttcctccac cagcacactg tgtcccgcat gtgtggattg gggcagtggg    3960
cagtctttct tgttgtcttg cacgcccgct ggaggtcaag ttggatcagt atttgtacat    4020
gcacggaaga gagcgtgacg aggcggagac aaaccgctcc aagccatctt cccataccaa    4080
gcaaacacaa cacgtactca ccctccactc tccttgtcct ttttccctct gacacgcgca    4140
cctacagcac ccctcgacga ccctcacctg tctaaatggc caagttgacc agtgccgttc    4200
cggtgctcac cgcgcgcgac gtcgccggag cggtcgagtt ctggaccgac cggctcgggt    4260
tctcccggga cttcgtggag gacgacttcg ccggtgtggt ccgggacgac gtgaccctgt    4320
tcatcagcgc ggtccaggac caggtggtgc cggacaacac cctggcctgg gtgtgggtgc    4380
gcggcctgga cgagctgtac gccgagtggt cggaggtcgt gtccacgaac ttccgggacg    4440
cctccgggcc ggccatgacc gagatcggcg agcagccgtg ggggcgggag ttcgccctgc    4500
gcgacccggc cggcaactgc gtgcacttcg tggccgagga gcaggactaa atctgttagt    4560
tgcaacagta gcagcaacag ctgtagtttt tgtacgcgca gtgccttgtg ctaggaggga    4620
gtagcagtag tagtagcagc agcagcagca gcgacaattt tatgtgtaag gcgtggtcct    4680
tgtgtgcttt gtgtctgctt tgtctctcgt gtgtcaagag gcattcgtag ggattgttta    4740
aacctcgagt ataagcttgg tgtaatcatg gtcatagctg tttcctgtgt gaaattgtta    4800
tccgctcaca attccacaca acatacgagc cggaagcata aagtgtaaag cctggggtgc    4860
ctaatgagtg agctaactca cattaattgc gttgcgctca ctgcccgctt tccagtcggg    4920
aaacctgtcg tgccagctgc attaatgaat cggccaacgc gcgggagag gcggtttgcg     4980
tattgggcgc tcttccgctt cctcgctcac tgactcgctg cgctcggtcg ttcggctgcg    5040
gcgagcggta tcagctcact caaaggcggt aatacggtta ccacagaat cagggataa      5100
cgcaggaaag aacatgtgag caaaaggcca gcaaaaggcc aggaaccgta aaaaggccgc    5160
gttgctggcg ttttccata ggctccgccc ccctgacgag catcacaaaa atcgacgctc     5220
aagtcagagg tggcgaaacc cgacaggact ataaagatac caggcgtttc ccctggaag     5280
ctccctcgtg cgctctcctg ttccgaccct gccgcttacc ggatacctgt ccgcctttct    5340
```

```
cccttcggga agcgtggcgc tttctcatag ctcacgctgt aggtatctca gttcggtgta    5400
ggtcgttcgc tccaagctgg gctgtgtgca cgaaccccccc gttcagcccg accgctgcgc    5460
cttatccggt aactatcgtc ttgagtccaa cccggtaaga cacgacttat cgccactggc    5520
agcagccact ggtaacagga ttagcagagc gaggtatgta ggcggtgcta cagagttctt    5580
gaagtggtgg cctaactacg gctacactag aagaacagta tttggtatct gcgctctgct    5640
gaagccagtt accttcggaa aaagagttgg tagctcttga tccggcaaac aaaccaccgc    5700
tggtagcggt ggtttttttg tttgcaagca gcagattacg cgcagaaaaa aaggatctca    5760
agaagatcct ttgatctttt ctacgggtc tgacgctcag tggaacgaaa actcacgtta    5820
agggattttg gtcatgagat tatcaaaaag gatcttcacc tagatccttt taaattaaaa    5880
atgaagtttt aaatcaagcc aatctgaat aatgttacaa ccaattaacc aattctgatt    5940
agaaaaactc atcgagcatc aaatgaaact gcaatttatt catatcagga ttatcaatac    6000 catattttg aaaaagccgt ttctgtaatg aaggagaaaa ctcaccgagg cagttccata    6060
ggatggcaag atcctggtat cggtctgcga ttccgactcg tccaacatca atacaaccta    6120
ttaatttccc ctcgtcaaaa ataaggttat caagtgagaa atcaccatga gtgacgactg    6180
aatccggtga gaatggcaaa agtttatgca tttctttcca cttgttca acaggccagc    6240 cattacgctc gtcatcaaaa tcactcgcat caaccaaacc gttattcatt cgtgattgcg    6300
cctgagcgag acgaaatacg cgatcgctgt taaaaggaca attacaaaca ggaatcgaat    6360
gcaaccggcg caggaacact gccagcgcat caacaatatt ttcacctgaa tcaggatatt    6420
cttctaatac ctggaatgct gttttttccgg ggatcgcagt ggtgagtaac catgcatcat    6480
caggagtacg gataaaatgc ttgatggtcg gaagaggcat aaattccgtc agccagttta    6540
gtctgaccat ctcatctgta acatcattgg caacgctacc tttgccatgt ttcagaaaca    6600
actctggcgc atcgggcttc ccatacaagc gatagattgt cgcacctgat tgcccgacat    6660
tatcgcgagc ccatttatac ccatataaat cagcatccat gttggaattt aatcgcggcc    6720
tcgacgtttc ccgttgaata tggctcataa cacccccttgt attactgttt atgtaagcag    6780
acagttttat tgttcatgat gatatatttt tatcttgtgc aatgtaacat cagagatttt    6840
gagacacggg ccagagctgc a                                              6861

<210> SEQ ID NO 22
<211> LENGTH: 6574
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (146)..(396)
<223> OTHER INFORMATION: lacZalpha; Codon start: 1; Gene: lacZ fragment;
      Product: LacZalpha fragment of beta-galactosidase; Translation:
      LAVVLQRRDWENPGVTQLNRLAAHPPFASWRNSEEARTDRPSQQLRSLNGEWRLMRYFLLTHLCG
      ISHRIWCTLSTICSDAA*
<220> FEATURE:
<221> NAME/KEY: misc_feature
<222> LOCATION: (410)..(799)
<223> OTHER INFORMATION: VCP_b UTR
<220> FEATURE:
<221> NAME/KEY: misc_feature
<222> LOCATION: (802)..(1521)
<223> OTHER INFORMATION: RtEGFP
<220> FEATURE:
<221> NAME/KEY: promoter
<222> LOCATION: (1522)..(2679)
<223> OTHER INFORMATION: bidirectional promoter
```

```
<220> FEATURE:
<221> NAME/KEY: misc_feature
<222> LOCATION: (1522)..(1527)
<223> OTHER INFORMATION: Feature 24; Note: KOZAK:
      CTCTCTCAAGT.ATG.Protein.TAA. Add ORF by ATG-ORF-TAA. (no overhang
      needed)
<220> FEATURE:
<221> NAME/KEY: misc_feature
<222> LOCATION: (2674)..(2674)
<223> OTHER INFORMATION: Feature 24; Note: Promoter protein junction:
      CCACCACCACTTCTTAAGt.ATG.protein.taa.
<220> FEATURE:
<221> NAME/KEY: misc_feature
<222> LOCATION: (2680)..(2696)
<223> OTHER INFORMATION: replace; Note: Add gene via blnt phusion PCR
      T.ATG.orf.TAA
<220> FEATURE:
<221> NAME/KEY: misc_feature
<222> LOCATION: (2700)..(2700)
<223> OTHER INFORMATION: stop codon
<220> FEATURE:
<221> NAME/KEY: misc_feature
<222> LOCATION: (2701)..(2944)
<223> OTHER INFORMATION: VCP1 UTR
<220> FEATURE:
<221> NAME/KEY: promoter
<222> LOCATION: (2945)..(3216)
<223> OTHER INFORMATION: ACP prom
<220> FEATURE:
<221> NAME/KEY: misc_feature
<222> LOCATION: (3211)..(3211)
<223> OTHER INFORMATION: KOZAK; Note: Add gibson fragment by adding
      C.ATG.ORF.TAA. Restored sequence is CTCTTCAC.TTA.ACC.ATG
<220> FEATURE:
<221> NAME/KEY: misc_feature
<222> LOCATION: (3216)..(3227)
<223> OTHER INFORMATION: replace; Note: Replace by gibson. Digest NcoI
      first, then add CATG.PROTEIN.TAA. CATG is C with start methionine.
      Use Phusion for insert.
<220> FEATURE:
<221> NAME/KEY: misc_feature
<222> LOCATION: (3217)..(3219)
<223> OTHER INFORMATION: ACP start ATG
<220> FEATURE:
<221> NAME/KEY: misc_feature
<222> LOCATION: (3231)..(3407)
<223> OTHER INFORMATION: FBA UTR
<220> FEATURE:
<221> NAME/KEY: promoter
<222> LOCATION: (3408)..(3888)
<223> OTHER INFORMATION: gapdh promoter
<220> FEATURE:
<221> NAME/KEY: misc_feature
<222> LOCATION: (3889)..(4263)
<223> OTHER INFORMATION: BleoR; Gene: Sh ble from Streptoalloteichus
      hindustanus; Product: antibiotic-binding protein; Note: confers
      resistance to bleomycin, phleomycin, and Zeocin(TM)
<220> FEATURE:
<221> NAME/KEY: misc_feature
<222> LOCATION: (4264)..(4448)
<223> OTHER INFORMATION: GAPDH terminator
<220> FEATURE:
<221> NAME/KEY: misc_feature
<222> LOCATION: (4467)..(4488)
<223> OTHER INFORMATION: lacZalpha; Gene: lacZ fragment; Product:
      LacZalpha fragment of beta-galactosidase; Translation: MTMITPS
<220> FEATURE:
<221> NAME/KEY: primer_bind
<222> LOCATION: (4484)..(4500)
<223> OTHER INFORMATION: M13 rev; Note: common sequencing primer, one of
      multiple similar variants
<220> FEATURE:
<221> NAME/KEY: protein_bind
<222> LOCATION: (4508)..(4524)
<223> OTHER INFORMATION: lac operator; Bound moiety: lac repressor
      encoded by lacI; Note: The lac repressor binds to the lac operator
      to inhibit transcription in E. coli. This inhibition can be
      relieved by adding lactose or isopropyl-beta-D-
      thiogalactopyranoside (IPTG).
```

```
<220> FEATURE:
<221> NAME/KEY: promoter
<222> LOCATION: (4532)..(4562)
<223> OTHER INFORMATION: lac promoter; Note: promoter for the E. coli
      lac operon
<220> FEATURE:
<221> NAME/KEY: protein_bind
<222> LOCATION: (4577)..(4598)
<223> OTHER INFORMATION: CAP binding site; Bound moiety: E. coli
      catabolite activator protein; Note: CAP binding activates
      transcription in the presence of cAMP.
<220> FEATURE:
<221> NAME/KEY: rep_origin
<222> LOCATION: (4886)..(5474)
<223> OTHER INFORMATION: ori; Direction: LEFT; Note: high-copy-number
      ColE1/pMB1/pBR322/pUC origin of replication
<220> FEATURE:
<221> NAME/KEY: misc_feature
<222> LOCATION: (5652)..(6461)
<223> OTHER INFORMATION: KanR; Gene: aph(3')-Ia; Product: aminoglycoside
      phosphotransferase; Note: confers resistance to kanamycin in
      bacteria or G418 (Geneticin) in eukaryotes

<400> SEQUENCE: 22
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagagaatt cgtttaaacc agtgggataa     420
aaggcagtcc gaaggtttcc gtcatcctcg tcctcgttct cgttttccac ctactcatct     480
tccgtttctt gagtgcgtcg ccgctgggtt ttcctgaaat aaacgctctt tcatatattt     540 tttttcatc tttttttctt ctattgtttt tttgacttg tctttgacct tgtctgtagc     600
tcttaacaga tcaaaggaaa agcgaaggcg ccgcatgatc ctcgtccttc acgaaacaca     660
aacatcagcc tcttcaccct ctttccctgt ttcctgctac gaaatcgaca acattcaaca     720
agtcagaaac gctcctcttc actgaacaca caatcgaccg ctgctttcct ccttccctcc     780
gcagtaatca acacgtctat tctacttgta gagctcgtcc atgccgaggg tgatgccggc     840
ggcggtgacg aactcgagga ggaccatgtg gtcgcgcttc tcgttcgggt ccttcgagag     900
ggccgactgg gtcgagaggt agtggttgtc cgggaggagg accgggccgt cgccgatcgg     960
ggtgttctgc tggtagtggt cggcgagctg gaccgagccg tcctcgatgt tgtggcggat    1020
cttgaagttg accttgatgc cgttcttctg cttgtcggcc atgatgtaga cgttgtgcga    1080
gttgtagttg tactcgagct tgtggccgag gatgttgccg tcctccttga gtcgatgcc    1140 cttgagctcg atgcggttga cgagggtgtc gccctgaac ttgacctcgg cgcgggtctt    1200
gtagttgccg tcgtccttga agaagatggt gcgctcctgg acgtagccct ccggcatggc    1260
cgacttgaag aagtcgtgct gcttcatgtg gtccgggtag cgcgagaagc actggacgcc    1320
gtaggtgagg gtggtgacga gggtcggcca cgggaccggg agcttgccgg tggtgcagat    1380
gaacttgagg gtgagcttgc cgtaggtggc gtcgccctcg ccctcgcccg agaccgagaa    1440
cttgtggccg ttgacgtcgc cgtcgagctc gacgaggatc gggacgacgc cggtgaagag    1500
ctcctcgccc ttcgagacca tacttgagag agtggtggag ttgactatcg tgtgagtgt    1560 ttggggaggg aaagggcgga gcgtgagtgc aatgcgaggt gggcgaagtg gcatgtgat    1620
```

-continued

```
aaatggctgt gtggtggagg ccttcgctgc gtgtctgtga ctgtcttgat tgtgtgctta   1680
gagtgagata ccaaagcaag atcttccctg ccatcccttc attgtcccac gggccgaaga   1740 gatgggggc ttgacgagag gacagggatg caggtgcgat gcggtcctgt cctatggggc   1800
aggaaccgct ggggtgcagt ggcacagaag acagaaggag aaaacacatg caccaaataa   1860
acatatgaca aagagtcaag cagtagtcaa aacaaccaaa acgtaagcaa gacggaacaa   1920
gatggcacgc gtctgcaaca gaccggctcg cgccgaacgt gcctcctgct tttcaacgat   1980
cctgcgaggt caaccaggat ttgctcgccg ggacgatttc atcccccttat caacgagccc   2040 ttgaggctcc aggcgtgctt ccacacccca gttggtaaca ggacattggg gcatcttgcc   2100
tatcttgtct tagtgccgaa agcctcaacg acctcctatg gggtctgctc aacgcctcaa   2160
ccttgcagta aggcatcccc gagggcaaga cccgcaaagc cttctgtcgt cggacaaagc   2220
ggagcgaggg aacaggctca gctcaaccct cttgagagcc cataagtgcc ccctgatcta   2280
tcttcaacag tctttccctg tcacaagaaa acccagctag ttgaccaagt tgctagagct   2340
gataccttgt acttcgctct ttgtgtgctt tacctgattg acatggaca gacctccccct   2400 tgctcttcct tctaggagcc tgggctctcg ctcttgttct ttcgagagac ctttcccttg   2460
agttgcgtat ccagcgatca agtatgaaga gtgctttcaa acctagatac gttctgccca   2520
gttctcttgc ccttttccac acgtgctcca atcttcaca cgactcgcac atacccgac    2580 gaaacccctc aaaacatcgc aacacttaca tcccgctcgt gtcccacccc cgatgccata   2640
tcctctacag cagcagcacc accaccacca cttcttaagg atcctatagc tggatcctga   2700
gcttctgtgg aagagccagt ggtagtagca gtagcagcag cagtagcagc cgcagcactc   2760
agtgttggcg cgagagattg tccatcccctt cttaacctac cggaagagaa ataaggcctt   2820
tctcccgtag ctgtcttcgt ttgtttgtgc tgattgcttg gtatgagagt gttgaatctc   2880
ctgcatcatg ttttctctg tagtcctttc ctaccccgt catttctttt tctccctggt     2940
tcttacccgt acacgccat gctacaccct gcctacacac gcgcacacgc gcacaaacac    3000
acacatacat caacacacac aatacagcaa tccgtgcctc tctcttactc tattcaagcg   3060
tgctgcgtgg cctttgactt cattcctctt gtccacccgc cggccaccag tagaaccagc   3120
accacgtcca ccctcatctc actcctcttt cccccacatc ccctactact ccatccttct   3180
catctacagt cacaccttcc tcctcttcac ttaaccatgg taaccatggt aagttacaag   3240
caggacggaa gagtggactc agatgggaaa atacaaatat ttatgaaggt gcacatttag   3300
attgcgactt tttcatgaca cagagacacg tggagatttt cttactcctc atctctgtgt   3360
cacttaattt cttttcatc cctttacaac agtgttggtg cgctcatcga ccgcacatct    3420
acctcgcacg ccacccataa cctaccacag gcggtgttca agcccgtggc tgcatgcgtc   3480
gtcccttccg ctaccacccc cgagcttgca cacgatggcg gctcgctcgt gagtggctgg   3540
tgcaaggcga aagcaaccac aatattctgg cctttgccat tttatattgc ctggccttga   3600
ccttgtaagc agcgtcccca cagcttcctc caccagcaca ctgtgtcccg catgtgtgga   3660
ttggggcagt gggcagtctt tcttgttgtc ttgcacgccc gctggaggtc aagttggatc   3720
agtatttgta catgcacgga agagagcgtg acgaggcgga acaaaccgc tccaagccat    3780 cttcccatac caagcaaaca caacacgtac tcaccctcca ctctccttgt ccttttttccc   3840 tctgacacgc gcacctacag caccccctcga cgaccctcac ctgtctaaat ggccaagttg   3900
accagtgcca ttccggtgct caccgcgcgc gacgtcgccg gagcggtcga gttctggacc   3960
gaccggctcg ggttctcccg ggacttcgtg gaggacgact tcgccggtgt ggtccgggac   4020
```

-continued

```
gacgtgaccc tgttcatcag cgcggtccag gaccaggtgg tgccggacaa caccctggcc      4080
tgggtgtggg tgcgcggcct ggacgagctg tacgccgagt ggtcggaggt cgtgtccacg      4140
aacttccggg acgcctccgg gccggccatg accgagatcg gcgagcagcc gtggggcgg       4200 gagttcgccc tgcgcgaccc ggccggcaac tgcgtgcact tcgtggccga ggagcaggac      4260
taaatctgtt agttgcaaca gtagcagcaa cagctgtagt ttttgtacgc gcagtgcctt      4320
gtgctaggag ggagtagcag tagtagtagc agcagcagca gcagcgacaa ttttatgtgt      4380
aaggcgtggt ccttgtgtgc tttgtgtctg ctttgtctct cgtgtgtcaa gaggcattcg      4440
tagggattgt ttaaacctcg agtataagct tggtgtaatc atggtcatag ctgtttcctg      4500
tgtgaaattg ttatccgctc acaattccac acaacatacg agccgaagc ataaagtgta       4560 aagcctgggg tgcctaatga gtgagctaac tcacattaat tgcgttgcgc tcactgcccg      4620
ctttccagtc gggaaacctg tcgtgccagc tgcattaatg aatcggccaa cgcgcgggga     4680
gaggcggttt gcgtattggg cgctcttccg cttcctcgct cactgactcg ctgcgctcgg     4740
tcgttcggct gcggcgagcg gtatcagctc actcaaaggc ggtaatacgg ttatccacag    4800
aatcagggga taacgcagga aagaacatgt gagcaaaagg ccagcaaaag gccaggaacc   4860
gtaaaaaggc cgcgttgctg gcgttttcc ataggctccg ccccctgac gagcatcaca      4920 aaaatcgacg ctcaagtcag aggtggcgaa acccgacagg actataaaga taccaggcgt   4980
ttccccctgg aagctccctc gtgcgctctc ctgttccgac cctgccgctt accggatacc    5040
tgtccgcctt tctcccttcg ggaagcgtgg cgctttctca tagctcacgc tgtaggtatc   5100
tcagttcggt gtaggtcgtt cgctccaagc tgggctgtgt gcacgaaccc cccgttcagc   5160
ccgaccgctg cgccttatcc ggtaactatc gtcttgagtc caacccggta agacacgact   5220
tatcgccact ggcagcagcc actggtaaca ggattagcag agcgaggtat gtaggcggtg   5280
ctacagagtt cttgaagtgg tggcctaact acggctacac tagaagaaca gtatttggta    5340
tctgcgctct gctgaagcca gttaccttcg gaaaaagagt tggtagctct tgatccggca    5400
aacaaaccac cgctggtagc ggtggttttt ttgtttgcaa gcagcagatt acgcgcagaa    5460
aaaaaggatc tcaagaagat cctttgatct tttctacggg gtctgacgct cagtggaacg    5520
aaaactcacg ttaagggatt ttggtcatga gattatcaaa aaggatcttc acctagatcc    5580
ttttaaatta aaaatgaagt tttaaatcaa gcccaatctg ataatgtta caaccaatta    5640 accaattctg attagaaaaa ctcatcgagc atcaaatgaa actgcaattt attcatatca    5700
ggattatcaa taccatattt ttgaaaaagc cgtttctgta atgaaggaga aaactcaccg   5760
aggcagttcc ataggatggc aagatcctgg tatcggtctg cgattccgac tcgtccaaca   5820
tcaatacaac ctattaattt cccctcgtca aaaataaggt tatcaagtga aaatcacca    5880 tgagtgacga ctgaatccgg tgagaatggc aaaagttat gcatttcttt ccagacttgt    5940
tcaacaggcc agccattacg ctcgtcatca aaatcactcg catcaaccaa accgttattc    6000
attcgtgatt gcgcctgagc gagacgaaat acgcgatcgc tgttaaaagg acaattacaa   6060
acaggaatcg aatgcaaccg gcgcaggaac actgccagcg catcaacaat attttcacct   6120
gaatcaggat attcttctaa tacctggaat gctgttttc cggggatcgc agtggtgagt    6180
aaccatgcat catcaggagt acggataaaa tgcttgatgg tcggaagagg cataaattcc    6240
gtcagccagt ttagtctgac catctcatct gtaacatcat tggcaacgct acctttgcca   6300
tgtttcagaa acaactctgg cgcatcgggc ttcccataca agcgatagat tgtcgcacct    6360
gattgcccga cattatcgcg agcccattta taccatata aatcagcatc catgttggaa    6420
```

-continued

```
tttaatcgcg gcctcgacgt tcccgttga atatggctca taacacccct tgtattactg    6480
tttatgtaag cagacagttt tattgttcat gatgatatat tttatcttg tgcaatgtaa    6540 catcagagat tttgagacac gggccagagc tgca                                6574
```

<210> SEQ ID NO 23
<211> LENGTH: 5872
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (146)..(396)
<223> OTHER INFORMATION: lacZalpha; Codon start: 1; Gene: lacZ fragment;
      Product: LacZalpha fragment of beta-galactosidase; Translation:
      LAVVLQRRDWENPGVTQLNRLAAHPPFASWRNSEEARTDRPSQQLRSLNGEWRLMRYFLLTHLCG
      ISHRIWCTLSTICSDAA*
<220> FEATURE:
<221> NAME/KEY: misc_feature
<222> LOCATION: (410)..(799)
<223> OTHER INFORMATION: VCP_b UTR
<220> FEATURE:
<221> NAME/KEY: misc_feature
<222> LOCATION: (802)..(819)
<223> OTHER INFORMATION: REPLACE; Note: Replace by XbaI digest. Insert
      ORF with ATG.PROTEIN.TAA. Kozak/Start met is AGT.ATG
<220> FEATURE:
<221> NAME/KEY: misc_feature
<222> LOCATION: (813)..(815)
<223> OTHER INFORMATION: startM; start methionine
<220> FEATURE:
<221> NAME/KEY: promoter
<222> LOCATION: (819)..(1977)
<223> OTHER INFORMATION: bidirectional promoter
<220> FEATURE:
<221> NAME/KEY: misc_feature
<222> LOCATION: (820)..(825)
<223> OTHER INFORMATION: Feature 24; Note: KOZAK:
      CTCTCTCAAGT.ATG.Protein.TAA. Add ORF by ATG-ORF-TAA. (no overhang
      needed)
<220> FEATURE:
<221> NAME/KEY: misc_feature
<222> LOCATION: (1972)..(1972)
<223> OTHER INFORMATION: Feature 24; Note: Promoter protein
      junction: CCACCACCACTTCTTAAGt.ATG.protein.taa.
<220> FEATURE:
<221> NAME/KEY: misc_feature
<222> LOCATION: (1978)..(1994)
<223> OTHER INFORMATION: replace; Note: Add gene via blnt phusion PCR
      T.ATG.orf.TAA
<220> FEATURE:
<221> NAME/KEY: misc_feature
<222> LOCATION: (1998)..(1998)
<223> OTHER INFORMATION: stop codon
<220> FEATURE:
<221> NAME/KEY: misc_feature
<222> LOCATION: (1999)..(2242)
<223> OTHER INFORMATION: VCP1 UTR
<220> FEATURE:
<221> NAME/KEY: promoter
<222> LOCATION: (2243)..(2514)
<223> OTHER INFORMATION: ACP prom
<220> FEATURE:
<221> NAME/KEY: misc_feature
<222> LOCATION: (2509)..(2509)
<223> OTHER INFORMATION: KOZAK; Note: Add gibson fragment by adding
      C.ATG.ORF.TAA. Restored sequence is CTCTTCAC.TTA.ACC.ATG.
<220> FEATURE:
<221> NAME/KEY: misc_feature
<222> LOCATION: (2514)..(2525)
<223> OTHER INFORMATION: replace; Note: Replace by gibson. Digest NcoI
      first, then add CATG.PROTEIN.TAA. CATG is C with start methionine.
      Use Phusion for insert.

```
<220> FEATURE:
<221> NAME/KEY: misc_feature
<222> LOCATION: (2515)..(2517)
<223> OTHER INFORMATION: ACP start ATG
<220> FEATURE:
<221> NAME/KEY: misc_feature
<222> LOCATION: (2529)..(2705)
<223> OTHER INFORMATION: FBA UTR
<220> FEATURE:
<221> NAME/KEY: promoter
<222> LOCATION: (2706)..(3186)
<223> OTHER INFORMATION: gapdh promoter
<220> FEATURE:
<221> NAME/KEY: misc_feature
<222> LOCATION: (3187)..(3561)
<223> OTHER INFORMATION: BleoR; Gene: Sh ble from Streptoalloteichus
      hindustanus; Product: antibiotic-binding protein; Note: confers
      resistance to bleomycin, phleomycin, and Zeocin(TM)
<220> FEATURE:
<221> NAME/KEY: misc_feature
<222> LOCATION: (3562)..(3746)
<223> OTHER INFORMATION: GAPDH terminator
<220> FEATURE:
<221> NAME/KEY: misc_feature
<222> LOCATION: (3765)..(3786)
<223> OTHER INFORMATION: lacZalpha; Gene: lacZ fragment; Product:
      LacZalpha fragment of beta-galactosidase; Translation: MTMITPS
<220> FEATURE:
<221> NAME/KEY: primer_bind
<222> LOCATION: (3782)..(3798)
<223> OTHER INFORMATION: M13 rev; Note: common sequencing primer, one of
      multiple similar variants
<220> FEATURE:
<221> NAME/KEY: protein_bind
<222> LOCATION: (3806)..(3822)
<223> OTHER INFORMATION: lac operator; Bound moiety: lac repressor
      encoded by lacI; Note: The lac repressor binds to the lac operator
      to inhibit transcription in E. coli. This inhibition can be
      relieved by adding lactose or isopropyl-beta-D-
      thiogalactopyranoside (IPTG).
<220> FEATURE:
<221> NAME/KEY: promoter
<222> LOCATION: (3830)..(3860)
<223> OTHER INFORMATION: lac promoter; Note: promoter for the E. coli
      lac operon
<220> FEATURE:
<221> NAME/KEY: protein_bind
<222> LOCATION: (3875)..(3896)
<223> OTHER INFORMATION: CAP binding site; Bound moiety: E. coli
      catabolite activator protein; Note: CAP binding activates
      transcription in the presence of cAMP.
<220> FEATURE:
<221> NAME/KEY: rep_origin
<222> LOCATION: (4184)..(4772)
<223> OTHER INFORMATION: ori; Direction: LEFT; Note: high-copy-number
      ColE1/pMB1/pBR322/pUC origin of replication
<220> FEATURE:
<221> NAME/KEY: misc_feature
<222> LOCATION: (4950)..(5759)
<223> OTHER INFORMATION: KanR; Gene: aph(3')-Ia; Product: aminoglycoside
      phosphotransferase; Note: confers resistance to kanamycin in
      bacteria or G418 (Geneticin) in eukaryotes

<400> SEQUENCE: 23
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagagaatt cgtttaaacc agtgggataa     420
```

```
aaggcagtcc gaaggtttcc gtcatcctcg tcctcgttct cgttttccac ctactcatct    480
tccgtttctt gagtgcgtcg ccgctgggtt ttcctgaaat aaacgctctt tcatattatt    540 tttttcatc tttttttctt ctattgtttt ttttgacttg tctttgacct tgtctgtagc     600
tcttaacaga tcaaaggaaa agcgaaggcg ccgcatgatc ctcgtccttc acgaaacaca    660
aacatcagcc tcttcaccct ctttccctgt ttcctgctac gaaatcgaca acattcaaca    720
agtcagaaac gctcctcttc actgaacaca caatcgaccg ctgcttttcct ccttccctcc   780 gcagtaatca acacgtctat tctagaaatc tacatctaga cttgagagag tggtggagtt    840
gactatcgtg tggagtgttt ggggagggaa agggcggagc gtgagtgcaa tgcgaggtgg    900
gcgaagtggg catgtgataa atggctgtgt ggtggaggcc ttcgctgcgt gtctgtgact    960
gtcttgattg tgtgcttaga gtgagatacc aaagcaagat cttccctgcc atcccttcat   1020
tgtcccacgg gccgaagaga tgggggggctt gacgagagga cagggatgca ggtgcgatgc   1080
ggtcctgtcc tatggggcag gaaccgctgg ggtgcagtgg cacagaagac agaaggagaa   1140
aacacatgca ccaaataaac atatgacaaa gagtcaagca gtagtcaaaa caaccaaaac   1200
gtaagcaaga cggaacaaga tggcacgcgt ctgcaacaga ccggctcgcg ccgaacgtgc   1260
ctcctgcttt tcaacgatcc tgcgaggtca accaggattt gctcgccggg acgatttcat   1320
ccccttatca acgagccctt gaggctccag gcgtgcttcc acaccccagt tggtaacagg   1380
acattggggc atcttgccta tcttgtctta gtgccgaaag cctcaacgac ctcctatggg   1440
gtctgctcaa cgcctcaacc ttgcagtaag gcatcccga gggcaagacc cgcaaagcct    1500
tctgtcgtcg gacaaagcgg agcgagggaa caggctcagc tcaaccctct tgagagccca   1560
taagtgcccc ctgatctatc ttcaacagtc tttccctgtc acaagaaaac ccagctagtt   1620
gaccaagttg ctagagctga taccttgtac ttcgctcttt gtgtgcttta cctgattgga   1680
catggacaga cctcccttg ctcttccttc taggagcctg ggctctcgct cttgttcttt     1740
cgagagacct ttcccttgag ttgcgtatcc agcgatcaag tatgaagagt gctttcaaac   1800
ctagatacgt tctgcccagt tctcttgccc ttttccacac gtgctccaca tcttcacacg   1860
actcgcacca tacccgacga aaccctcaa aacatcgcaa cacttacatc ccgctcgtgt     1920
cccacccccg atgccatatc ctctacagca gcagcaccac caccaccact tcttaaggat   1980
cctatagctg gatcctgagc ttctgtggaa gagccagtgg tagtagcagt agcagcagca   2040
gtagcagccg cagcactcag tgttggcgcg agagattgtc catcccttct taacctaccg   2100 gaaagagaaat aaggccttc tcccgtagct gtcttcgttt gtttgtgctg attgcttggt    2160
atgagagtgt tgaatctcct gcatcatgtt tttctctgta gtccttcct accccgtca     2220 ttttctttc tccctggttc ttacccgtac acgccatgc tacaccctgc ctacacacgc     2280
gcacacgcgc acaaacacac acatacatca acacacacaa tacagcaatc cgtgcctctc   2340
tcttactcta ttcaagcgtg ctgcgtggcc tttgacttca ttcctcttgt ccacccgccg   2400
gccaccagta gaaccagcac cacgtccacc ctcatctcac tcctctttcc cccacatccc   2460
ctactactcc atccttctca tctacagtca caccttcctc ctcttcactt aaccatggta   2520
accatggtaa gttacaagca ggacggaaga gtggactcag atgggaaaat acaaatattt   2580
atgaaggtgc acatttagat tgcgacttt tcatgacaca gagacacgtg gagattttct    2640
tactcctcat ctctgtgtca cttaatttct ttttcatccc tttacaacag tgttggtgcg   2700
ctcatcgacc gcacatctac ctcgcacgcc acccataacc taccacaggc ggtgttcaag   2760
cccgtggctg catgcgtcgt cccttccgct accacccccg agcttgcaca cgatggcggc   2820
```

```
tcgctcgtga gtggctggtg caaggcgaaa gcaaccacaa tattctggcc tttgccattt    2880
tatattgcct ggccttgacc ttgtaagcag cgtccccaca gcttcctcca ccagcacact    2940
gtgtcccgca tgtgtggatt ggggcagtgg gcagtctttc ttgttgtctt gcacgcccgc    3000
tggaggtcaa gttggatcag tatttgtaca tgcacggaag agagcgtgac gaggcggaga    3060
caaaccgctc caagccatct tcccatacca agcaaacaca acacgtactc accctccact    3120
ctccttgtcc ttttttccctc tgacacgcgc acctacagca cccctcgacg accctcacct    3180
gtctaaatgg ccaagttgac cagtgccgtt ccggtgctca ccgcgcgcga cgtcgccgga    3240
gcggtcgagt tctggaccga ccggctcggg ttctcccggg acttcgtgga ggacgacttc    3300
gccggtgtgg tccgggacga cgtgaccctg ttcatcagcg cggtccagga ccaggtggtg    3360
ccggacaaca ccctggcctg ggtgtgggtg cgcggcctgg acgagctgta cgccgagtgg    3420
tcggaggtcg tgtccacgaa cttccgggac gcctccgggc cggccatgac cgagatcggc    3480
gagcagccgt gggggcggga gttcgccctg cgcgacccgg ccggcaactg cgtgcacttc    3540
gtggccgagg agcaggacta aatctgttag ttgcaacagt agcagcaaca gctgtagttt    3600
ttgtacgcgc agtgccttgt gctaggaggg agtagcagta gtagtagcag cagcagcagc    3660
agcgacaatt ttatgtgtaa ggcgtggtcc ttgtgtgctt tgtgtctgct ttgtctctcg    3720
tgtgtcaaga ggcattcgta gggattgttt aaacctcgag tataagcttg gtgtaatcat    3780
ggtcatagct gtttcctgtg tgaaattgtt atccgctcac aattccacac aacatacgag    3840
ccggaagcat aaagtgtaaa gcctggggtg cctaatgagt gagctaactc acattaattg    3900
cgttgcgctc actgcccgct ttccagtcgg gaaacctgtc gtgccagctg cattaatgaa    3960
tcggccaacg cgcggggaga ggcggtttgc gtattgggcg ctcttccgct tcctcgctca    4020
ctgactcgct gcgctcggtc gttcggctgc ggcgagcggt atcagctcac tcaaaggcgg    4080
taatacggtt atccacagaa tcaggggata acgcaggaaa gaacatgtga gcaaaaggcc    4140
agcaaaaggc caggaaccgt aaaaaggccg cgttgctggc gtttttccat aggctccgcc    4200
cccctgacga gcatcacaaa aatcgacgct caagtcagag gtggcgaaac ccgacaggac    4260
tataaagata ccaggcgttt ccccctggaa gctccctcgt gcgctctcct gttccgaccc    4320
tgccgcttac cggatacctg tccgcctttc tcccttcggg aagcgtggcg ctttctcata    4380
gctcacgctg taggtatctc agttcggtgt aggtcgttcg ctccaagctg ggctgtgtgc    4440
acgaaccccc cgttcagccc gaccgctgcg ccttatccgg taactatcgt cttgagtcca    4500
acccggtaag acacgactta tcgccactgg cagcagccac tggtaacagg attagcagag    4560
cgaggtatgt aggcggtgct acagagttct tgaagtggtg gcctaactac ggctacacta    4620
gaagaacagt atttggtatc tgcgctctgc tgaagccagt taccttcgga aaaagagttg    4680
gtagctcttg atccggcaaa caaaccaccg ctggtagcgg tggtttttttt gtttgcaagc    4740
agcagattac gcgcagaaaa aaaggatctc aagaagatcc tttgatcttt tctacggggt    4800
ctgacgctca gtggaacgaa aactcacgtt aagggatttt ggtcatgaga ttatcaaaaa    4860
ggatcttcac ctagatcctt ttaaattaaa aatgaagttt taaatcaagc ccaatctgaa    4920
taatgttaca accaattaac caattctgat tagaaaaact catcgagcat caaatgaaac    4980
tgcaatttat tcatatcagg attatcaata ccatattttt gaaaagccg tttctgtaat    5040
gaaggagaaa actcaccgag gcagttccat aggatggcaa gatcctggta tcggtctgcg    5100
attccgactc gtccaacatc aatacaacct attaatttcc cctcgtcaaa aataaggtta    5160
```

```
tcaagtgaga aatcaccatg agtgacgact gaatccggtg agaatggcaa aagtttatgc    5220
atttctttcc agacttgttc aacaggccag ccattacgct cgtcatcaaa atcactcgca    5280
tcaaccaaac cgttattcat tcgtgattgc gcctgagcga gacgaaatac gcgatcgctg    5340
ttaaaaggac aattacaaac aggaatcgaa tgcaaccggc gcaggaacac tgccagcgca    5400
tcaacaatat tttcacctga atcaggatat tcttctaata cctggaatgc tgttttccg     5460 gggatcgcag tggtgagtaa ccatgcatca tcaggagtac ggataaaatg cttgatggtc    5520
ggaagaggca taaattccgt cagccagttt agtctgacca tctcatctgt aacatcattg    5580
gcaacgctac ctttgccatg tttcagaaac aactctggcg catcgggctt cccatacaag    5640
cgatagattg tcgcacctga ttgcccgaca ttatcgcgag cccatttata cccatataaa    5700
tcagcatcca tgttggaatt taatcgcggc ctcgacgttt cccgttgaat atggctcata    5760 acacccctttg tattactgtt tatgtaagca gacagtttta ttgttcatga tgatatattt    5820
ttatcttgtg caatgtaaca tcagagattt tgagacacgg gccagagctg ca            5872
```

<210> SEQ ID NO 24
<211> LENGTH: 239
<212> TYPE: PRT
<213> ORGANISM: Artificial Sequence
<220> FEATURE:
<223> OTHER INFORMATION: Synthetic construct

<400> SEQUENCE: 24

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```